(12) United States Patent
Boock et al.

(10) Patent No.: US 7,828,728 B2
(45) Date of Patent: Nov. 9, 2010

(54) ANALYTE SENSOR

(75) Inventors: Robert Boock, San Diego, CA (US);
Monica Rixman, San Diego, CA (US);
James H. Brauker, San Diego, CA
(US); James R. Petisce, San Diego, CA
(US); Peter C. Simpson, Del Mar, CA
(US); Mark Brister, Encinitas, CA
(US); Mark A. Tapsak, Orangeville, PA
(US); Victoria Carr-Brendel,
Pleasanton, CA (US)

(73) Assignee: DexCom, Inc., San Diego, CA (US)

( * ) Notice: Subject to any disclaimer, the term of this patent is extended or adjusted under 35 U.S.C. 154(b) by 319 days.

(21) Appl. No.: 11/675,063

(22) Filed: Feb. 14, 2007

(65) Prior Publication Data

US 2007/0197890 A1 Aug. 23, 2007

Related U.S. Application Data

(63) Continuation-in-part of application No. 11/404,417, filed on Apr. 14, 2006, now Pat. No. 7,613,491, and a continuation-in-part of application No. 10/896,639, filed on Jul. 21, 2004, now Pat. No. 7,379,765.

(60) Provisional application No. 60/490,009, filed on Jul. 25, 2003.

(51) Int. Cl.
*A61B 5/00* (2006.01)
*A61B 5/05* (2006.01)

(52) U.S. Cl. .................. 600/365; 600/345; 600/347

(58) Field of Classification Search ............. 600/345, 600/347, 365; 204/403.01
See application file for complete search history.

(56) References Cited

U.S. PATENT DOCUMENTS

| | | | |
|---|---|---|---|
| 2,830,020 A * | 4/1958 | Christmann et al. ......... 508/210 |
| 3,220,960 A * | 11/1965 | Lim et al. ................... 521/149 |
| 3,562,352 A | 2/1971 | Nyilas | |
| 3,607,329 A | 9/1971 | Manjikian | |
| 3,746,588 A | 7/1973 | Brown, Jr. | |
| 3,898,984 A | 8/1975 | Mandel et al. | |
| 3,943,918 A | 3/1976 | Lewis | |
| 3,979,274 A | 9/1976 | Newman | |
| 4,040,908 A | 8/1977 | Clark, Jr. | |
| 4,073,713 A | 2/1978 | Newman | |
| 4,136,250 A | 1/1979 | Mueller et al. | |
| 4,253,469 A | 3/1981 | Aslan | |
| 4,256,561 A * | 3/1981 | Schindler et al. ............ 204/418 |
| 4,260,725 A | 4/1981 | Keogh et al. | |
| 4,267,145 A * | 5/1981 | Wysong ...................... 264/563 |
| 4,292,423 A | 9/1981 | Kaufmann et al. | |
| 4,403,984 A | 9/1983 | Ash et al. | |
| 4,415,666 A | 11/1983 | D'Orazio et al. | |
| 4,418,148 A | 11/1983 | Oberhardt | |
| 4,431,004 A | 2/1984 | Bessman et al. | |
| 4,442,841 A | 4/1984 | Uehara et al. | |
| 4,454,295 A | 6/1984 | Wittmann et al. | |
| 4,482,666 A * | 11/1984 | Reeves ....................... 524/389 |
| 4,484,987 A | 11/1984 | Gough | |
| 4,493,714 A | 1/1985 | Ueda et al. | |
| 4,494,950 A | 1/1985 | Fischell | |
| 4,527,999 A | 7/1985 | Lee | |
| 4,545,382 A | 10/1985 | Higgins et al. | |
| 4,554,927 A | 11/1985 | Fussell | |
| 4,602,922 A | 7/1986 | Cabasso et al. | |
| 4,632,968 A | 12/1986 | Yokota et al. | |
| 4,644,046 A | 2/1987 | Yamada | |
| 4,647,643 A | 3/1987 | Zdrabala et al. | |
| 4,650,547 A | 3/1987 | Gough | |
| 4,671,288 A | 6/1987 | Gough | |
| 4,672,970 A | 6/1987 | Uchida et al. | |
| 4,680,268 A | 7/1987 | Clark, Jr. | |
| 4,684,538 A | 8/1987 | Klemarczyk | |
| 4,685,463 A | 8/1987 | Williams | |
| 4,686,044 A | 8/1987 | Behnke et al. | |
| 4,686,137 A | 8/1987 | Ward, Jr. et al. | |
| 4,689,149 A | 8/1987 | Kanno et al. | |
| 4,689,309 A | 8/1987 | Jones | |
| 4,703,756 A | 11/1987 | Gough et al. | |
| 4,711,245 A | 12/1987 | Higgins | |
| 4,721,677 A | 1/1988 | Clark, Jr. | |
| 4,726,381 A | 2/1988 | Jones | |
| 4,731,726 A | 3/1988 | Allen | |

(Continued)

FOREIGN PATENT DOCUMENTS

EP 0 098 592 1/1984

(Continued)

OTHER PUBLICATIONS

ISR and WO for PCT/US04/023454 filed Jul. 21, 2004.

(Continued)

*Primary Examiner*—Patricia C Mallari
(74) *Attorney, Agent, or Firm*—Knobbe Martens Olson & Bear LLP

(57) ABSTRACT

The present invention relates generally to membranes utilized with implantable devices, such as devices for the detection of analyte concentrations in a biological sample. More particularly, the invention relates to novel silicone-hydrophilic polymer blend membranes, and to devices and implantable devices including these membranes.

43 Claims, 19 Drawing Sheets

U.S. PATENT DOCUMENTS

| | | |
|---|---|---|
| 4,739,380 A | 4/1988 | Lauks et al. |
| 4,757,022 A | 7/1988 | Shults et al. |
| 4,763,658 A | 8/1988 | Jones |
| 4,781,733 A | 11/1988 | Babcock et al. |
| 4,786,657 A | 11/1988 | Hammar et al. |
| 4,793,555 A | 12/1988 | Lee et al. |
| 4,795,542 A | 1/1989 | Ross et al. |
| 4,803,243 A | 2/1989 | Fujimoto et al. |
| 4,805,625 A | 2/1989 | Wyler |
| 4,813,424 A | 3/1989 | Wilkins |
| 4,822,336 A | 4/1989 | DiTraglia |
| 4,832,034 A | 5/1989 | Pizziconi |
| 4,849,458 A | 7/1989 | Reed et al. |
| 4,852,573 A | 8/1989 | Kennedy |
| 4,861,830 A | 8/1989 | Ward, Jr. |
| 4,871,440 A | 10/1989 | Nagata et al. |
| 4,880,883 A | 11/1989 | Grasel et al. |
| 4,886,740 A | 12/1989 | Vadgama |
| 4,890,620 A | 1/1990 | Gough |
| 4,908,208 A | 3/1990 | Lee et al. |
| 4,909,908 A | 3/1990 | Ross et al. |
| 4,919,141 A | 4/1990 | Zier et al. |
| 4,938,860 A | 7/1990 | Wogoman |
| 4,951,657 A | 8/1990 | Pfister et al. |
| 4,952,618 A | 8/1990 | Olsen |
| 4,953,552 A | 9/1990 | DeMarzo |
| 4,954,381 A | 9/1990 | Cabasso et al. |
| 4,960,594 A | 10/1990 | Honeycutt |
| 4,961,954 A | 10/1990 | Goldberg et al. |
| 4,963,595 A | 10/1990 | Ward et al. |
| 4,970,145 A | 11/1990 | Bennetto et al. |
| 4,973,320 A | 11/1990 | Brenner et al. |
| 4,988,341 A | 1/1991 | Columbus et al. |
| 4,994,167 A | 2/1991 | Shults et al. |
| 5,002,590 A | 3/1991 | Friesen et al. |
| 5,010,141 A | 4/1991 | Mueller |
| 5,030,333 A | 7/1991 | Clark, Jr. |
| 5,034,461 A | 7/1991 | Lai et al. |
| 5,045,601 A | 9/1991 | Capelli et al. |
| 5,050,612 A | 9/1991 | Matsumura |
| 5,063,081 A | 11/1991 | Cozzette et al. |
| 5,070,169 A | 12/1991 | Robertson et al. |
| 5,071,452 A | 12/1991 | Avrillon et al. |
| 5,094,876 A | 3/1992 | Goldberg et al. |
| 5,100,689 A | 3/1992 | Goldberg et al. |
| 5,108,819 A | 4/1992 | Heller et al. |
| 5,115,056 A | 5/1992 | Mueller et al. |
| 5,120,813 A | 6/1992 | Ward, Jr. |
| 5,128,408 A | 7/1992 | Tanaka et al. |
| 5,135,297 A | 8/1992 | Valint et al. |
| 5,137,028 A | 8/1992 | Nishimura |
| 5,140,985 A | 8/1992 | Schroeder et al. |
| 5,147,725 A | 9/1992 | Pinchuk |
| 5,155,149 A | 10/1992 | Atwater et al. |
| 5,160,418 A | 11/1992 | Mullen |
| 5,165,407 A | 11/1992 | Wilson et al. |
| 5,169,906 A | 12/1992 | Cray et al. |
| 5,171,689 A | 12/1992 | Kawaguri et al. |
| 5,183,549 A | 2/1993 | Joseph et al. |
| 5,200,051 A | 4/1993 | Cozzette et al. |
| 5,202,261 A | 4/1993 | Musho et al. |
| 5,208,313 A | 5/1993 | Krishnan |
| 5,212,050 A | 5/1993 | Mier et al. |
| 5,219,965 A | 6/1993 | Valint et al. |
| 5,221,724 A | 6/1993 | Li et al. |
| 5,235,003 A | 8/1993 | Ward et al. |
| 5,242,835 A | 9/1993 | Jensen |
| 5,249,576 A | 10/1993 | Goldberger et al. |
| 5,250,439 A | 10/1993 | Musho et al. |
| 5,264,104 A | 11/1993 | Gregg et al. |
| 5,269,891 A | 12/1993 | Colin |
| 5,284,140 A | 2/1994 | Allen et al. |
| 5,286,364 A | 2/1994 | Yacynych et al. |
| 5,296,144 A | 3/1994 | Sternina et al. |
| 5,299,571 A | 4/1994 | Mastrototaro |
| 5,316,008 A | 5/1994 | Suga et al. |
| 5,322,063 A | 6/1994 | Allen et al. |
| 5,324,322 A | 6/1994 | Grill et al. |
| 5,331,555 A | 7/1994 | Hashimoto et al. |
| 5,334,681 A | 8/1994 | Mueller et al. |
| 5,342,693 A | 8/1994 | Winters et al. |
| 5,352,348 A | 10/1994 | Young et al. |
| 5,372,133 A | 12/1994 | Hogen Esch |
| 5,376,400 A | 12/1994 | Goldberg et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,397,451 A | 3/1995 | Senda et al. |
| 5,397,848 A | 3/1995 | Yang et al. |
| 5,411,866 A | 5/1995 | Luong |
| 5,426,158 A | 6/1995 | Mueller et al. |
| 5,428,123 A | 6/1995 | Ward et al. |
| 5,429,735 A | 7/1995 | Johnson et al. |
| 5,438,984 A | 8/1995 | Schoendorfer |
| 5,458,631 A | 10/1995 | Xavier et al. |
| 5,462,051 A | 10/1995 | Oka et al. |
| 5,466,575 A | 11/1995 | Cozzette et al. |
| 5,469,846 A | 11/1995 | Khan |
| 5,476,094 A | 12/1995 | Allen et al. |
| 5,494,562 A | 2/1996 | Maley et al. |
| 5,497,772 A | 3/1996 | Schulman et al. |
| 5,507,288 A | 4/1996 | Bocker et al. |
| 5,513,636 A | 5/1996 | Palti |
| 5,518,601 A | 5/1996 | Foos et al. |
| 5,521,273 A | 5/1996 | Yilgor et al. |
| 5,531,878 A | 7/1996 | Vadgama et al. |
| 5,541,305 A | 7/1996 | Yokota et al. |
| 5,552,112 A | 9/1996 | Schiffmann |
| 5,554,339 A | 9/1996 | Cozzette |
| 5,564,439 A | 10/1996 | Picha |
| 5,568,806 A | 10/1996 | Cheney, II et al. |
| 5,569,186 A | 10/1996 | Lord et al. |
| 5,575,930 A | 11/1996 | Tietje-Girault et al. |
| 5,582,184 A | 12/1996 | Erickson et al. |
| 5,584,813 A | 12/1996 | Livingston et al. |
| 5,584,876 A | 12/1996 | Bruchman et al. |
| 5,586,553 A | 12/1996 | Halili et al. |
| 5,589,563 A | 12/1996 | Ward et al. |
| 5,590,651 A | 1/1997 | Shaffer et al. |
| 5,593,852 A | 1/1997 | Heller et al. |
| 5,605,152 A | 2/1997 | Slate et al. |
| 5,611,900 A * | 3/1997 | Worden et al. ............ 204/403.1 |
| 5,624,537 A | 4/1997 | Turner et al. |
| 5,640,954 A | 6/1997 | Pfeiffer |
| 5,665,222 A | 9/1997 | Heller et al. |
| 5,670,097 A | 9/1997 | Duan et al. |
| 5,695,623 A | 12/1997 | Michel et al. |
| 5,700,559 A | 12/1997 | Sheu et al. |
| 5,703,359 A | 12/1997 | Wampler, III |
| 5,711,861 A | 1/1998 | Ward et al. |
| 5,741,330 A | 4/1998 | Brauker et al. |
| 5,743,262 A | 4/1998 | Lepper, Jr. et al. |
| 5,746,898 A | 5/1998 | Preidel |
| 5,756,632 A | 5/1998 | Ward et al. |
| 5,760,155 A | 6/1998 | Mowrer et al. |
| 5,766,839 A | 6/1998 | Johnson et al. |
| 5,773,270 A | 6/1998 | D'Orazio et al. |
| 5,776,324 A | 7/1998 | Usala |
| 5,777,060 A * | 7/1998 | Van Antwerp ............... 528/28 |
| 5,783,054 A | 7/1998 | Raguse et al. |
| 5,786,439 A | 7/1998 | Van Antwerp et al. |
| 5,791,344 A | 8/1998 | Schulman et al. |
| 5,795,453 A | 8/1998 | Gilmartin |

| Patent | Kind | Date | Inventor |
|---|---|---|---|
| 5,795,774 | A | 8/1998 | Matsumoto et al. |
| 5,800,420 | A | 9/1998 | Gross |
| 5,804,048 | A | 9/1998 | Wong et al. |
| 5,807,375 | A | 9/1998 | Gross et al. |
| 5,807,636 | A | 9/1998 | Sheu et al. |
| 5,811,487 | A | 9/1998 | Schulz, Jr. et al. |
| 5,820,570 | A | 10/1998 | Erickson |
| 5,820,589 | A | 10/1998 | Torgerson et al. |
| 5,834,583 | A | 11/1998 | Hancock et al. |
| 5,837,377 | A | 11/1998 | Sheu et al. |
| 5,837,454 | A | 11/1998 | Cozzette et al. |
| 5,837,661 | A * | 11/1998 | Evans et al. .................. 510/122 |
| 5,843,069 | A | 12/1998 | Butler et al. |
| 5,863,972 | A | 1/1999 | Beckelmann et al. |
| 5,882,494 | A | 3/1999 | Van Antwerp |
| 5,885,566 | A | 3/1999 | Goldberg |
| 5,897,955 | A | 4/1999 | Drumheller |
| 5,914,026 | A | 6/1999 | Blubaugh, Jr. et al. |
| 5,914,182 | A | 6/1999 | Drumheller |
| 5,931,814 | A | 8/1999 | Alex et al. |
| 5,932,299 | A | 8/1999 | Katoot |
| 5,945,498 | A | 8/1999 | Hopken et al. |
| 5,947,127 | A * | 9/1999 | Tsugaya et al. ............. 131/332 |
| 5,954,643 | A | 9/1999 | Van Antwerp et al. |
| 5,955,066 | A * | 9/1999 | Sako et al. ................ 424/70.12 |
| 5,957,854 | A | 9/1999 | Besson et al. |
| 5,959,191 | A | 9/1999 | Lewis et al. |
| 5,961,451 | A | 10/1999 | Reber et al. |
| 5,964,745 | A | 10/1999 | Lyles et al. |
| 5,964,993 | A * | 10/1999 | Blubaugh et al. ...... 204/403.09 |
| 5,965,380 | A | 10/1999 | Heller et al. |
| 5,969,076 | A | 10/1999 | Lai et al. |
| 5,972,199 | A | 10/1999 | Heller |
| 5,972,369 | A | 10/1999 | Roorda et al. |
| 5,977,241 | A | 11/1999 | Koloski et al. |
| 5,985,129 | A | 11/1999 | Gough et al. |
| 6,001,067 | A | 12/1999 | Shults et al. |
| 6,002,954 | A | 12/1999 | Van Antwerp et al. |
| 6,007,845 | A | 12/1999 | Domb |
| 6,011,984 | A | 1/2000 | Van Antwerp et al. |
| 6,015,572 | A | 1/2000 | Lin et al. |
| 6,018,013 | A | 1/2000 | Yoshida et al. |
| 6,018,033 | A * | 1/2000 | Chen et al. .................... 536/4.1 |
| 6,022,463 | A | 2/2000 | Leader et al. |
| 6,030,827 | A | 2/2000 | Davis et al. |
| 6,039,913 | A | 3/2000 | Hirt et al. |
| 6,043,328 | A | 3/2000 | Domschke et al. |
| 6,051,389 | A | 4/2000 | Ahl et al. |
| 6,059,946 | A | 5/2000 | Yukawa et al. |
| 6,071,406 | A | 6/2000 | Tsou |
| 6,081,736 | A | 6/2000 | Colvin et al. |
| 6,083,523 | A | 7/2000 | Dionne et al. |
| 6,083,710 | A | 7/2000 | Heller et al. |
| 6,088,608 | A | 7/2000 | Schulman et al. |
| 6,091,975 | A | 7/2000 | Daddona et al. |
| 6,093,172 | A | 7/2000 | Funderburk et al. |
| 6,107,083 | A | 8/2000 | Collins et al. |
| 6,119,028 | A | 9/2000 | Schulman et al. |
| 6,121,009 | A | 9/2000 | Heller et al. |
| 6,122,536 | A | 9/2000 | Sun et al. |
| 6,134,461 | A | 10/2000 | Say et al. |
| 6,141,573 | A | 10/2000 | Kurnik et al. |
| 6,162,611 | A | 12/2000 | Heller et al. |
| 6,175,752 | B1 | 1/2001 | Say et al. |
| 6,180,416 | B1 | 1/2001 | Kurnik et al. |
| 6,200,772 | B1 | 3/2001 | Vadgama et al. |
| 6,212,416 | B1 | 4/2001 | Ward et al. |
| 6,233,471 | B1 | 5/2001 | Berner et al. |
| 6,248,067 | B1 | 6/2001 | Causey, III et al. |
| 6,256,522 | B1 | 7/2001 | Schultz |
| 6,259,937 | B1 | 7/2001 | Schulman et al. |
| 6,271,332 | B1 | 8/2001 | Lohmann et al. |
| 6,275,717 | B1 | 8/2001 | Gross et al. |
| 6,284,478 | B1 | 9/2001 | Heller et al. |
| 6,303,670 | B1 | 10/2001 | Fujino et al. |
| 6,306,594 | B1 | 10/2001 | Cozzette |
| 6,312,706 | B1 | 11/2001 | Lai et al. |
| 6,329,161 | B1 | 12/2001 | Heller et al. |
| 6,329,488 | B1 | 12/2001 | Terry et al. |
| 6,343,225 | B1 | 1/2002 | Clark, Jr. |
| 6,358,557 | B1 | 3/2002 | Wang et al. |
| 6,368,658 | B1 | 4/2002 | Schwarz et al. |
| 6,372,244 | B1 | 4/2002 | Antanavich et al. |
| 6,387,379 | B1 | 5/2002 | Goldberg et al. |
| 6,400,974 | B1 | 6/2002 | Lesho |
| 6,407,195 | B2 | 6/2002 | Sherman et al. |
| 6,413,393 | B1 | 7/2002 | Van Antwerp et al. |
| 6,413,396 | B1 | 7/2002 | Yang et al. |
| 6,424,847 | B1 | 7/2002 | Mastrototaro et al. |
| 6,442,413 | B1 | 8/2002 | Silver |
| 6,461,496 | B1 | 10/2002 | Feldman et al. |
| 6,466,810 | B1 | 10/2002 | Ward et al. |
| 6,477,395 | B2 | 11/2002 | Schulman et al. |
| 6,484,046 | B1 | 11/2002 | Say et al. |
| 6,512,939 | B1 | 1/2003 | Colvin et al. |
| 6,514,718 | B2 | 2/2003 | Heller et al. |
| 6,528,584 | B2 | 3/2003 | Kennedy et al. |
| 6,541,107 | B1 | 4/2003 | Zhong et al. |
| 6,545,085 | B2 | 4/2003 | Kilgour et al. |
| 6,551,496 | B1 | 4/2003 | Moles et al. |
| 6,554,982 | B1 | 4/2003 | Shin et al. |
| 6,565,509 | B1 | 5/2003 | Say et al. |
| 6,579,498 | B1 | 6/2003 | Eglise |
| 6,595,919 | B2 | 7/2003 | Berner et al. |
| 6,596,294 | B2 | 7/2003 | Lai et al. |
| 6,613,379 | B2 | 9/2003 | Ward et al. |
| 6,618,934 | B1 | 9/2003 | Feldman et al. |
| 6,633,772 | B2 | 10/2003 | Ford et al. |
| 6,642,015 | B2 | 11/2003 | Vachon et al. |
| 6,654,625 | B1 | 11/2003 | Say et al. |
| 6,670,115 | B1 * | 12/2003 | Zhang .......................... 435/5 |
| 6,689,265 | B2 | 2/2004 | Heller et al. |
| 6,692,528 | B2 | 2/2004 | Ward et al. |
| 6,702,857 | B2 | 3/2004 | Brauker et al. |
| 6,702,972 | B1 | 3/2004 | Markle |
| 6,721,587 | B2 | 4/2004 | Gough |
| 6,741,877 | B1 | 5/2004 | Shults et al. |
| 6,784,274 | B2 | 8/2004 | van Antwerp et al. |
| 6,789,634 | B1 | 9/2004 | Denton |
| 6,793,789 | B2 | 9/2004 | Choi et al. |
| 6,801,041 | B2 | 10/2004 | Karinka et al. |
| 6,802,957 | B2 | 10/2004 | Jung et al. |
| 6,815,186 | B2 | 11/2004 | Clark, Jr. |
| 6,858,218 | B2 | 2/2005 | Lai et al. |
| 6,862,465 | B2 | 3/2005 | Shults et al. |
| 6,867,262 | B1 | 3/2005 | Angel et al. |
| 6,881,551 | B2 | 4/2005 | Heller et al. |
| 6,895,263 | B2 | 5/2005 | Shin et al. |
| 6,895,265 | B2 | 5/2005 | Silver |
| 6,908,681 | B2 | 6/2005 | Terry et al. |
| 6,932,894 | B2 | 8/2005 | Mao et al. |
| 6,965,791 | B1 | 11/2005 | Hitchcock et al. |
| 6,969,451 | B2 | 11/2005 | Shin et al. |
| 6,973,706 | B2 | 12/2005 | Say et al. |
| 7,008,979 | B2 | 3/2006 | Schottman et al. |
| 7,014,948 | B2 | 3/2006 | Lee et al. |
| 7,033,322 | B2 | 4/2006 | Silver |
| 7,052,131 | B2 | 5/2006 | McCabe et al. |
| 7,074,307 | B2 | 7/2006 | Simpson et al. |
| 7,108,778 | B2 | 9/2006 | Simpson et al. |
| 7,110,803 | B2 | 9/2006 | Shults et al. |
| 7,118,667 | B2 | 10/2006 | Lee |
| 7,120,483 | B2 | 10/2006 | Russell et al. |
| 7,136,689 | B2 | 11/2006 | Shults et al. |
| 7,153,265 | B2 | 12/2006 | Vachon |
| 7,157,528 | B2 | 1/2007 | Ward |

| | | | | | | |
|---|---|---|---|---|---|---|
| 7,172,075 | B1 | 2/2007 | Ji | 2005/0051427 A1 | 3/2005 | Brauker et al. |
| 7,192,450 | B2 | 3/2007 | Brauker et al. | 2005/0051440 A1 | 3/2005 | Simpson et al. |
| 7,226,978 | B2 | 6/2007 | Tapsak et al. | 2005/0054909 A1 | 3/2005 | Petisce et al. |
| 7,229,471 | B2 | 6/2007 | Gale et al. | 2005/0056552 A1 | 3/2005 | Simpson et al. |
| 7,241,586 | B2 | 7/2007 | Gulati | 2005/0070770 A1 | 3/2005 | Dirac et al. |
| 7,248,906 | B2 | 7/2007 | Dirac et al. | 2005/0077584 A1 | 4/2005 | Uhland et al. |
| 7,276,029 | B2 | 10/2007 | Goode et al. | 2005/0079200 A1 | 4/2005 | Rathenow et al. |
| 7,279,174 | B2 | 10/2007 | Pacetti et al. | 2005/0090607 A1 | 4/2005 | Tapsak et al. |
| 7,335,286 | B2 | 2/2008 | Abel et al. | 2005/0044088 A1 | 5/2005 | Agus |
| 7,336,984 | B2 | 2/2008 | Gough et al. | 2005/0107677 A1 | 5/2005 | Ward et al. |
| 7,357,793 | B2 | 4/2008 | Pacetti | 2005/0112169 A1 | 5/2005 | Brauker et al. |
| 7,366,556 | B2 | 4/2008 | Brister et al. | 2005/0112172 A1 | 5/2005 | Pacetti |
| 7,379,765 | B2 | 5/2008 | Petisce et al. | 2005/0112358 A1 | 5/2005 | Potyrailo et al. |
| 7,417,164 | B2 | 8/2008 | Suri | 2005/0115832 A1 | 6/2005 | Simpson et al. |
| 7,423,074 | B2 | 9/2008 | Lai et al. | 2005/0118344 A1 | 6/2005 | Pacetti |
| 7,470,488 | B2 | 12/2008 | Lee et al. | 2005/0119720 A1 | 6/2005 | Gale et al. |
| 2002/0018843 | A1 | 2/2002 | Van Antwerp et al. | 2005/0121322 A1 | 6/2005 | Say |
| 2002/0055673 | A1 | 5/2002 | Van Antwerp et al. | 2005/0124873 A1 | 6/2005 | Shults et al. |
| 2002/0123087 | A1* | 9/2002 | Vachon et al. ............ 435/14 | 2005/0139489 A1 | 6/2005 | Davies et al. |
| 2002/0128546 | A1 | 9/2002 | Silver | 2005/0154272 A1 | 7/2005 | Dirac et al. |
| 2002/0185384 | A1 | 12/2002 | Leong et al. | 2005/0173245 A1 | 8/2005 | Feldman et al. |
| 2002/0193885 | A1 | 12/2002 | Legeay et al. | 2005/0176136 A1 | 8/2005 | Burd et al. |
| 2003/0006669 | A1 | 1/2003 | Pei et al. | 2005/0176678 A1 | 8/2005 | Horres et al. |
| 2003/0009093 | A1 | 1/2003 | Silver | 2005/0177036 A1 | 8/2005 | Shults et al. |
| 2003/0023317 | A1 | 1/2003 | Brauker et al. | 2005/0184641 A1 | 8/2005 | Armitage et al. |
| 2003/0032874 | A1 | 2/2003 | Rhodes et al. | 2005/0192557 A1 | 9/2005 | Brauker et al. |
| 2003/0059631 | A1 | 3/2003 | Al-Lamee | 2005/0196747 A1 | 9/2005 | Stiene |
| 2003/0065254 | A1 | 4/2003 | Schulman et al. | 2005/0197554 A1 | 9/2005 | Polcha |
| 2003/0069383 | A1 | 4/2003 | Van Antwerp et al. | 2005/0209665 A1 | 9/2005 | Hunter et al. |
| 2003/0088166 | A1 | 5/2003 | Say et al. | 2005/0233407 A1 | 10/2005 | Pamidi et al. |
| 2003/0096424 | A1 | 5/2003 | Mao et al. | 2005/0239154 A1 | 10/2005 | Feldman et al. |
| 2003/0104273 | A1 | 6/2003 | Lee et al. | 2005/0242479 A1 | 11/2005 | Petisce et al. |
| 2003/0125498 | A1 | 7/2003 | McCabe et al. | 2005/0245795 A1 | 11/2005 | Goode et al. |
| 2003/0132227 | A1 | 7/2003 | Geisler | 2005/0245799 A1 | 11/2005 | Brauker et al. |
| 2003/0134100 | A1 | 7/2003 | Mao et al. | 2005/0251083 A1 | 11/2005 | Carr-Brendel et al. |
| 2003/0134347 | A1 | 7/2003 | Heller et al. | 2005/0271546 A1 | 12/2005 | Gerber et al. |
| 2003/0157409 | A1 | 8/2003 | Huang et al. | 2005/0274665 A1 | 12/2005 | Heilmann et al. |
| 2003/0181794 | A1 | 9/2003 | Rini et al. | 2005/0282997 A1 | 12/2005 | Ward |
| 2003/0199745 | A1 | 10/2003 | Burson et al. | 2006/0003398 A1 | 1/2006 | Heller et al. |
| 2003/0199878 | A1 | 10/2003 | Pohjonen | 2006/0007391 A1 | 1/2006 | McCabe et al. |
| 2003/0203991 | A1 | 10/2003 | Schottman et al. | 2006/0008370 A1 | 1/2006 | Massaro et al. |
| 2003/0211050 | A1 | 11/2003 | Majeti et al. | 2006/0015020 A1 | 1/2006 | Neale et al. |
| 2003/0217966 | A1 | 11/2003 | Tapsak et al. | 2006/0016700 A1 | 1/2006 | Brister et al. |
| 2003/0225324 | A1 | 12/2003 | Anderson et al. | 2006/0019327 A1 | 1/2006 | Brister et al. |
| 2003/0228681 | A1* | 12/2003 | Ritts et al. ............ 435/287.2 | 2006/0020186 A1 | 1/2006 | Brister et al. |
| 2003/0235817 | A1 | 12/2003 | Bartkowiak et al. | 2006/0020187 A1 | 1/2006 | Brister et al. |
| 2004/0006263 | A1 | 1/2004 | Anderson et al. | 2006/0020188 A1 | 1/2006 | Kamath et al. |
| 2004/0011671 | A1 | 1/2004 | Shults et al. | 2006/0020189 A1 | 1/2006 | Brister et al. |
| 2004/0045879 | A1 | 3/2004 | Shults et al. | 2006/0020190 A1 | 1/2006 | Kamath et al. |
| 2004/0063167 | A1 | 4/2004 | Kaastrup et al. | 2006/0020191 A1 | 1/2006 | Brister et al. |
| 2004/0074785 | A1 | 4/2004 | Holker | 2006/0020192 A1 | 1/2006 | Brister et al. |
| 2004/0084306 | A1 | 5/2004 | Shin et al. | 2006/0036139 A1 | 2/2006 | Brister et al. |
| 2004/0106741 | A1 | 6/2004 | Kriesel et al. | 2006/0036140 A1 | 2/2006 | Brister et al. |
| 2004/0106857 | A1 | 6/2004 | Gough | 2006/0036141 A1 | 2/2006 | Kamath et al. |
| 2004/0111017 | A1 | 6/2004 | Say et al. | 2006/0036142 A1 | 2/2006 | Brister et al. |
| 2004/0111144 | A1 | 6/2004 | Lawin et al. | 2006/0036143 A1 | 2/2006 | Brister et al. |
| 2004/0120848 | A1 | 6/2004 | Teodorczyk | 2006/0036144 A1 | 2/2006 | Brister et al. |
| 2004/0138543 | A1 | 7/2004 | Russell et al. | 2006/0036145 A1 | 2/2006 | Brister et al. |
| 2004/0143173 | A1 | 7/2004 | Reghabi et al. | 2006/0040402 A1 | 2/2006 | Brauker et al. |
| 2004/0167801 | A1 | 8/2004 | Say et al. | 2006/0047095 A1 | 3/2006 | Pacetti |
| 2004/0176672 | A1 | 9/2004 | Silver et al. | 2006/0058868 A1 | 3/2006 | Gale et al. |
| 2004/0180391 | A1 | 9/2004 | Gratzl et al. | 2006/0065527 A1 | 3/2006 | Samproni |
| 2004/0186362 | A1 | 9/2004 | Brauker et al. | 2006/0067908 A1 | 3/2006 | Ding |
| 2004/0213985 | A1 | 10/2004 | Lee et al. | 2006/0068208 A1 | 3/2006 | Tapsak et al. |
| 2004/0224001 | A1 | 11/2004 | Pacetti et al. | 2006/0078908 A1 | 4/2006 | Pitner et al. |
| 2004/0228902 | A1 | 11/2004 | Benz | 2006/0079740 A1 | 4/2006 | Silver et al. |
| 2004/0234575 | A1 | 11/2004 | Horres et al. | 2006/0086624 A1 | 4/2006 | Tapsak et al. |
| 2005/0013842 | A1 | 1/2005 | Qiu et al. | 2006/0134165 A1 | 6/2006 | Pacetti |
| 2005/0027180 | A1 | 2/2005 | Goode et al. | 2006/0142524 A1 | 6/2006 | Lai et al. |
| 2005/0027463 | A1 | 2/2005 | Goode et al. | 2006/0142525 A1 | 6/2006 | Lai et al. |
| 2005/0031689 | A1 | 2/2005 | Shults et al. | 2006/0142526 A1 | 6/2006 | Lai et al. |
| 2005/0033132 | A1 | 2/2005 | Shults et al. | 2006/0142651 A1 | 6/2006 | Brister et al. |
| 2005/0043598 | A1 | 2/2005 | Goode et al. | 2006/0148985 A1 | 7/2006 | Karthauser |

| | | |
|---|---|---|
| 2006/0155180 A1 | 7/2006 | Brister et al. |
| 2006/0159718 A1 | 7/2006 | Rathenow et al. |
| 2006/0159981 A1 | 7/2006 | Heller |
| 2006/0171980 A1 | 8/2006 | Helmus et al. |
| 2006/0177379 A1 | 8/2006 | Asgari |
| 2006/0183178 A1 | 8/2006 | Gulati |
| 2006/0183871 A1 | 8/2006 | Ward et al. |
| 2006/0189856 A1 | 8/2006 | Petisce et al. |
| 2006/0195029 A1 | 8/2006 | Shults et al. |
| 2006/0198864 A1 | 9/2006 | Shults et al. |
| 2006/0200019 A1 | 9/2006 | Petisce et al. |
| 2006/0200970 A1 | 9/2006 | Brister et al. |
| 2006/0204536 A1 | 9/2006 | Shults et al. |
| 2006/0229512 A1 | 10/2006 | Petisce et al. |
| 2006/0249381 A1 | 11/2006 | Petisce et al. |
| 2006/0249446 A1 | 11/2006 | Yeager |
| 2006/0249447 A1 | 11/2006 | Yeager |
| 2006/0252027 A1 | 11/2006 | Petisce et al. |
| 2006/0253012 A1 | 11/2006 | Petisce et al. |
| 2006/0258761 A1 | 11/2006 | Boock et al. |
| 2006/0258929 A1 | 11/2006 | Goode et al. |
| 2006/0263673 A1 | 11/2006 | Kim et al. |
| 2006/0263839 A1 | 11/2006 | Ward et al. |
| 2006/0269586 A1 | 11/2006 | Pacetti |
| 2006/0275857 A1 | 12/2006 | Kjaer et al. |
| 2006/0275859 A1 | 12/2006 | Kjaer |
| 2006/0289307 A1 | 12/2006 | Yu et al. |
| 2006/0293487 A1 | 12/2006 | Gaymans et al. |
| 2007/0003588 A1 | 1/2007 | Chinn et al. |
| 2007/0007133 A1 | 1/2007 | Mang et al. |
| 2007/0032717 A1 | 2/2007 | Brister et al. |
| 2007/0032718 A1 | 2/2007 | Shults et al. |
| 2007/0038044 A1 | 2/2007 | Dobbles et al. |
| 2007/0045902 A1 | 3/2007 | Brauker et al. |
| 2007/0059196 A1 | 3/2007 | Brister et al. |
| 2007/0123963 A1 | 5/2007 | Krulevitch |
| 2007/0129524 A1 | 6/2007 | Sunkara |
| 2007/0135698 A1 | 6/2007 | Shah et al. |
| 2007/0142584 A1 | 6/2007 | Schorzman et al. |
| 2007/0155851 A1 | 7/2007 | Alli et al. |
| 2007/0161769 A1 | 7/2007 | Schorzman et al. |
| 2007/0163880 A1 | 7/2007 | Woo et al. |
| 2007/0166343 A1 | 7/2007 | Goerne et al. |
| 2007/0166364 A1 | 7/2007 | Beier et al. |
| 2007/0173709 A1 | 7/2007 | Petisce et al. |
| 2007/0173710 A1 | 7/2007 | Petisce et al. |
| 2007/0197890 A1 | 8/2007 | Boock et al. |
| 2007/0200267 A1 | 8/2007 | Tsai |
| 2007/0202562 A1 | 8/2007 | Curry |
| 2007/0203568 A1 | 8/2007 | Gale et al. |
| 2007/0213611 A1 | 9/2007 | Simpson et al. |
| 2007/0215491 A1 | 9/2007 | Heller et al. |
| 2007/0218097 A1 | 9/2007 | Heller et al. |
| 2007/0227907 A1 | 10/2007 | Shah et al. |
| 2007/0229757 A1 | 10/2007 | McCabe et al. |
| 2007/0233013 A1 | 10/2007 | Schoenberg |
| 2007/0235331 A1 | 10/2007 | Simpson et al. |
| 2007/0242215 A1 | 10/2007 | Schorzman et al. |
| 2007/0244379 A1 | 10/2007 | Boock et al. |
| 2007/0275193 A1 | 11/2007 | DeSimone et al. |
| 2007/0299385 A1 | 12/2007 | Santini et al. |
| 2007/0299409 A1 | 12/2007 | Whitbourne et al. |
| 2008/0001318 A1 | 1/2008 | Schorzman et al. |
| 2008/0021008 A1 | 1/2008 | Pacetti et al. |
| 2008/0027301 A1 | 1/2008 | Ward et al. |
| 2008/0031918 A1 | 2/2008 | Lawin et al. |
| 2008/0033269 A1 | 2/2008 | Zhang |
| 2008/0034972 A1 | 2/2008 | Gough et al. |
| 2008/0038307 A1 | 2/2008 | Hoffmann |
| 2008/0045824 A1 | 2/2008 | Tapsak et al. |
| 2008/0071027 A1 | 3/2008 | Pacetti |
| 2008/0076897 A1 | 3/2008 | Kunzler et al. |
| 2008/0081184 A1 | 4/2008 | Kubo et al. |
| 2008/0113207 A1 | 5/2008 | Pacetti et al. |
| 2008/0138497 A1 | 6/2008 | Pacetti et al. |
| 2008/0138498 A1 | 6/2008 | Pacetti et al. |
| 2008/0143014 A1 | 6/2008 | Tang |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0213460 A1 | 9/2008 | Benter et al. |
| 2008/0305009 A1 | 12/2008 | Gamsey et al. |
| 2008/0305506 A1 | 12/2008 | Suri |
| 2008/0312397 A1 | 12/2008 | Lai et al. |
| 2009/0004243 A1 | 1/2009 | Pacetti et al. |
| 2009/0012205 A1 | 1/2009 | Nakada et al. |
| 2009/0018418 A1 | 1/2009 | Markle et al. |
| 2009/0018426 A1 | 1/2009 | Markle et al. |
| 2009/0030294 A1 | 1/2009 | Petisce et al. |
| 2009/0045055 A1 | 2/2009 | Rhodes et al. |
| 2009/0061528 A1 | 3/2009 | Suri |
| 2009/0081803 A1 | 3/2009 | Gamsey et al. |
| 2009/0177143 A1 | 7/2009 | Markle et al. |
| 2009/0247855 A1 | 10/2009 | Boock et al. |
| 2009/0247856 A1 | 10/2009 | Boock et al. |
| 2009/0264719 A1 | 10/2009 | Markle et al. |

FOREIGN PATENT DOCUMENTS

| | | |
|---|---|---|
| EP | 0 127 958 | 12/1984 |
| EP | 0 291 130 | 11/1988 |
| EP | 0 313 951 | 5/1989 |
| EP | 0 320 109 | 6/1989 |
| EP | 0 353 328 | 2/1990 |
| EP | 0 362 145 | 4/1990 |
| EP | 0 390 390 | 10/1990 |
| EP | 0 396 788 | 11/1990 |
| EP | 0 535 898 | 4/1993 |
| EP | 0 563 795 | 10/1993 |
| EP | 0 817 809 | 1/1998 |
| EP | 0 862 648 | 9/1998 |
| EP | 0 885 932 | 12/1998 |
| EP | 1 153 571 | 11/2001 |
| GB | 1 442 303 | 7/1976 |
| GB | 2149918 | 6/1985 |
| GB | 2209836 | 5/1989 |
| JP | 57156004 | 9/1982 |
| JP | 57156005 | 9/1982 |
| JP | 58163402 | 9/1983 |
| JP | 58163403 | 9/1983 |
| JP | 59029693 | 2/1984 |
| JP | 59049803 | 3/1984 |
| JP | 59049805 | 3/1984 |
| JP | 59059221 | 4/1984 |
| JP | 59087004 | 5/1984 |
| JP | 59-211459 | 11/1984 |
| JP | 59209608 | 11/1984 |
| JP | 59209609 | 11/1984 |
| JP | 59209610 | 11/1984 |
| JP | 60245623 | 12/1985 |
| JP | 61238319 | 10/1986 |
| JP | 62074406 | 4/1987 |
| JP | 62102815 | 5/1987 |
| JP | 62227423 | 10/1987 |
| JP | 63130661 | 6/1988 |
| JP | 01018404 | 1/1989 |
| JP | 01018405 | 1/1989 |
| JP | 05279447 | 10/1993 |
| JP | 8196626 | 8/1996 |
| JP | 2002 055076 | 2/2002 |
| WO | WO 89/02720 | 4/1989 |
| WO | WO 90/07575 | 7/1990 |
| WO | WO 92/13271 | 8/1992 |
| WO | WO 93/14185 | 7/1993 |
| WO | WO 93/14693 | 8/1993 |
| WO | WO 93/23744 | 11/1993 |

| WO | WO 94/08236 | 4/1994 |
| WO | WO 96/14026 | 5/1996 |
| WO | WO 96/25089 | 8/1996 |
| WO | WO 96/30431 | 10/1996 |
| WO | WO 97/01986 | 1/1997 |
| WO | WO 97/11067 | 3/1997 |
| WO | WO 99/56613 | 4/1999 |
| WO | WO 00/59373 | 10/2000 |
| WO | WO 00/74753 | 12/2000 |
| WO | WO 01/20019 | 3/2001 |
| WO | WO 02/053764 | 7/2002 |
| WO | WO 2005/045394 | 5/2005 |
| WO | WO 2006/018425 | 2/2006 |
| WO | WO 2007/114943 | 10/2007 |

OTHER PUBLICATIONS

Dixon, et al. 2002. Characterization in vitro and in vivo of the oxygen dependence of an enzyme/polymer biosensor for monitoring brain glucose. Journal of Neuroscience Methods 119:135-142.

Gilligan, B. C.; Shults, M.; Rhodes, R. K.; Jacobs, P. G.; Brauker, J. H.; Pintar, T. J.; Updike, S. J. 2004, Feasibility of continuous long-term glucose monitoring from a subcutaneous glucose sensor in humans. Diabetes Technol Ther 6:378-386.

Heller, A. 1999. Implanted electrochemical glucose sensors for the management of diabetes. Annu Rev Biomed Eng 1:153-175.

Hitchman, M. L. 1978. Measurement of Dissolved Oxygen. In Elving, et al. (Eds.). Chemical Analysis, vol. 49, Chap. 3, pp. 34-49, 59-123. New York: John Wiley & Sons.

Kang, S. K.; Jeong, R. A.; Park, S.; Chung, T. D.; Park, S.; Kim, H. C. 2003. In vitro and short-term in vivo characteristics of a Kel-F thin film modified glucose sensor. Anal Sci 19:1481-1486.

Leypoldt, et al. 1984. Model of a two-substrate enzyme electrode for glucose. Anal. Chem. 56:2896-2904.

Mancy, et al. 1962. A galvanic cell oxygen analyzer. Journal of Electroanalytical Chemistry 4:65-92.

Matsumoto, et al. 2001. A long-term lifetime amperometric glucose sensor with a perfluorocarbon polymer coating. Biosens Bioelectron 16:271-276.

Myler, et al. 2002. Ultra-thin-polysiloxane-film-composite membranes for the optimisation of amperometric oxidase enzyme electrodes. Biosens Bioelectron 17:35-43.

Quinn, C. A.; Connor, R. E.; Heller, A. 1997. Biocompatible, glucose-permeable hydrogel for in situ coating of implantable biosensors. Biomaterials 18:1665-1670.

Rhodes, et al. 1994. Prediction of pocket-portable and implantable glucose enzyme electrode performance from combined species permeability and digital simulation analysis. Analytical Chemistry 66(9):1520-1529.

Schuler, R.; Wittkampf, M.; Chemniti, G. C. 1999. Modified gas-permeable silicone rubber membranes for covalent immobilisation of enzymes and their use in biosensor development. Analyst 124:1181-1184.

Thomé-Duret, et al. 1996. Modification of the sensitivity of glucose sensor implanted into subcutaneous tissue. Diabetes Metabolism 22:174-178.

Updike, et al. 1982. Implanting the glucose enzyme electrode: Problems, progress, and alternative solutions. Diabetes Care 5(3):207-212.

Ward et al. 2002. A new amperometric glucose microsensor: In vitro and short-term in vivo evaluation. Biosensors & Bioelectronics, 17:181-189.

Wientjes, K. J. C. 2000. Development of a glucose sensor for diabetic patients (Ph.D. Thesis).

Wilkins, et al. 1995. Integrated implantable device for long-term glucose monitoring. Biosens. Bioelectron 10:485-494.

Wilson, et al. 1992. Progress toward the development of an implantable sensor for glucose. Clin. Chem. 38(9):1613-1617.

Wu, et al. 1999. In situ electrochemical oxygen generation with an immunoisolation device. Ann. N.Y. Acad. Sci. 875:105-125.

Office Action dated Mar. 14, 2007 in U.S. Appl. No. 10/695,636.
Office Action dated May 22, 2006 in U.S. Appl. No. 10/695,636.
Office Action dated Dec. 6, 2005 in U.S. Appl. No. 10/695,636.

Wagner, et al. 1998. Continuous amperometric monitoring of glucose in a brittle diabetic chimpanzee with a miniature subcutaneous electrode. Proc. Natl. Acad. Sci. A, 95:6379-6382.

Office Action dated Apr. 1, 2007 in U.S. Appl. No. 10/896,639.
Office Action dated Aug. 22, 2006 in U.S. Appl. No. 10/896,639.
Office Action dated Apr. 6, 2006 in U.S. Appl. No. 10/896,639.
Office Action dated Sep. 23, 2005 in U.S. Appl. No. 10/896,639.
Office Action dated Oct. 4, 2006 in U.S. Appl. No. 11/334,876.
Office Action dated Sep. 25, 2007 in U.S. Appl. No. 11/334,876.
IPRP for PCT/US04/023454 filed Jul. 21, 2004.
ISR and WO for PCT/US07/03881 filed Feb. 14, 2007.

Armour et al. Dec. 1990. Application of Chronic Intravascular Blood Glucose Sensor in Dogs. Diabetes 39:1519-1526.

Bellucci et al. Jan. 1986. Electrochemical behaviour of graphite-epoxy composite materials (GECM) in aqueous salt solutions, Journal of Applied Electrochemistry, 16(1):15-22.

Bindra et al. 1991. Design and In Vitro Studies of a Needle-Type Glucose Senso for Subcutaneous Monitoring. Anal. Chem 63:1692-96.

Bobbioni-Harsch et al. 1993. Lifespan of subcutaneous glucose sensors and their performances during dynamic glycaemia changes in rats, J. Biomed. Eng. 15:457-463.

Brooks et al. "Development of an on-line glucose sensor for fermentation monitoring," Biosensors, 3:45-56 (1987/88).

Cass et al. "Ferrocene-mediated enzyme electrodes for amperometric determination of glucose," Anal. Chem., 36:667-71 (1984).

Davies, et al. 1992. Polymer membranes in clinical sensor applications. I. An overview of membrane function, Biomaterials, 13(14):971-978.

Heller, "Electrical wiring of redox enzymes,"Acc. Chem. Res., 23:128-134 (1990).

Heller, A. 1992. Electrical Connection of Enzyme Redox Centers to Electrodes. J. Phys. Chem. 96:3579-3587.

Hicks, 1985. In Situ Monitoring, Clinical Chemistry, 31(12):1931-1935.

Hu, et al. 1993. A needle-type enzyme-based lactate sensor for in vivo monitoring, Analytica Chimica Acta, 281:503-511.

Johnson et al. 1992. In vivo evaluation of an electroenzymatic glucose sensor implanted in subcutaneous tissue. Biosensors & Bioelectronics, 7:709-714.

Kawagoe et al. 1991. Enzyme-modified organic conducting salt microelectrode, Anal. Chem. 63:2961-2965.

Kerner et al. "The function of a hydrogen peroxide-detecting electroenzymatic glucose electrode is markedly impaired in human sub-cutaneous tissue and plasma," Biosensors & Bioelectronics, 8:473-482 (1993).

Maidan et al. 1992. Elimination of Electrooxidizable Interferent-Produced Currents in Amperometric Biosensors, Analytical Chemistry, 64:2889-2896.

Mastrototaro et al. "An electroenzymatic glucose sensor fabricated on a flexible substrate," Sensors and Actuators B, 5:139-44 (1991).

McKean, et al. Jul. 7, 1988. A Telemetry Instrumentation System for Chronically Implanted Glucose and Oxygen Sensors. Transactions on Biomedical Engineering 35:526-532.

Moatti-Sirat et al. 1992. Towards continuous glucose monitoring: in vivo evaluation of a miniaturized glucose sensor implanted for several days in rat subcutaneous tissue. Diabetologia 35:224-230.

Murphy, et al. 1992. Polymer membranes in clinical sensor applications. II. The design and fabrication of permselective hydrogels for electrochemical devices, Biomaterials, 13(14):979-990.

Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.

Pegoraro et al. 1995. Gas transport properties of siloxane polyurethanes, Journal of Applied Polymer Science, 57:421-429.

Pickup et al. "Implantable glucose sensors: choosing the appropriate sensor strategy," Biosensors, 3:335-346 (1987/88).

Pickup et al. "In vivo molecular sensing in diabetes mellitus: an implantable glucose sensor with direct electron transfer," Diabetologia, 32:213-217 (1989).

Pishko et al. "Amperometric glucose microelectrodes prepared through immobilization of glucose oxidase in redox hydrogels," Anal. Chem., 63:2268-72 (1991).

Poitout, et al. 1991. In Vitro and In Vivo Evaluation in Dogs of a Miniaturized Glucose Sensor, ASAIO Transactions, 37:M298-M300.

Reach et al. 1992. Can continuous glucose monitoring be used for the treatment of diabetes? Analytical Chemistry 64(5):381-386.

Rebrin et al. "Automated feedback control of subcutaneous glucose concentration in diabetic dogs," Diabetologia, 32:573-76 (1989).

Sakakida et al. 1993. Ferrocene-Mediated Needle Type Glucose Sensor Covered with Newly Designed Biocompatible Membran, Sensors and Actuators B 13-14:319-322.

Shaw et al. "In vitro testing of a simply constructed, highly stable glucose sensor suitable for implantation in diabetic patients," Biosensors & Bioelectronics, 6:401-406 (1991).

Shichiri et al. 1985. Needle-type Glucose Sensor for Wearable Artificial Endocrine Pancreas in Implantable Sensors 197-210.

Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.

Shichiri et al., 1989. Membrane Design for Extending the Long-Life of an Implantable Glucose Sensor. Diab. Nutr. Metab. 2:309-313.

Shults et al. 1994. A telemetry-instrumentation system for monitoring multiple subcutaneously implanted glucose sensors. IEEE Transactions on Biomedical Engineering 41(10):937-942.

Sokol et al. 1980, Immobilized-enzyme rate-determination method for glucose analysis, Clin. Chem. 26(1):89-92.

Sternberg et al. 1988. Study and Development of Multilayer Needle-type Enzyme-based Glucose Microsensors. Biosensors 4:27-40.

Takegami et al. 1992. Pervaporation of ethanol water mixtures using novel hydrophobic membranes containing polydimethylsiloxane, Journal of Membrance Science, 75(93-105).

Thompson et al., In Vivo Probes: Problems and Perspectives, Department of Chemistry, University of Toronto, Canada, pp. 255-261, 1986.

Turner and Pickup, "Diabetes mellitus: biosensors for research and management," *Biosensors*, 1:85-115 (1985).

Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons, pp. 117-137.

Velho et al. 1989. Strategies for calibrating a subcutaneous glucose sensor. Biomed Biochim Acta 48(11/12):957-964.

von Woedtke et al. 1989. In situ calibration of implanted electrochemical glucose sensors. Biomed Biochim. Acta 48(11/12):943-952.

IPRP for PCT/US07/03881 filed Feb. 14, 2007.

Office Action dated Jan. 23, 2009 in U.S. Appl. No. 11/404,417.

Office Action dated Oct. 5, 2007 in U.S. Appl. No. 10/896,639.

Aalders et al. 1991. Development of a wearable glucose sensor; studies in healthy volunteers and in diabetic patients. The International Journal of Artificial Organs 14(2):102-108.

Abe et al. 1992. Characterization of glucose microsensors for intracellular measurements. Alan. Chem. 64(18):2160-2163.

Abel et al. 1984. Experience with an implantable glucose sensor as a prerequisite of an artifical beta cell, Biomed. Biochim. Acta 43(5):577-584.

Abel et al. 2002. Biosensors for in vivo glucose measurement: can we cross the experimental stage. Biosens Bioelectron 17:1059-1070.

Alcock & Turner. 1994. Continuous Analyte Monitoring to Aid Clinical Practice. IEEE Engineering in Med. & Biol. Mag. 13:319-325.

American Heritage Dictionary, 4th Edition. 2000. Houghton Mifflin Company, p. 82.

Amin et al. 2003. Hypoglycemia prevalence in prepubertal children with type 1 diabetes on standard insulin regimen: Use of continuous glucose monitoring system. Diabetes Care 26(3):662-667.

Answers.com. "xenogenic." The American Heritage Stedman's Medical Dictionary. Houghton Mifflin Company, 2002. Answers.com Nov. 7, 2006 http://www.Answers.com/topic/xenogenic.

Atanasov et al. 1994. Biosensor for continuous glucose monitoring. Biotechnology and Bioengineering 43:262-266.

Atanasov et al. 1997. Implantation of a refillable glucose monitoring-telemetry device. Biosens Bioelectron 12:669-680.

Aussedat et al. 1997. A user-friendly method for calibrating a subcutaneous glucose sensor-based hypoglycaemic alarm. Biosensors & Bioelectronics 12(11):1061-1071.

Bailey et al. 2007. Reduction in hemoglobin A1c with real-time continuous glucose monitoring: results from a 12-week observational study. Diabetes Technology & Therapeutics 9(3):203-210.

Beach et al. 1999. Subminiature implantable potentiostat and modified commercial telemetry device for remote glucose monitoring. IEEE Transactions on Instrumentation and Measurement 48(6):1239-1245.

Bessman et al., Progress toward a glucose sensor for the artificial pancreas, Proceedings of a Workshop on Ion-Selective Microelectrodes, Jun. 4-5, 1973, Boston, MA, 189-197.

Biermann et al. 2008. How would patients behave if they were continually informed of their blood glucose levels? A simulation study using a "virtual" patient. Diab. Thechnol. & Therapeut., 10:178-187.

Bisenberger et al. 1995. A triple-step potential waveform at enzyme multisensors with thick-film gold electrodes for detection of glucose and sucrose. Sensors and Actuators, B 28:181-189.

Bland et al. 1990. A note on the use of the intraclass correlation coefficient in the evaluation of agreement between two methods of measurement. Comput. Biol. Med. 20(5):337-340.

Bode et al. 1999. Continuous glucose monitoring used to adjust diabetes therapy improves glycosylated hemoglobin: A pilot study. Diabetes Research and Clinical Practice 46:183-190.

Bode et al. 2000. Using the continuous glucose monitoring system to improve the management of type 1 diabetes. Diabetes Technology & Therapeutics, 2(Suppl 1):S43-48.

Bode, B. W. 2000. Clinical utility of the continuous glucose monitoring system. Diabetes Technol Ther, 2(Suppl 1):S35-41.

Boedeker Plastics, Inc. 2009. Polyethylene Specifications Data Sheet, http://www.boedeker.com/polye_p.htm [Aug. 19, 2009 3:36:33 PM].

Boland et al. 2001. Limitations of conventional methods of self-monitoring of blood glucose. Diabetes Care 24(11):1858-1862.

Bowman, L.; Meindl, J. D. 1986. The packaging of implantable integrated sensors. IEEE Trans Biomed Eng BME33(2):248-255.

Brauker et al. Jun. 27, 1996. Local Inflammatory Response Around Diffusion Chambers Containing Xenografts Transplantation 61(12):1671-1677.

Braunwald, 2008. Biomarkers in heart failure. *N. Engl. J. Med.*, 358: 2148-2159.

Bremer et al. 2001. Benchmark data from the literature for evaluation of new glucose sensing technologies. Diabetes Technology & Therapeutics 3(3):409-418.

Bruckel et al. 1989. In vivo measurement of subcutaneous glucose concentrations with an enzymatic glucose sensor and a wick method. Klin Wochenschr 67:491-495.

Cai et al. 2004. A wireless, remote query glucose biosensor based on a pH-sensitive polymer. Anal Chem 76(4):4038-4043.

Campanella et al. 1993. Biosensor for direct determination of glucose and lactate in undiluted biological fluids. Biosensors & Bioelectronics 8:307-314.

Candas et al (1994). "An adaptive plasma glucose controller basedon on a nonlinear insulin/glucose model." *IEEE Transactions on Biomedical Engineering*, 41(2): 116-124.

Cassidy et al., Apr. 1993. Novel electrochemical device for the detection of cholesterol or glucose, Analyst, 118:415-418.

Chase et al. 2001. Continuous subcutaneous glucose monitoring in children with type 1 diabetes. Pediatrics 107:222-226.

Chatterjee et al. 1997. Poly(ether Urethane) and poly(ether urethane urea) membranes with high $H_2S/CH_4$ selectivity, Journal of Membrane Science 135:99-106.

Ciba® Irgacure 2959 Photoinitiator Product Description, Ciba Specialty Chemicals Inc., Basel, Switzerland.

Claremont et al. 1986. Subcutaneous implantation of a ferrocene-mediated glucose sensor in pigs. Diabetologia 29:817-821.

Claremont et al. Jul. 1986. Potentially-impintable, ferrocene-mediated glucose sensor. J. Biomed. Eng. 8:272-274.

Clark et al., 1981. One-minute electrochemical enzymic assay for cholesterol in biological materials, Clin. Chem. 27(12):1978-1982.

Clark et al. 1987. Configurational cyclic voltammetry: increasing the specificity and reliablity of implanted electrodes, IEEE/Ninth Annual Conference of the Engineering in Medicine and Biology Society, pp. 0782-0783.

Clark et al. 1988. Long-term stability of electroenzymatic glucose sensors implanted in mice. Trans Am Soc Artif Intern Organs 34:259-265.

CLSI. Performance metrics for continuous interstitial glucose monitoring; approved guideline, CLSI document POCT05-A. Wayne, PA: Clinical and Laboratory Standards Institute: 2008 28(33), 72 pp.

Colangelo et al. 1967. Corrosion rate measurements in vivo, Journal of Biomedical Materials Research, 1:405-414.

Colowick et al. 1976. Methods in Enzymlology, vol. XLIV, Immobilized Enzymes. New York: Academic Press.

Cox et al. 1985. Accuracy of perceiving blood glucose in IDDM. Diabetes Care 8(6):529-536.

Csoregi et al., 1994. Design, characterization, and one-point in vivo calibration of a subcutaneously implanted glucose electrode. Anal Chem. 66(19):3131-3138.

Danielsson et al. 1988. Enzyme thermistors, Methods in Enzymology, 137:181-197.

Dassau et al., In silico evaluation platform for artifical pancreatic β-cell development—a dynamic simulator for closed loop control with hardware-in-the-loop, Diabetes Technology & Therapeutics, 11(3):1-8, 2009.

Davis et al. 1983. Bioelectrochemical fuel cell and sensor based on a quinoprotein, alcohol dehydrogenase. *Enzyme Microb. Technol.*, vol. 5, September, 383-388.

Direct 30/30® meter (Markwell Medical) (Catalog).

DuPont Dimension AR® (Catalog), 1998.

Durliat et al. 1976. Spectrophotometric and electrochemical determinations of L(+)-lactate in blood by use of lactate dehydrogenase from yeast, Clin. Chem. 22(11):1802-1805.

Edwards Lifesciences. Accuracy for your and your patients. Marketing materials, 4 pp. 2002.

El Degheidy et al. 1986. Optimization of an implantable coated wire glucose sensor. J. Biomed Eng. 8: 121-129.

El-Khatib et al. 2007. Adaptive closed-loop control provides blood-glucose regulation using dual subcutaneous insulin and glucagon infusion in diabetic swine, Journal of Diabetes Science and Technology, 1(2):181-192.

Ei-Sa'ad et al. 1990. Moisture Absorption by Epoxy Resins: the Reverse Thermal Effect. Journal of Materials Science 25:3577-3582.

Ernst et al. 2002. Reliable glucose monitoring through the use of microsystem technology. Anal. Bioanal. Chem. 373:758-761.

Fahy et al., An analysis: hyperglycemic intensive care patients need continuous glocuse monitoring—easier said than done, Journal of Diabetese Science and Technology, 2(2):201-204, Mar. 2008.

Fare et al. 1998. Functional characterization of a conducting polymer-based immunoassay system. Biosensors & Bioelectronics 13(3-4):459-470.

Feldman et al. 2003. A continuous glucose sensor based on wired enzyme technology—results from a 3-day trial in patients with type 1 diabetes. Diabetes Technol Ther 5(5):769-779.

Fischer et al. 1987. Assessment of subcutaneous glucose concentration: validation of the wick technique as a reference for implanted electrochemical sensors in normal and diabetic dogs, Diabetologia 30:940-945.

Fischer et al. 1989. Oxygen Tension at the Subcutaneous Implantation Site of Glucose Sensors. Biomed. Biochem 11/12:965-972.

Fischer et al. 1995. Hypoglycaemia-warning by means of subcutaneous electrochemical glucose sensors: an animal study, Horm. Metab. Rese. 27:53.

Freedman et al. 1991. Statistics, Second Edition, W.W. Norton & Company, p. 74.

Frohnauer et al. 2001. Graphical human insulin time-activity profiles using standardized definitions. Diabetes Technology & Therapeutics 3(3):419-429.

Frost et al. 2002. Implantable chemical sensors for real-time clinical monitoring: Progress and challenges. Current Opinion in Chemical Biology 6:633-641.

Gabbay et al. 2008. Optical coherence tomography-based continuous noninvasive glucose monitoring in patients with diabetes. Diab. Thechnol. & Therapeut., 10:188-193.

Ganesan et al., Gold layer-based dual crosslinking procedure of glucose oxidase with ferrocene monocarboxylic acid provides a stable biosensor, Analytical Biochemistry 343:188-191, 2005.

Ganesh et al., Evaluation of the VIA® blood chemistry monitor for glucose in healthy and diabetic volunteers, Journal of Diabetese Science and Technology, 2(2):182-193, Mar. 2008.

Gao et al. 1989. Determination of Interfacial parameters of cellulose acetate membrane materials by HPLC, *J. Liquid Chromatography*, VI. 12, n. 11, 2083-2092.

Garg et al. 2004. Improved Glucose Excursions Using an Implantable Real-Time continuous Glucose Sensor in Adults with Type I Diabetes. Diabetes Care 27:734-738.

Gerritsen et al. 1999. Performance of subcutaneously implanted glucose sensors for continuous monitoring. The Netherlands Journal of Medicine 54:167-179.

Gerritsen, M. 2000. Problems associated with subcutaneously implanted glucose sensors. Diabetes Care 23(2):143-145.

Gilligan et al. 1994. Evaluation of a subcutaneous glucose sensor out to 3 months in a dog model. Diabetes Care 17(8):882-887.

Godsland et al. 2001. Maximizing the Success Rate of Minimal Model Insulin Sensitivity Measurement in Humans: The Importance of Basal Glucose Levels. The Biochemical Society and the Medical Research Society, 1-9.

Gouda et al., Jul. 4, 2003. Thermal inactiviation of glucose oxidase, The Journal of Biological Chemistry, 278(27):24324-24333.

Gough et al. 2000. Immobilized glucose oxidase in implantable glucose sensor technology. Diabetes Technology & Therapeutics 2(3):377-380.

Gough et al. 2003. Frequency characterization of blood glucose dynamics. Annals of Biomedical Engineering 31:91-97.

Gross et al. 2000. Efficacy and reliability of the continuous glucose monitoring system. Diabetes Technology & Therapeutics, 2(Suppl 1):S19-26.

Gross et al. 2000. Performance evaluation of the MiniMed® continuous glucose monitoring system during patient home use. Diabetes Technology & Therapeutics 2(1):49-56.

Guerci et al., Clinical performance of CGMS in type 1 diabetic patents treated by continuous subcutaneous insulin infusion using insulin analogs, Diabetes Care, 26:582-589, 2003.

Guo et al., Modification of cellulose acetate ultrafiltration membrane by gamma ray radiation, Shuichuli Jishi Bianji Weiyuanhui, 23(6):315-318, 1998 (Abstract only).

Hall et al. 1998. Electrochemical oxidation of hydrogen peroxide at platinum electrodes. Part I: An adsorption-controlled mechanism. Electrochimica Acta, 43(5-6):579-588.

Hall et al. 1998. Electrochemical oxidation of hydrogen peroxide at platinum electrodes. Part II: Effect of potential. Electrochimica Acta 43(14-15):2015-2024.

Hall et al. 1999. Electrochemical oxidation of hydrogen peroxide at platinum electrodes. Part III: Effect of temperature. Electrochimica Acta, 44:2455-2462.

Hall et al. 1999. Electrochemical oxidation of hydrogen peroxide at platinum electrodes. Part IV: Phosphate buffer dependence. Electrochimica Acta, 44:4573-4582.

Hall et al. 2000. Electrochemical oxidation of hydrogen peroxide at platinum electrodes. Part V: Inhibition by chloride. Electrochimica Acta, 45:3573-3579.

Hamilton Syringe Selection Guide. 2006. Syringe Selection. www.hamiltoncompany.com.

Harrison et al. 1988. Characterization of perfluorosulfonic acid polymer coated enzyme electrodes and a miniaturized integrated potentiostat for glucose analysis in whole blood. Anal. Chem. 60:2002-2007.

Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," *Diabetes C.*

Heller, A. 2003. Plugging metal connectors into enzymes. Nat Biotechnol 21:631-2.

Hoel, Paul G. 1976. Elementary Statistics, Fourth Edition. John Wiley & Sons, Inc.. pp. 113-114.

Hrapovic et al. 2003. Picoamperometric detection of glucose at ultrasmall platinum-based biosensors: preparation and characterization. Anal Chem 75:3308-3315.

http://www.merriam-webster.com/dictionary, definition for "aberrant," Aug. 19, 2008, p. 1.

Huang et al. A 0.5mV passive telemetry IC for biomedical applications. Swiss Federal Institute of Technology. 4 pp.

Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum E.

Hunter et al. 2000. Minimally Invasive Glucose Sensor and Insulin Delivery System. MIT Home Automation and Healthcare Consortium. Progress Report No. 25.

Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Compl.

Jensen et al. 1997. Fast wave forms for pulsed electrochemical detection of glucose by incorporation of reductive desorption of oxidation products. Analytical Chemistry 69(9):1776-1781.

Jeutter, D. C. 1982. A transcutaneous implanted battery recharging and biotelemeter power switching system. IEEE Trans Biomed Eng 29:314-321.

Johnson (1991). "Reproducible electrodeposition of biomolecules for the fabrication of miniature electroenzymatic biosensors," *Sensors and Actuators B*, 5:85-89.

Jovanovic, L. 2000. The role of continuous glucose monitoring in gestational diabetes mellitus. Diabetes Technology & Therapeutics, 2 Suppl 1, S67-71.

Kacaniklic May-Jun. 1994. Electroanalysis, 6(5-6):381-390.

Kamath et al. Calibration of a continuous glucose monitor: effect of glucose rate of change, Eighth Annual Diabetes Technology Meeting, Nov. 13-15, 2008, p. A88.

Kaufman. 2000. Role of the continuous glucose monitoring system in pediatric patients. Diabetes Technology & Therapeutics 2(1):S-49-S-52.

Kaufman et al. 2001. A pilot study of the continuous glucose monitoring system. Diabetes Care 24(12):2030-2034.

Keedy et al. 1991. Determination of urate in undiluted whole blood by enzyme electrode. *Biosensors & Bioelectronics*, 6: 491-499.

Kerner et al. 1988. A potentially implantable enzyme electrode for amperometric measurement of glucose, Horm Metab Res Suppl. 20:8-13.

Klueh et al. 2003. Use of Vascular Endothelia Cell Growth Factor Gene Transfer to Enhance Implantable Sensor Function in Vivo, Biosensor Function and Vegf-Gene Transfer, pp. 1072-1086.

Ko, Wen H. 1985. Implantable Sensors for Closed-Loop Prosthetic Systems, Futura Pub. Co., Inc., Mt. Kisco, NY, Chapter 15:197-210.

Kondo et al. 1982. A miniature glucose sensor, implantable in the blood stream. Diabetes Care. 5(3):218-221.

Koschinsky et al. 1988. New approach to technical and clinical evaluation of devices for self-monitoring of blood glucose. Diabetes Care 11(8): 619-619.

Koschinsky et al. 2001. Sensors for glucose monitoring: Technical and clinical aspects. Diabetes Metab. Res. Rev. 17:113-123.

Kost et al. 1985. Glucose-sensitive membranes containing glucose oxidase: activitiy, swelling, and permeability studies, Journal of Biomedical Materials Research 19:1117-1133.

Koudelka et al. 1989. In vivo response of microfabricated glucose sensors to glycemia changes in normal rats. Biomed Biochim Acta 48(11-12):953-956.

Koudelka et al. 1991. In-vivo behaviour of hypodermically implanted microfabricated glucose sensors. Biosensors & Bioelectronics 6:31-36.

Kraver et al. 2001. A mixed-signal sensor interface microinstrument. Sensors and Actuators A 91:266-277.

Kruger et al. 2000. Psychological motivation and patient education: A role for continuous glucose monitoring. Diabetes Technology & Therapeutics, 2(Suppl 1):S93-97.

Kulys et al., 1994. Carbon-paste biosensors array for long-term glucose measurement, Biosensors& Beioelectronics, 9:491-500.

Kunjan et al., Automated blood sampling and glocuse sensing in critical care settings, Journal of Diabetes Science and Technology 2(3):194-200, Mar. 2008.

Kurtz et al. 2005. Recommendations for blood pressure measurement in humans and experimental animals, Part 2: Blood pressure measurement in experimental animals, A statement for professionals from the subcommittee of professional and public education of.

Ladd et al., Structure Determination by X-ray Crystallography, 3rd ed. Plenum, 1996, Ch. 1, pp. xxi-xxiv and 1-58.

Lehmann et al. May 1994. Retrospective valication of a physiological model of glucose-iunsulin interaaction in tyhpe 1 diabetes mellitus, Med. Eng. Phys. 16:193-202.

Lerner et al. 1984. An implantable electrochemical glucose sensor. Ann. N. Y. Acad. Sci. 428:263-278.

Lewandowski et al. 1988. Evaluation of a miniature blood glucose sensor. Trans Am Soc Artif Intern Organs 34:255-258.

Linke et al. 1994. Amperometric biosensor for in vivo glucose sensing based on glucose oxidase immobilized in a redox hydrogel. Biosensors & Bioelectronics 9:151-158.

Lowe, 1984. Biosensors, Trends in Biotechnology, 2(3):59-65.

Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.

Lyandres et al. (2008). Progress toward an in vivo surface-enhanced raman spectroscopy glucose sensor. *Diabetes Technology & Therapeutics*, 10(4): 257-265.

Makale et al. 2003. Tissue window chamber system for validation of implanted oxygen sensors. Am. J. Physiol. Heart Circ. Physiol. 284:H2288-2294.

Malin et al. 1999. Noninvasive Prediction of Glucose by Near-Infrared Diffuse Reflectance Spectroscopy. Clinical Chemistry 45:9, 1651-1658.

Maran et al. 2002. Continuous subcutaneous glucose monitoring in diabetic patients: A multicenter analysis. Diabetes Care 25(2):347-352.

March, W. F. 2002. Dealing with the delay. Diabetes Technol Ther 4(1):49-50.

Marena et al. 1993. The artifical endocrine pancreas in clinical practice and research. Panminerva Medica 35(2):67-74.

Mascini et al. 1989. Glucose electrochemical probe with extended linearity for whole blood. *J Pharm Biomed Anal* 7(12): 1507-1512.

Mastrototaro, J. J. 2000. The MiniMed continuous glucose monitoring system. Diabetes Technol Ther 2(Suppl 1):S13-8.

Mastrototaro et al. 2003. Reproducibility of the continuous glucose monitoring system matches previous reports and the intended use of the product. Diabetes Care 26:256; author reply p. 257.

Matsumoto et al. 1998. A micro-planar amperometeric glucose sensor unsusceptible to interference species. Sensors and Actuators B 49:68-72.

Matthews et al. 1988. An amperometric needle-type glucose sensor testing in rats and man. Diabetic Medicine 5:248-252.

Mazze et al. 2008. Characterizing glucose exposure for individuals with normal glucose tolerance using continuous glucose monitoring and ambulatory glucose profile analysis. Diab. Thechnol. & Therapeut., 10:149-159.

McCartney et al. 2001. Near-infrared fluorescence lifetime assay for serum glucose based on allophycocyanin-labeled concanavalin A. Anal Biochem 292:216-221.

McGrath et al. 1995. The use of differential measurements with a glucose biosensor for interference compensation during glucose determinations by flow injection analysis. Biosens Bioelectron 10:937-943.

Memoli et al. 2002. A comparison between different immobilised glucoseoxidase-based electrodes. J Pharm Biomed Anal 29:1045-1052.

Merriam-Webster Online Dictionary. Definition of "acceleration". http://www.merriam-webster.com/dictionary/Acceleration Jan. 11, 2010.

Merriam-Webster Online Dictionary. Definition of "system". http://www.merriam-webster.com/dictionary/System Jan. 11, 2010.

Merriam-Webster Online Dictionary. The term "nominal." http://www.m-w.com/dictionary/nominal.

Meyerhoff et al. 1992. On line continuous monitoring of subcutaneous tissue glucose in men by combining portable glucosensor with microdialysis. Diabetologia 35:1087-1092.

Moatti-Sirat et al. 1992. Evaluating in vitro and in vivo the interference of ascorbate and acetaminophen on glucose detection by a needle-type glucose sensor, Biosensors & Bioelectronics 7:345-352.

Moatti-Sirat et al., Reduction of acetaminophen interference in glucose sensors by a composite Nafion membrane: demonstration in rats and man, Diabetologia 37(6):610-616, Jun. 1994.

Morff et al. 1990. Microfabrication of reproducible, economical, electroenzymatic glucose sensors, Annual International Conference of the IEEE Engineering in Medicine and Biology Society, 12(2):0483-0484.

Mosbach et al. 1975. Determination of heat changes in the proximity of immobilized enzymes with an enzyme termistor and its use for the assay of metobolites, Biochim. Biophys. Acta. (Enzymology), 403:256-265.

Motonaka et al. 1993. Determination of cholesteral and cholesteral ester with novel enzyme microsensors, Anal. Chem. 65:3258-3261.

Muslu. 1991. Trickling filter performance. Apllied Biochemistry and Biotechnology 37:211-224.

Nafion® 117 Solution Product Description, Product No. 70160, Sigma-Aldrich Corp., St. Louis, MO.

Ohara et al. 1994. "Wired" enzyme electrodes for amperometric determination of glucose or lactate in the presence of interfering substances. Anal Chem 66:2451-2457.

Okuda et al. 1971. Mutarotase effect on micro determinations of D-glucose and its anomers with β-D-glucose oxidase. Anal Biochem 43:312-315.

Oxford English Dictionary Online. Definition of "impending". http://www.askoxford.com/results/?view=dev dict&field-12668446 Impending&branch= Jan. 11, 2010.

Palmisano et al. 2000. Simultaneous monitoring of glucose and lactate by an interference and cross-talk free dual electrode amperometric biosensor based on electropolymerized thin films. Biosensors & Bioelectronics 15:531-539.

Park et al. 2002. Gas separation properties of polysiloxane/polyether mixed soft segment urethane urea membranes, *J. Membrane Science*, 204: 257-269.

Patel et al. 2003. Amperometric glucose sensors based on ferrocene containing polymeric electron transfer systems—a preliminary report. Biosens Bioelectron 18:1073-6.

Peacock et al. 2008. Cardiac troponin and outcome in acute heart failure. N. Engl. J. Med., 358: 2117-2126.

Pfeiffer, E.F. 1990. The glucose sensor: the missing link in diabetes therapy, Horm Metab Res Suppl. 24:154-164.

Pfeiffer et al. 1992. On line continuous monitoring of subcutaneous tissue glucose is feasible by combining portable glucosensor with microdialysis. Horm. Metab. Res. 25:121-124.

Pichert et al. 2000. Issues for the coming age of continuous glucose monitoring Diabetes Educ 26(6):969-980.

Pickup et al. 1989. Potentially-implantable, amperometric glucose sensors with mediated electron transfer: improving the operating stability. Biosensors 4:109-119.

Pickup et al. 1993. Developing glucose sensors for in vivo use. Elsevier Science Publishers Ltd (UK), TIBTECH vol. 11: 285-291.

Pinner et al., Cross-linking of cellulose acetate by ionizing radiation, Nature, vol. 184, 1303-1304, Oct. 24, 1959.

Pitzer et al. 2001. Detection of hypoglycemia with the GlucoWatch biographer. Diabetes Care 24(5):881-885.

Poitout et al. 1993. A glucose monitoring system for on line estimation in man of blood glucose concentration using a miniaturized glucose sensor implanted in the subcutaneous tissue and a wearable control unit. Diabetologia 36:658-663.

Poitout et al. 1994. Development of a glucose sensor for glucose monitoring in man: the disposable implant concept. Clinical Materials 15:241-246.

Postlethwaite et al. 1996. Interdigitated array electrode as an alternative to the rotated ring-disk electrode for determination of the reaction products of dioxygen reduction. Analytical Chemistry 68:2951-2958.

Prabhu et al. 1981. Electrochemical studies of hydrogen peroxide at a platinum disc electrode, Electrochimica Acta 26(6):725-729.

Quinn et al. 1995. Kinetics of glucose delivery to subcutaneous tissue in rats measured with 0.3-mm amperometric microsensors. The American Physiological Society E155-E161.

Rabah et al., 1991. Electrochemical wear of graphite anodes during electrolysis of brine, Carbon, 29(2):165-171.

Reach et al. 1986. A Method for Evaluating in vivo the Functional Characteristics of Glucose Sensors. Biosensors 2:211-220.

Reach, G. 2001. Which threshold to detect hypoglycemia? Value of receiver-operator curve analysis to find a compromise between sensitivity and specificity. Diabetes Care 24(5):803-804.

Reach, Gerard. 2001. Letters to the Editor Re: Diabetes Technology & Therapeutics, 2000;2:49-56. Diabetes Technology & Therapeutics 3(1):129-130.

Rebrin et al. 1992. Subcutaenous glucose monitoring by means of electrochemical sensors: fiction or reality? J. Biomed. Eng. 14:33-40.

Reusch. 2004. Chemical Reactivity. Organometallic Compounds. Virtual Textbook of Organic Chem. pp. 1-16, http://www.cem.msu.edu/~reusch/VirtualText/orgmetal.htm.

Rigla et al. 2008. Real-time continuous glucose monitoring together with telemedical assitance improves glycemic control and glucose stability in pump-treated patients. Diab. Thechnol. & Therapeut., 10:194-199.

Rivers et al., Central venous oxygen saturation monitoring in the critically ill patient, Current Opinion in Critical Care, 7:204-211, 2001.

Sakakida et al. 1992. Development of Ferrocene-Mediated Needle-Type Glucose Sensor as a Measure of True Subcutaneous Tissue Glucose Concentrations. Artif. Organs Today 2(2):145-158.

Salardi et al. 2002. The glucose area under the profiles obtained with continuous glucose monitoring system relationships with HbA1c in pediatric type 1 diabetic patients. Diabetes Care 25(10):1840-1844.

San Diego Plastics, Inc. 2009. Polyethylene Data Sheet, http://www.sdplastics.com/polyeth.html.

Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.

Sansen et al. 1990. A smart sensor for the voltammetric measurement of oxygen or glucose concentrations. Sensors and Actuators B 1:298-302.

Schmidt et al. 1993. Glucose concentration in subcutaneous extracellular space. Diabetes Care 16(5):695-700.

Schmidtke et al., Measurement and modeling of the transient difference between blood and subcutaneous glucose concentrations in the rat after injection of insulin. *Proc Natl Acad Sci U S A* 1998, 95, 294-299.

Schoemaker et al. 2003. The SCGM1 system: Subcutaneous continuous glucose monitoring based on microdialysis technique. Diabetes Technology & Therapeutics 5(4):599-608.

Schoonen et al. 1990 Development of a potentially wearable glucose sensor for patients with diabetes mellitus: design and in-vitro evaluation. Biosensors & Bioelectronics 5:37-46.

Service et al. 1970. Mean amplitude of glycemic excursions, a measure of diabetic instability. Diabetes, 19: 644-655.

Service et al. 1987. Measurements of glucose control. Diabetes Care, 10: 225-237.

Service, R. F. 2002. Can sensors make a home in the body? Science 297:962-3.

Sharkawy et al. 1996. Engineering the tissue which encapsulates subcutaneous implants. I. Diffusion properties, J Biomed Mater Res, 37:401-412.

Shichiri et al. 1982. Wearable artificial endocrine pancrease with needle-type glucose sensor. Lancet 2:1129-1131.

Shichiri et al. 1983. Glycaemic Control in Pancreatectomized Dogs with a Wearable Artificial Endocrine Pancreas. Diabetologia 24:179-184.

Skyler, J. S. 2000. The economic burden of diabetes and the benefits of improved glycemic control: The potential role of a continuous glucose monitoring system. Diabetes Technology & Therapeutics 2 Suppl 1:S7-12.

Slater-Maclean et al. 2008. Accuracy of glycemic measurements in the critically ill. Diab. Thechnol. & Therapeut., 10:169-177.

Sriyudthsak et al. 1996. Enzyme-epoxy membrane based glucose analyzing system and medical applications. Biosens Bioelectron 11:735-742.

Steil et al. 2003. Determination of plasma glucose during rapid glucose excursions with a subcutaneous glucose sensor. Diabetes Technology & Therapeutics 5(1):27-31.

Stern et al., 1957. Electrochemical polarization: 1. A theoretical analysis of the shape of polarization curves, Journal of the Electrochemical Society, 104(1):56-63.

Sumino T. et al. 1998. Preliminary study of continuous glucose monitoring with a microdialysis technique. Proceedings of the IEEE, 20(4):1775-1778.

Tanenberg et al. 2000. Continuous glucose monitoring system: A new approach to the diagnosis of diabetic gastroparesis. Diabetes Technology & Therapeutics, 2 Suppl 1:S73-80.

Tatsuma et al. 1991. Oxidase/peroxidase bilayer-modified electrodes as sensors for lactate, pyruvate, cholesteral and uric acid, Analytica Chimica Acta, 242:85-89.

Thome et al. 1995. -Abstract—Can the decrease in subcutaneous glucose concentration precede the decrease in blood glucose level? Proposition for a push-pull kinetics hypothesis, Horm. Metab. Res. 27:53.

Thomé-Duret et al. 1996. Modification of the sensitivity of glucose sensor implanted into subcutaneous tissue. Diabetes Metabolism, 22:174-178.

Thomé-Duret et al. 1998. Continuous glucose monitoring in the free-moving rat. Metabolism, 47:799-803.

Tierney et al. 2000. Effect of acetaminophen on the accuracy of glucose measurements obtained with the GlucoWatch biographer. Diabetes Technol Ther 2:199-207.

Tierney et al. 2000. The GlucoWatch® biographer: A frequent, automatic and noninvasive glucose monitor. Ann. Med. 32:632-641.

Torjman et al., Glucose monitoring in acute care: technologies on the horizon, Journal of Deabetes Science and Technology, 2(2):178-181, Mar. 2008.

Trecroci, D. 2002. A Glimpse into the Future—Continuous Monitoring of Glucose with a Microfiber. Diabetes Interview 42-43.

Tse and Gough. 1987. Time-Dependent Inactivation of Immobilized Glucose Oxidase and Catalase. Biotechnol. Bioeng. 29:705-713.

Turner et al. 1984. Carbon Monoxide: Acceptor Oxidoreductase from Pseudomonas Thermocarboxydovorans Strain C2 and its use in a Carbon Monoxide Sensor. Analytica Chimica Acta, 163: 161-174.

Unger et al. 2004. Glucose control in the hospitalized patient. Emerg Med 36(9):12-18.

Updike et al. 1967. The enzyme electrode. Nature, 214:986-988.

Updike et al. 1988. Laboratory Evaluation of New Reusable Blood Glucose Sensor. Diabetes Care, 11:801-807.

Updike et al. 1994. Enzymatic glucose sensor: Improved long-term performance in vitro and in vivo. ASAIO Journal, 40(2):157-163.

Updike et al. 2000. A subcutaneous glucose sensor with improved longevity, dynamic range, and stability of calibration. Diabetes Care 23(2):208-214.

Utah Medical Products Inc., Blood Pressure Tranducers product specifications. 6 pp. 2003-2006, 2003.

Vadgama, P. Nov. 1981. Enzyme electrodes as practical biosensors. Journal of Medical Engineering & Technology 5(6):293-298.

Vadgama. 1988. Diffusion limited enzyme electrodes. NATO ASI Series: Series C, Math and Phys. Sci. 226:359-377.

Van den Berghe 2004. Tight blood glucose control with insulin in "real-life" intensive care. Mayo Clin Proc 79(8):977-978.

Velho et al. 1989. In vitro and in vivo stability of electrode potentials in needle-type glucose sensors. Influence of needle material. Diabetes 38:164-171.

Wang et al. 1994. Highly Selective Membrane-Free, Mediator-Free Glucose Biosensor. Anal. Chem. 66:3600-3603.

Wang et al. 1997. Improved ruggedness for membrane-based amperometric sensors using a pulsed amperometric method. Anal Chem 69:4482-4489.

Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.

Ward et al. 2000. Rise in background current over time in a subcutaneous glucose sensor in the rabbit: Relevance to calibration and accuracy. Biosensors & Bioelectronics, 15:53-61.

Wikipedia 2006. "Intravenous therapy," http://en.wikipedia.org/wiki/Intravenous_therapy, Aug. 15, 2006, 6 pp.

Wiley Electrical and Electronics Engineering Dictionary. 2004. John Wiley & Sons, Inc. pp. 141, 142, 548, 549.

Wilkins et al. 1988. The coated wire electrode glucose sensor, Horm Metab Res Suppl., 20:50-55.

Wilkins et al. 1995. Integrated implantable device for long-term glucose monitoring. Biosens. Bioelectron 10:485-494.

Wilson et al. 2000. Enzyme-based biosensors for in vivo measurements. Chem. Rev., 100:2693-2704.

Wood, W. et al. Mar. 1990. Hermetic Sealing with Epoxy. Mechanical Engineering 1-3.

Woodward. 1982. How Fibroblasts and Giant Cells Encapsulate Implants: Considerations in Design of Glucose Sensor. Diabetes Care 5:278-281.

Worsley et al., Measurement of glucose in blood with a phenylboronic acid optical sensor, Journal of Diabetes Science and Technology, 2(2):213-220, Mar. 2008.

Wright et al., Bioelectrochemical dehalogenations via direct electrochemistry of poly(ethylene oxide)-modified myoglobin, Electrochemistry Communications 1 (1999) 603-611.

Yamasaki, Yoshimitsu. Sep. 1984. The development of a needle-type glucose sensor for wearable artificial endocrine pancreas. Medical Journal of Osaka University 35(1-2):25-34.

Yamasaki et al. 1989. Direct measurement of whole blood glucose by a needle-type sensor. Clinica Chimica Acta. 93:93-98.

Yang et al (1996). "A glucose biosensor based on an oxygen electrode: In-vitro performances in a model buffer solution and in blood plasma," Biomedical Instrumentation & Technology, 30:55-61.

Yang et al. 1998. Development of needle-type glucose sensor with high selectivity. Science and Actuators B 46:249-256.

Yang, et al. 2004. A Comparison of Physical Properties and Fuel Cell Performance of Nafion and Zirconium Phosphate/Nafion Composite Membranes. Journal of Membrane Science 237:145-161.

Ye et al. 1993. High Current Density 'Wired' Quinoprotein Glucose Dehydrogenase Electrode. Anal. Chem. 65:238-241.

Zamzow et al. Development and evaluation of a wearable blood glucose monitor. pp. M588-M591, 1990.

Zethelius et al. 2008. Use of multiple biomarkers to improve the prediction of death from cardiovascular causes. N. Engl. J. Med., 358: 2107-2116.

Zhang et al (1993). Electrochemical oxidation of $H_2O_2$ on Pt and Pt + IR electrodes in physiological buffer and its applicability to $H_2O_2$-based biosensors. *J. Electroanal. Chem.*, 345:253-271.

Zhang et al. 1993. in vitro and in vivo evaluation of oxygen effects on a glucose oxidase based implantable glucose sensor. Analytica Chimica Acta, 281:513-520.

Zhang et al. 1994. Elimination of the acetaminophen interference in an implantable glucose sensor. Analytical Chemistry 66(7):1183-1188.

Zhu et al. (1994). "Fabrication and characterization of glucose sensors based on a microarray $H_2O_2$ electrode." *Biosensors & Bioelectronics*, 9: 295-300.

Zhu et al. 2002 Planar amperometric glucose sensor based on glucose oxidase immobilized by chitosan film on prussian blue layer. Sensors, 2:127-136.

Office Action dated Sep. 24, 2003 in U.S. Appl. No. 09/916,711.
Office Action dated Feb. 11, 2004 in U.S. Appl. No. 09/916,711.
Office Action dated Jul. 23, 2004 in U.S. Appl. No. 09/916,711.
Office Action dated Dec. 23, 2004 in U.S. Appl. No. 09/916,711.
Office Action dated Jul. 1, 2005 in U.S. Appl. No. 09/916,711.
Office Action dated Feb. 14, 2006 in U.S. Appl. No. 09/916,711.
Office Action dated Sep. 5, 2006 in U.S. Appl. No. 09/916,711.
Office Action dated Feb. 17, 2004 in U.S. Appl. No. 10/153,356.
Office Action dated Aug. 12, 2004 in U.S. Appl. No. 10/153,356.
Office Action dated Mar. 15, 2005 in U.S. Appl. No. 10/153,356.
Office Action dated Oct. 6, 2005 in U.S. Appl. No. 10/153,356.
Office Action dated Mar. 10, 2006 in U.S. Appl. No. 10/153,356.
Office Action dated Aug. 29, 2006 in U.S. Appl. No. 10/153,356.
Office Action dated Mar. 7, 2007 in U.S. Appl. No. 10/153,356.

Office Action dated Jul. 23, 2009 in U.S. Appl. No. 11/404,481.
Office Action dated Dec. 10, 2008 in U.S. Appl. No. 11/280,672.
Office Action dated Jun. 2, 2009 in U.S. Appl. No. 11/280,672.
Office Action dated Oct. 29, 2009 in U.S. Appl. No. 11/280,672.
Office Action dated Sep. 12, 2008 in U.S. Appl. No. 10/991,353.
Office Action dated Mar. 4, 2009 in U.S. Appl. No. 10/991,353.
Office Action dated Jul. 31, 2009 in U.S. Appl. No. 10/991,353.
Office Action dated Jan. 22, 2009 in U.S. Appl. No. 11/692,154.
Office Action dated Jul. 8, 2009 in U.S. Appl. No. 11/692,154.
Office Action dated Jul. 30, 2009 in U.S. Appl. No. 10/838,658.
Office Action dated Dec. 24, 2008 in U.S. Appl. No. 10/885,476.
Office Action dated Jun. 23, 2009 in U.S. Appl. No. 10/885,476.
Office Action dated May 5, 2008 in U.S. Appl. No. 11/077,713.
Office Action dated Feb. 10, 2009 in U.S. Appl. No. 11/077,713.
Office Action dated Sep. 2, 2009 in U.S. Appl. No. 11/077,713.
Office Action dated Jun. 27, 2008 in U.S. Appl. No. 11/077,693.
Office Action dated Dec. 26, 2008 in U.S. Appl. No. 11/077,693.
Office Action dated Sep. 4, 2009 in U.S. Appl. No. 11/077,693.
Office Action dated Jan. 10, 2008 in U.S. Appl. No. 11/077,714.
Office Action dated Jun. 22, 2009 in U.S. Appl. No. 11/360,262.
Office Action dated Jul. 26, 2007 in U.S. Appl. No. 11/411,656.
Office Action dated Jun. 26, 2008 in U.S. Appl. No. 11/335,879.
Office Action dated Jan. 13, 2009 in U.S. Appl. No. 11/335,879.
Office Action dated Jun. 16, 2009 in U.S. Appl. No. 11/335,879.

* cited by examiner

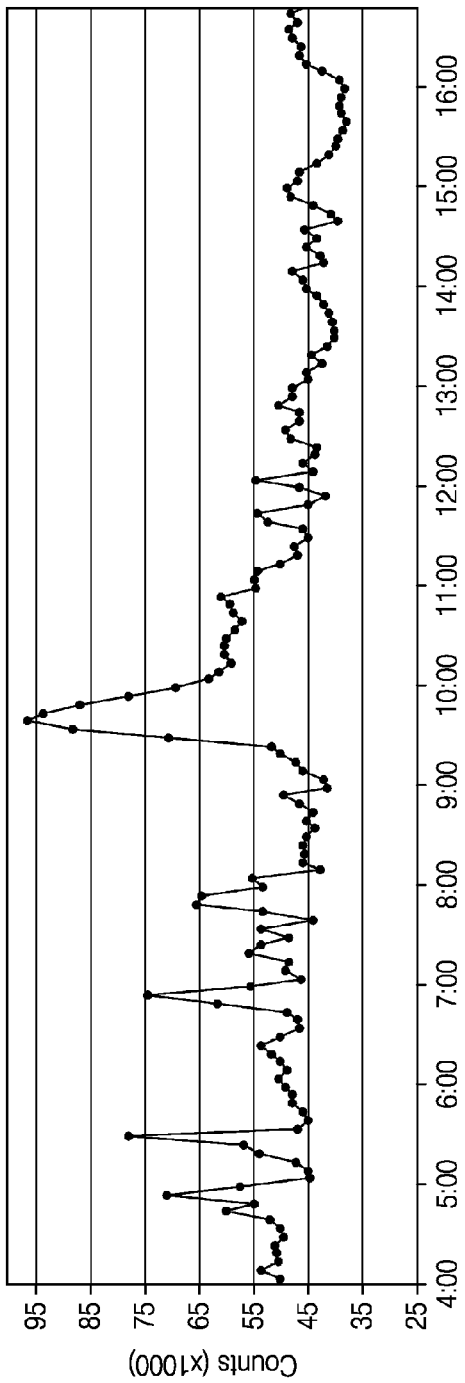
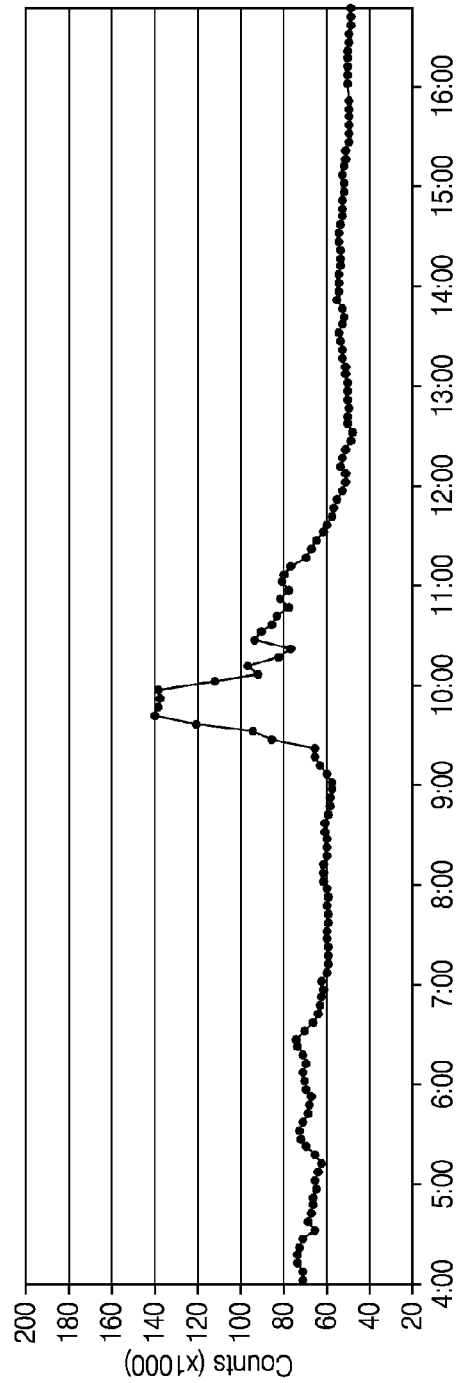
FIG. 10B
FIG. 10C

ANALYTE SENSOR

CROSS-REFERENCE TO RELATED APPLICATIONS

This application is a continuation-in-part of U.S. patent application Ser. No. 11/404,417, filed Apr. 14, 2006 now U.S. Pat. No. 7,613,491; and this application is a continuation-in-part of U.S. patent application Ser. No. 10/896,639, filed Jul. 21, 2004 now U.S. Pat. No. 7,379,765, which claims the benefit of U.S. Provisional Application No. 60/490,009, filed Jul. 25, 2003. Each of the aforementioned applications is incorporated by reference herein in its entirety, and each is hereby expressly made a part of this specification.

FIELD OF THE INVENTION

The present invention relates generally to membranes utilized with implantable devices, such as devices for the detection of analyte concentrations in a biological sample.

BACKGROUND OF THE INVENTION

One of the most heavily investigated analyte sensing devices is the implantable glucose device for detecting glucose levels in hosts with diabetes. Despite the increasing number of individuals diagnosed with diabetes and recent advances in the field of implantable glucose monitoring devices, currently used devices are unable to provide data safely and reliably for certain periods of time. See Moatti-Sirat et al., *Diabetologia*, 35:224-30 (1992). There are two commonly used types of subcutaneously implantable glucose sensing devices. These types include those that are implanted transcutaneously and those that are wholly implanted.

SUMMARY OF THE INVENTION

In a first aspect, an implantable analyte sensor is provided, comprising an electroactive surface configured for insertion into a host's body; and a membrane system comprising a cell impermeable domain disposed between the electroactive surface and the host's body when implanted; wherein the cell impermeable domain comprises a silicone material configured to allow transport of an analyte therethrough.

In an embodiment of the first aspect, the membrane system comprises an enzyme domain positioned between the electroactive surface and the cell impermeable domain, wherein the enzyme domain comprises an enzyme.

In an embodiment of the first aspect, the enzyme domain comprises a silicone material.

In an embodiment of the first aspect, the enzyme domain comprises glucose oxidase.

In an embodiment of the first aspect, the membrane system comprises a diffusion resistance domain.

In an embodiment of the first aspect, the diffusion resistance domain is positioned between the electroactive surface and the cell impermeable domain.

In an embodiment of the first aspect, the cell impermeable domain and the diffusion resistance domain comprise a unitary layer configured to control flux of the analyte therethrough.

In an embodiment of the first aspect, an analyte permeability of the cell impermeable domain is greater than an analyte permeability of the diffusion resistance domain.

In an embodiment of the first aspect, the diffusion resistance domain comprises a silicone material configured to control flux of the analyte therethrough.

In an embodiment of the first aspect, the cell impermeable domain exhibits an oxygen to analyte permeability ratio of at least about 50:1.

In an embodiment of the first aspect, the cell impermeable domain exhibits an oxygen to analyte permeability ratio of at least about 200:1.

In an embodiment of the first aspect, the silicone material comprises a blend of a silicone elastomer and a hydrophilic copolymer.

In an embodiment of the first aspect, the hydrophilic copolymer comprises hydroxy substituents.

In an embodiment of the first aspect, the hydrophilic copolymer comprises a poly(ethylene oxide)-poly(propylene oxide) copolymer.

In an embodiment of the first aspect, the hydrophilic copolymer comprises a poly(ethylene oxide)-poly(propylene oxide)-poly(ethylene oxide) triblock polymer.

In an embodiment of the first aspect, the hydrophilic copolymer comprises a PLURONIC® polymer.

In an embodiment of the first aspect, at least a portion of the hydrophilic copolymer is at least partially cross-linked.

In an embodiment of the first aspect, from about 1% w/w to about 50% w/w of the cell impermeable domain is the hydrophilic copolymer.

In an embodiment of the first aspect, from about 5% w/w to about 30% w/w of the cell impermeable domain is the hydrophilic copolymer.

In an embodiment of the first aspect, the silicone material has a micellar jacket structure.

In an embodiment of the first aspect, the analyte is glucose.

In an embodiment of the first aspect, the sensor is configured to be transcutaneously implanted.

In an embodiment of the first aspect, the sensor is configured to be intravascularly implanted.

In an embodiment of the first aspect, the sensor is configured to be wholly implanted.

In an embodiment of the first aspect, the sensor is configured to be extracorporeally implanted.

In an embodiment of the first aspect, the sensor comprises an architecture with at least one dimension less than about 1 mm.

In an embodiment of the first aspect, the electrode comprises a bulk metal or an electrically conductive wire.

In an embodiment of the first aspect, the membrane system further comprises an electrode domain positioned between the electroactive surface and the cell impermeable domain.

In an embodiment of the first aspect, the sensor has a variable stiffness.

In an embodiment of the first aspect, the silicone material comprises a silicone composition and a hydrophile.

In an embodiment of the first aspect, at least a portion of the hydrophile is covalently incorporated into the silicone material.

In an embodiment of the first aspect, the cell impermeable domain is configured to block passage therethrough of at least one interferent.

In an embodiment of the first aspect, the interferent comprises at least one substance selected from the group consisting of hydrogen peroxide, reactive oxygen species, and reactive nitrogen species.

In an embodiment of the first aspect, the interferent comprises at least one substance selected from the group consisting of acetaminophen, ascorbic acid, dopamine, ibuprofen, salicylic acid, tolbutamide, tetracycline, creatinine, uric acid, ephedrine, L-dopa, methyl dopa, and tolazamide.

In an embodiment of the first aspect, the cell impermeable domain is configured to substantially block passage therethrough of at least one non-constant noise causing interferent.

BRIEF DESCRIPTION OF THE DRAWINGS

FIG. 10B is a graph showing test results from implantation of a small-structured sensor without a silicone-PLURONIC® polymer blend cell impermeable domain, in a non-diabetic rat model.

FIG. 10C is a graph showing test results from bilateral implantation of a small-structured sensor having a silicone-PLURONIC® polymer blend cell impermeable domain, in the same rat of FIG. 8B.

DETAILED DESCRIPTION OF THE PREFERRED EMBODIMENT

Figure 1A:
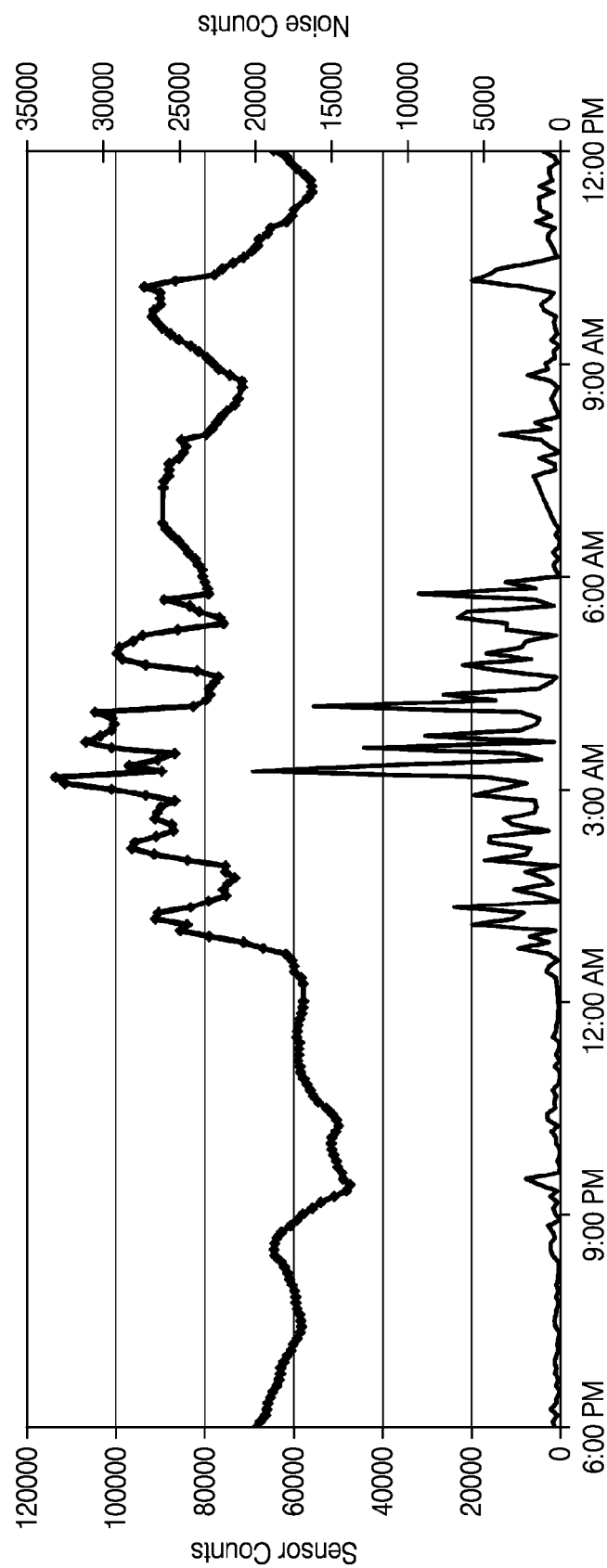
FIG. 1A is a graph illustrating non-constant noise during use of a small-structured sensor in one human volunteer host.

The following description and examples illustrate some embodiments of the present invention in detail. Those of skill in the art will recognize that there are numerous variations and modifications of this invention that are encompassed by its scope. Accordingly, the description of some embodiments should not be deemed to limit the scope of the present invention.

Definitions

In order to facilitate an understanding of the preferred embodiment, a number of terms are defined below.

The term "adhere" and "attach" as used herein are broad terms, and are to be given their ordinary and customary meaning to a person of ordinary skill in the art (and are not to be limited to a special or customized meaning), and refer without limitation to hold, bind, or stick, for example, by gluing, bonding, grasping, interpenetrating, or fusing.

The term "adipose" as used herein is a broad term, and is to be given its ordinary and customary meaning to a person of ordinary skill in the art (and is not to be limited to a special or customized meaning), and refers without limitation to fat under the skin and surrounding major organs. For example, "adipose tissue" is fat tissue. In another example, an "adipocyte" is a fat cell.

The term "algorithm" as used herein is a broad term, and is to be given its ordinary and customary meaning to a person of ordinary skill in the art (and is not to be limited to a special or customized meaning), and refers without limitation to a computational process (for example, programs) involved in transforming information from one state to another, for example, by using computer processing.

The term "analyte" as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotimidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F. D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diphtheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani, leptospira*, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), histamine, Advanced Glycation End Products (AGEs) and 5-hydroxyindoleacetic acid (FHIAA).

The terms "analyte measuring device," "sensor," "sensor system," "sensing region," and "sensing mechanism" as used herein are broad terms, and are to be given their ordinary and customary meaning to a person of ordinary skill in the art (and are not to be limited to a special or customized meaning), and refer without limitation to an area of an analyte-monitoring device that enables the detection (and/or quantification) of a particular analyte. For example, the sensing region can comprise a non-conductive body, a working electrode, a reference electrode, and a counter electrode (optional), forming an electrochemically reactive surface at one location on the body and an electronic connection at another location on the body, and a sensing membrane affixed to the body and covering the electrochemically reactive surface. During general operation of the device, a biological sample, for example, blood or interstitial fluid, or a component thereof contacts, either directly or after passage through one or more membranes, an enzyme, for example, glucose oxidase. The reaction of the biological sample or component thereof results in the formation of reaction products that permit a determination of the analyte level, for example, glucose, in the biological sample. In some embodiments, the sensing membrane further comprises an enzyme domain, for example, an enzyme layer, and an electrolyte phase, for example, a free-flowing liquid phase comprising an electrolyte-containing fluid described further below. The terms are broad enough to include the entire device, or only the sensing portion thereof (or something in between).

The term "barrier cell layer" as used herein is a broad term, and is to be given its ordinary and customary meaning to a person of ordinary skill in the art (and is not to be limited to a special or customized meaning), and refers without limitation to a part of a foreign body response that forms a cohesive monolayer of cells (for example, macrophages and foreign body giant cells) that substantially block the transport of molecules and other substances to the implantable device.

The term "baseline" as used herein is a broad term, and is to be given its ordinary and customary meaning to a person of ordinary skill in the art (and is not to be limited to a special or customized meaning), and refers without limitation to the component of an analyte sensor signal that is not substantially related to the analyte concentration and is substantially constant. In one example of a glucose sensor, the baseline is composed substantially of signal contribution due to constant factors other than glucose (for example, interfering species, non-reaction-related hydrogen peroxide, or other electroactive species with an oxidation potential that overlaps with hydrogen peroxide and remain at substantially constant levels within the host's body). In some embodiments wherein a calibration is defined by solving for the equation $y=mx+b$, the value of b represents the baseline of the signal.

The terms "baseline and/or sensitivity shift," "baseline and/or sensitivity drift," "shift," and "drift" as used herein are broad terms, and are to be given their ordinary and customary meaning to a person of ordinary skill in the art (and are not to be limited to a special or customized meaning), and refer without limitation to a change (increase or decrease) in the baseline and/or sensitivity of the sensor signal over time that is unrelated to changes in host systemic analyte concentrations, such as host postprandial glucose concentrations, for example. While the term "shift" generally refers to a substantially distinct change over a relatively short time period, and the term "drift" generally refers to a substantially gradual change over a relatively longer time period, the terms can be used interchangeably and can also be generally referred to as "change" in baseline and/or sensitivity. It is believed that, in some circumstances, drift can be the result of a local decrease in glucose transport to the sensor, due to cellular invasion, which surrounds the sensor and forms a FBC, for example.

The term "bioactive agent" as used herein is a broad term, and is to be given its ordinary and customary meaning to a person of ordinary skill in the art (and is not to be limited to a special or customized meaning), and refers without limitation to any substance that has an effect on or elicits a response from molecules, cells and/or tissues in the body.

The term "bioerodible" or "biodegradable" as used herein are a broad terms, and are to be given their ordinary and customary meaning to a person of ordinary skill in the art (and are not to be limited to a special or customized meaning), and refer without limitation to materials that are enzymatically degraded or chemically degraded in vivo into simpler components. One example of a biodegradable material includes a biodegradable polymer that is broken down into simpler components by the body.

The term "biointerface" as used herein is a broad term, and is to be given its ordinary and customary meaning to a person of ordinary skill in the art (and is not to be limited to a special or customized meaning), and refers without limitation to any structure or substance that interfaces between host (tissue or body fluid) and an implantable device.

The term "biointerface membrane" as used herein is a broad term, and is to be given its ordinary and customary meaning to a person of ordinary skill in the art (and is not to be limited to a special or customized meaning), and refers without limitation to a membrane that functions as an interface between host (tissue or body fluid) and an implantable device.

The term "biological sample" as used herein is a broad term, and is to be given its ordinary and customary meaning to a person of ordinary skill in the art (and is not to be limited to a special or customized meaning), and refers without limitation to sample of a host body, for example blood, interstitial fluid, spinal fluid, saliva, urine, tears, sweat, or the like.

The terms "bioresorbable" or "bioabsorbable" as used herein are broad terms, and are to be given their ordinary and customary meaning to a person of ordinary skill in the art (and are not to be limited to a special or customized meaning), and refer without limitation to materials that can be absorbed, or lose substance, in a biological system.

The term "biostable" as used herein is a broad term, and is to be given its ordinary and customary meaning to a person of ordinary skill in the art (and is not to be limited to a special or customized meaning), and refers without limitation to materials that are relatively resistant to degradation by processes that are encountered in vivo.

The term "blend" as used herein is a broad term, and is to be given its ordinary and customary meaning to a person of ordinary skill in the art (and is not to be limited to a special or customized meaning), and refers without limitation to a composition of two or more substances that are not substantially chemically combined (e.g., chemically reacted or cross-linked) with each other. In some embodiments, a blend includes at least about 70%, 75%, 80%, or 85% or more of the molecules of the substances are not covalently linked to each other.

The term "bulk fluid flow" as used herein is a broad term, and is to be given its ordinary and customary meaning to a person of ordinary skill in the art (and is not to be limited to a special or customized meaning), and refers without limitation to the movement of fluid(s) within an area or space, or in or out of the area or space. In one embodiment, the fluid moves in and/or out of a fluid pocket surrounding the sensor. In another embodiment, the fluid moves within the fluid pocket. In yet another embodiment, the fluid moves by convection (e.g., the circulatory motion that occurs in a fluid at a non-uniform temperature owing to the variation of its density and the action of gravity).

The term "calibration" as used herein is a broad term, and is to be given its ordinary and customary meaning to a person of ordinary skill in the art (and is not to be limited to a special or customized meaning), and refers without limitation to the process of determining the relationship between the sensor data and the corresponding reference data, which can be used to convert sensor data into meaningful values substantially equivalent to the reference data. In some embodiments, namely, in continuous analyte sensors, calibration can be updated or recalibrated over time as changes in the relationship between the sensor data and reference data occur, for example, due to changes in sensitivity, baseline, transport, metabolism, or the like.

The term "casting" as used herein is a broad term, and is to be given its ordinary and customary meaning to a person of ordinary skill in the art (and is not to be limited to a special or customized meaning), and refers without limitation to a process where a fluid material is applied to a surface or surfaces and allowed to cure or dry. The term is broad enough to encompass a variety of coating techniques, for example, using a draw-down machine (i.e., drawing-down), dip coating, spray coating, spin coating, or the like.

The term "cell processes" as used herein is a broad term, and is to be given its ordinary and customary meaning to a person of ordinary skill in the art (and is not to be limited to a special or customized meaning), and refers without limitation to pseudopodia of a cell.

The term "cellular attachment" as used herein is a broad term, and is to be given its ordinary and customary meaning to a person of ordinary skill in the art (and is not to be limited to a special or customized meaning), and refers without limitation to adhesion of cells and/or cell processes to a material at the molecular level, and/or attachment of cells and/or cell processes to microporous material surfaces or macroporous material surfaces. One example of a material used in the prior art that encourages cellular attachment to its porous surfaces is the BIOPORE™ cell culture support marketed by Millipore (Bedford, Mass.), and as described in Brauker et al., U.S. Pat. No. 5,741,330.

The terms "chloridization" and "chloridizing" as used herein are broad terms, and are to be given their ordinary and customary meaning to a person of ordinary skill in the art (and are not to be limited to a special or customized meaning), and refer without limitation to treatment or preparation with chloride. The term "chloride" as used herein, is a broad term and is used in its ordinary sense, including, without limitation, to refer to $Cl^-$ ions, sources of $Cl^-$ ions, and salts of hydrochloric acid. Chloridization and chloridizing methods include, but are not limited to, chemical and electrochemical methods.

The term "co-continuous" as used herein is a broad term, and is to be given its ordinary and customary meaning to a person of ordinary skill in the art (and is not to be limited to a special or customized meaning), and refers without limitation to a solid portion or cavity or pore wherein an unbroken curved line in three dimensions can be drawn between two sides of a membrane.

The term "comprising" as used herein is a broad term, and is to be given its ordinary and customary meaning to a person of ordinary skill in the art (and is not to be limited to a special or customized meaning), and without limitation to is synonymous with "including," "containing," or "characterized by," and is inclusive or open-ended and does not exclude additional, unrecited elements or method steps.

The phrase "continuous (or continual) analyte sensing" as used herein is a broad term, and is to be given its ordinary and customary meaning to a person of ordinary skill in the art (and is not to be limited to a special or customized meaning), and refers without limitation to the period in which monitoring of analyte concentration is continuously, continually, and/or intermittently (but regularly) performed, for example, from about every 5 seconds or less to about 10 minutes or more, preferably from about 10, 15, 20, 25, 30, 35, 40, 45, 50, 55, or 60 seconds to about 1.25, 1.50, 1.75, 2.00, 2.25, 2.50, 2.75, 3.00, 3.25, 3.50, 3.75, 4.00, 4.25, 4.50, 4.75, 5.00, 5.25, 5.50, 5.75, 6.00, 6.25, 6.50, 6.75, 7.00, 7.25, 7.50, 7.75, 8.00, 8.25, 8.50, 8.75, 9.00, 9.25, 9.50 or 9.75 minutes.

The phrase "continuous glucose sensing" as used herein is a broad term, and is to be given its ordinary and customary meaning to a person of ordinary skill in the art (and is not to be limited to a special or customized meaning), and refers without limitation to the period in which monitoring of plasma glucose concentration is continuously or continually performed, for example, at time intervals ranging between fractions of a second up and, for example, 1, 2, or 5 minutes, or longer.

The term "copolymer" as used herein is a broad term, and is to be given its ordinary and customary meaning to a person of ordinary skill in the art (and is not to be limited to a special or customized meaning), and refers without limitation to a substance with a high molecular weight that results from chemically combining two or more dissimilar monomers.

The term "count" as used herein is a broad term, and is to be given its ordinary and customary meaning to a person of ordinary skill in the art (and is not to be limited to a special or customized meaning), and refers without limitation to a unit of measurement of a digital signal. For example, a raw data stream or raw data signal measured in counts is directly related to a voltage (for example, converted by an A/D converter), which is directly related to current from the working electrode.

The terms "crosslink" and "crosslinking" as used herein are broad terms, and are to be given their ordinary and customary meaning to a person of ordinary skill in the art (and are not to be limited to a special or customized meaning), and refer without limitation to joining (e.g., adjacent chains of a polymer or protein) by creating covalent bonds. Crosslinking can be accomplished by techniques such as thermal reaction, chemical reaction or by providing ionizing radiation (for example, electron beam radiation, UV radiation, or gamma radiation). In some embodiments, the PLURONIC® is crosslinked by treatment with dicumyl peroxide.

The term "dip coating" as used herein is a broad term, and is to be given its ordinary and customary meaning to a person of ordinary skill in the art (and is not to be limited to a special or customized meaning), and refers without limitation to coating that involves dipping an object or material into a liquid coating substance. The term "in vivo portion" as used herein is a broad term, and is to be given its ordinary and customary meaning to a person of ordinary skill in the art (and is not to be limited to a special or customized meaning), and refers without limitation to the portion of the device (for example, a sensor) adapted for insertion into and/or existence within a living body of a host.

The term "distal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively farther from the reference point than another element.

The term "domain" as used herein is a broad term, and is to be given its ordinary and customary meaning to a person of ordinary skill in the art (and is not to be limited to a special or customized meaning), and refers without limitation to a region of the membrane system that can be a layer, a uniform or non-uniform gradient (for example, an anisotropic region of a membrane), or a portion of a membrane.

The term "edema" as used herein is a broad term, and is to be given its ordinary and customary meaning to a person of ordinary skill in the art (and is not to be limited to a special or customized meaning), and refers without limitation to an abnormal infiltration and excess accumulation of serous fluid in connective tissue or in a serous cavity. In one example, edematous fluid is the fluid an edema.

The term "electrochemically reactive surface" as used herein is a broad term, and is to be given its ordinary and customary meaning to a person of ordinary skill in the art (and is not to be limited to a special or customized meaning), and refers without limitation to the surface of an electrode where an electrochemical reaction takes place. In a working electrode, hydrogen peroxide produced by an enzyme-catalyzed reaction of an analyte being detected reacts can create a measurable electronic current. For example, in the detection of glucose, glucose oxidase produces $H_2O_2$ peroxide as a byproduct. The $H_2O_2$ reacts with the surface of the working electrode to produce two protons ($2H^+$), two electrons ($2e^-$) and one molecule of oxygen ($O_2$), which produces the electronic current being detected. In a counter electrode, a reducible species, for example, $O_2$ is reduced at the electrode surface so as to balance the current generated by the working electrode.

The term "electronic connection" as used herein is a broad term, and is to be given its ordinary and customary meaning to a person of ordinary skill in the art (and is not to be limited to a special or customized meaning), and refers without limitation to any electronic connection known to those in the art that can be utilized to interface the sensing region electrodes with the electronic circuitry of a device, such as mechanical (for example, pin and socket) or soldered electronic connections.

The term "exit-site" as used herein is a broad term, and is to be given its ordinary and customary meaning to a person of ordinary skill in the art (and is not to be limited to a special or customized meaning), and refers without limitation to the area where a medical device (for example, a sensor and/or needle) exits from the host's body.

The term "ex vivo portion" as used herein is a broad term, and is to be given its ordinary and customary meaning to a person of ordinary skill in the art (and is not to be limited to a special or customized meaning), and refers without limitation to the portion of the device (for example, a sensor) adapted to remain and/or exist outside of a living body of a host.

The term "fluid influx," as used herein is a broad term, and is to be given its ordinary and customary meaning to a person of ordinary skill in the art (and is not to be limited to a special or customized meaning), and refers without limitation to the movement of fluid(s) into the locality of an implanted sensor.

The term "fluid efflux," as used herein is a broad term, and is to be given its ordinary and customary meaning to a person of ordinary skill in the art (and is not to be limited to a special or customized meaning), and refers without limitation to the movement of fluid(s) out of the locality of an implanted sensor.

The term "high oxygen solubility domain" as used herein is a broad term, and is to be given its ordinary and customary meaning to a person of ordinary skill in the art (and is not to be limited to a special or customized meaning), and refers without limitation to a domain composed of a material that has higher oxygen solubility than aqueous media such that it concentrates oxygen from the biological fluid surrounding the membrane system. The domain can act as an oxygen reservoir during times of minimal oxygen need and has the capacity to provide, on demand, a higher oxygen gradient to facilitate oxygen transport across the membrane. Thus, the ability of the high oxygen solubility domain to supply a higher flux of oxygen to critical domains when needed can improve overall sensor function.

The term "homogeneous" as used herein, with reference to a membrane, is a broad term, and is to be given its ordinary and customary meaning to a person of ordinary skill in the art (and is not to be limited to a special or customized meaning), and refers without limitation to having substantially uniform characteristics, e.g., from one side of the membrane to the other, such as an even distribution of elements. A membrane can have heterogeneous structural domains, for example, created by using block copolymers (e.g., polymers in which different blocks of identical monomer units alternate with each other), and still be characterized functionally as homogenous with respect to its dependence upon dissolution rather than sieving to effect separation of substances.

The term "host" as used herein is a broad term, and is to be given its ordinary and customary meaning to a person of ordinary skill in the art (and is not to be limited to a special or customized meaning), and refers without limitation to mammals, particularly humans.

The term "hydrophilic" as used herein is a broad term, and is to be given its ordinary and customary meaning to a person of ordinary skill in the art (and is not to be limited to a special or customized meaning), and refers without limitation to the property of having affinity for water. For example, a hydrophilic polymer (e.g., having a hydrophilic component) is primarily soluble in water or has a tendency to absorb water. In general, the more hydrophilic a polymer is, the more that polymer tends to dissolve in, mix with, or be wetted by water. In one exemplary embodiment, the hydrophilic component of a hydrophilic polymer promotes the movement of water (e.g., by diffusion or other means) through a membrane formed of the hydrophilic polymer, such as by lowering the thermodynamic barrier to movement of water through the membrane. In some embodiments, a hydrophilic polymer includes a hydrophilic-hydrophobic or hydrophobic-hydrophilic polymer.

The terms "hydrophilic-hydrophobic" and "hydrophobic-hydrophilic," as used herein are broad terms, and are to be given their ordinary and customary meaning to a person of ordinary skill in the art (and are not to be limited to a special or customized meaning), and refer without limitation to the property of having both hydrophilic and hydrophobic substituents and/or characteristics, such as, for example, a polymer. The terms hydrophilic-hydrophobic and hydrophobic-hydrophilic are used interchangeably herein, and are not meant to imply if either the hydrophilic or the hydrophobic substituents are the major component of the polymer.

The term "hydrophobic" as used herein is a broad term, and is to be given its ordinary and customary meaning to a person of ordinary skill in the art (and is not to be limited to a special or customized meaning), and refers without limitation to the property of lacking affinity for, or even repelling, water. For example, the more hydrophobic a polymer, the more that polymer tends to not dissolve in, not mix with, or not be wetted by water. Hydrophilicity and hydrophobicity can be spoken of in relative terms, such as but not limited to a spectrum of hydrophilicity/hydrophobicity within a group of compounds. In some embodiments wherein two or more polymers are being discussed, the term "hydrophobic polymer" can be defined based on the polymer's relative hydrophobicity when compared to another, more hydrophilic polymer. In some embodiments, a hydrophobic polymer includes a hydrophobic-hydrophilic or a hydrophilic-hydrophobic polymer.

The term "ionizing radiation" as used herein is a broad term, and is to be given its ordinary and customary meaning to a person of ordinary skill in the art (and is not to be limited to a special or customized meaning), and refers without limitation to radiation consisting of particles, X-ray beams, electron beams, UV beams, or gamma ray beams, which produce ions in the medium through which it passes.

The term "ischemia" as used herein is a broad term, and is to be given its ordinary and customary meaning to a person of ordinary skill in the art (and is not to be limited to a special or customized meaning), and refers without limitation to local and temporary deficiency of blood supply due to obstruction of circulation to a part (for example, a sensor). Ischemia can be caused, for example, by mechanical obstruction (for example, arterial narrowing or disruption) of the blood supply.

The term "interface" as used herein is a broad term, and is to be given its ordinary and customary meaning to a person of ordinary skill in the art (and is not to be limited to a special or customized meaning), and refers without limitation to 1) a common boundary, such as the surface, place, or point where two things touch each other or meet, or 2) a point of interaction, including the place, situation, or way in which two things act together or affect each other, or the point of connection between things.

The term "in vivo portion" as used herein is a broad term, and is to be given its ordinary and customary meaning to a person of ordinary skill in the art (and is not to be limited to a special or customized meaning), and refers without limitation to the portion of the device (for example, as sensor) adapted for insertion into and/or existence within a living body of a host.

The terms "interferants," "interferents" and "interfering species," as used herein are broad terms, and are to be given their ordinary and customary meaning to a person of ordinary skill in the art (and are not to be limited to a special or customized meaning), and refer without limitation to effects and/or species that interfere with the measurement of an analyte of interest in a sensor to produce a signal that does not accurately represent the analyte measurement. In one example of an electrochemical sensor, interfering species are compounds with oxidation or reduction potentials that overlap with the oxidation potential of the analyte to be measured.

The term "micellar jacket" as used herein is a broad term, and is to be given its ordinary and customary meaning to a person of ordinary skill in the art (and is not to be limited to a special or customized meaning), and refers without limitation to a macromolecular self-organization of amphipathic and hydrophobic polymers which, when substantially blended, creates a mechanism by which analytes are transported at a controlled rate. For example, in one embodiment when PLURONIC® and silicone are substantially blended, a "micellar jacket" structure is formed, which promotes glucose transport through the membrane.

The term "matched data pairs" as used herein is a broad term, and is to be given its ordinary and customary meaning to a person of ordinary skill in the art (and is not to be limited to a special or customized meaning), and refers without limitation to reference data (for example, one or more reference analyte data points) matched with substantially time corresponding sensor data (for example, one or more sensor data points).

The term "membrane system" as used herein is a broad term, and is to be given its ordinary and customary meaning to a person of ordinary skill in the art (and is not to be limited to a special or customized meaning), and refers without limitation to a permeable or semi-permeable membrane that can be comprised of two or more domains and is typically constructed of materials of one or more microns in thickness, which is permeable to oxygen and is optionally permeable to, e.g. glucose or another analyte. In one example, the membrane system comprises an immobilized glucose oxidase enzyme, which enables a reaction to occur between glucose and oxygen whereby a concentration of glucose can be measured.

The term "monolithic" as used herein is a broad term, and is to be given its ordinary and customary meaning to a person of ordinary skill in the art (and is not to be limited to a special or customized meaning), and refers without limitation to being substantially non-porous and having a generally unbroken surface.

The term "nanoporous," as used herein is a broad term, and is to be given its ordinary and customary meaning to a person of ordinary skill in the art (and is not to be limited to a special or customized meaning), and refers without limitation to materials consist of a regular organic or inorganic framework supporting a regular, porous structure having pores roughly in the nanometer range (e.g., from $1 \times 10^{-7}$ to $0.2 \times 10^{-9}$ m).

The term "necrosing agent" as used herein is a broad term, and is to be given its ordinary and customary meaning to a person of ordinary skill in the art (and is not to be limited to a special or customized meaning), and refers without limitation to any drug that causes tissue necrosis or cell death.

The term "needle" as used herein is a broad term, and is to be given its ordinary and customary meaning to a person of ordinary skill in the art (and is not to be limited to a special or customized meaning), and refers without limitation to a slender hollow instrument for introducing material into or removing material from the body.

The term "noise," as used herein is a broad term, and is to be given its ordinary and customary meaning to a person of ordinary skill in the art (and is not to be limited to a special or customized meaning), and refers without limitation to a signal detected by the sensor that is substantially non-analyte related (e.g., non-glucose related). In some circumstances, noise can result in less accurate sensor performance. One type of noise has been observed during the few hours (e.g., about 2 to about 36 hours) after sensor insertion. After the first 24-36 hours, the noise often disappears, but in some hosts, the noise can last for about three to four days. Interfering species, macro- or micro-motion, ischemia, pH changes, temperature changes, pressure, stress, or even unknown sources of mechanical, electrical and/or biochemical can cause noise, in some circumstances, for example. Noise may be referred to as noise event(s), noise episode(s), signal artifact(s), signal artifact event(s) or signal artifact episode(s).

The terms "nonbioresorbable" or "nonbioabsorbable" as used herein are broad terms, and are to be given their ordinary and customary meaning to a person of ordinary skill in the art (and are not to be limited to a special or customized meaning), and refer without limitation to materials that are not substantially absorbed, or do not substantially lose substance, in a biological system.

The terms "operatively connected," "operatively linked," "operably connected," and "operably linked" as used herein are broad terms, and are to be given their ordinary and customary meaning to a person of ordinary skill in the art (and are not to be limited to a special or customized meaning), and refer without limitation to one or more components linked to one or more other components. The terms can refer to a mechanical connection, an electrical connection, or a connection that allows transmission of signals between the components, including a wireless connection. For example, one or more electrodes can be used to detect the amount of analyte in a sample and to convert that information into a signal; the signal can then be transmitted to a circuit. In such an example, the electrode is "operably linked" to the electronic circuitry.

The term "physiologically feasible" as used herein is a broad term, and is to be given its ordinary and customary meaning to a person of ordinary skill in the art (and is not to be limited to a special or customized meaning), and refers without limitation to one or more physiological parameters obtained from continuous studies of glucose data in humans and/or animals. For example, a maximal sustained rate of change of glucose in humans from about 4 mg/dL/min to about 6 mg/dL/min and a maximum acceleration of the rate of change of from about 0.1 mg/dL/min/min to about 0.2 mg/dL/min/min are deemed physiologically feasible limits. Values outside of these limits are considered non-physiological and are likely a result of, e.g. signal error.

The terms "processor module" and "microprocessor" as used herein are broad terms, and are to be given their ordinary and customary meaning to a person of ordinary skill in the art (and are not to be limited to a special or customized meaning), and refer without limitation to a computer system, state machine, processor, or the like designed to perform arithmetic or logic operations using logic circuitry that responds to and processes the basic instructions that drive a computer.

The term "proximal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively near to the reference point than another element.

The terms "raw data stream," "raw data signal," and "data stream" as used herein are broad terms, and are to be given their ordinary and customary meaning to a person of ordinary skill in the art (and are not to be limited to a special or customized meaning), and refer without limitation to an analog or digital signal from the analyte sensor directly related to the measured analyte. For example, the raw data stream is digital data in "counts" converted by an A/D converter from an analog signal (for example, voltage or amps) representative of an analyte concentration. The terms broadly encompass a plurality of time spaced data points from a substantially continuous analyte sensor, each of which comprises individual measurements taken at time intervals ranging from fractions of a second up to, for example, 1, 2, or 5 minutes or longer.

The term "regression" as used herein is a broad term, and is to be given its ordinary and customary meaning to a person of ordinary skill in the art (and is not to be limited to a special or customized meaning), and refers without limitation to finding a line for which a set of data has a minimal measurement (for example, deviation) from that line. Regression can be linear, non-linear, first order, second order, or the like. One example of regression is least squares regression.

The term "sensing membrane" as used herein is a broad term, and is to be given its ordinary and customary meaning to a person of ordinary skill in the art (and is not to be limited to a special or customized meaning), and refers without limitation to a permeable or semi-permeable membrane that can comprise one or more domains and that is constructed of materials having a thickness of a few microns or more, and that are permeable to reactants and/or co-reactants employed in determining the analyte of interest. As an example, a sensing membrane can comprise an immobilized glucose oxidase enzyme, which catalyzes an electrochemical reaction with glucose and oxygen to permit measurement of a concentration of glucose.

The terms "sensitivity" and "slope" as used herein are broad terms, and are to be given their ordinary and customary meaning to a person of ordinary skill in the art (and are not to be limited to a special or customized meaning), and refer without limitation to an amount of electrical current produced by a predetermined amount (unit) of the measured analyte. For example, in one preferred embodiment, a sensor has a sensitivity (or slope) of about 3.5 to about 7.5 picoAmps of current for every 1 mg/dL of glucose analyte.

The term "shedding layer" as used herein is a broad term, and is to be given its ordinary and customary meaning to a person of ordinary skill in the art (and is not to be limited to a special or customized meaning), and refers without limitation to a layer of material (e.g., incorporated into a biointerface) that leaches or releases molecules or components into the surrounding area. One example of a shedding layer includes, a coating of a biodegradable material (e.g., polyvinylalcohol or polyethylene oxide) that is eroded by tissue surrounding the sensor. In another example, the shedding layer includes a polymer hydrogel that degrades and is engulfed by circulating macrophages, which can be stimulated to release inflammatory factors.

The term "short-term sensor" as used herein is a broad term, and is to be given its ordinary and customary meaning to a person of ordinary skill in the art (and is not to be limited to a special or customized meaning), and refers without limitation to sensors used during a short period of time (e.g., short-term), such as 1-3 days, 1-7 days, or longer. In some embodiments, the sensor is used during a short period of time, such as, for 1 day or less, 2, 3, 4, 5, 6, 7, 8, 9, 10, 11, 12, 13, 24, or 15 days. In some embodiments, the sensor is used for a short period of time, such as prior to tissue ingrowth or FBC formation. In some embodiments, a short-term sensor is transcutaneous.

The term "single point glucose monitor" as used herein is a broad term, and is to be given its ordinary and customary meaning to a person of ordinary skill in the art (and is not to be limited to a special or customized meaning), and refers without limitation to a device that can be used to measure a glucose concentration within a host at a single point in time, for example, some embodiments utilize a small volume in vitro glucose monitor that includes an enzyme membrane such as described with reference to U.S. Pat. No. 4,994,167 and U.S. Pat. No. 4,757,022. It should be understood that single point glucose monitors can measure multiple samples (for example, blood or interstitial fluid); however only one sample is measured at a time and typically requires some user initiation and/or interaction.

The terms "small diameter sensor," "small-structured sensor," and "micro-sensor," as used herein are broad terms, and are to be given their ordinary and customary meaning to a person of ordinary skill in the art (and are not to be limited to a special or customized meaning), and refer without limitation to sensing mechanisms that are less than about 2 mm in at least one dimension, and more preferably less than about 1 mm in at least one dimension. In some embodiments, the sensing mechanism (sensor) is less than about 0.95, 0.9, 0.85, 0.8, 0.75, 0.7, 0.65, 0.6, 0.5, 0.4, 0.3, 0.2, or 0.1 mm. In some embodiments, the sensing mechanism is a needle-type sensor, wherein the diameter is less than about 1 mm. See, for example, U.S. Pat. No. 6,613,379 to Ward et al. and U.S. Patent Publication No. US-2006-0020187-A1, both of which are incorporated herein by reference in their entirety. In some alternative embodiments, the sensing mechanism includes electrodes deposited on a planar substrate, wherein the thickness of the implantable portion is less than about 1 mm, see, for example U.S. Pat. No. 6,175,752 to Say et al. and U.S. Pat. No. 5,779,665 to Mastrototaro et al., both of which are incorporated herein by reference in their entirety.

The terms "smoothing" and "filtering" as used herein are broad terms, and are to be given their ordinary and customary meaning to a person of ordinary skill in the art (and are not to be limited to a special or customized meaning), and refer without limitation to modification of a set of data to make it smoother and more continuous or to remove or diminish outlying points, for example, by performing a moving average of the raw data stream.

The term "solid portions" as used herein is a broad term, and is to be given its ordinary and customary meaning to a person of ordinary skill in the art (and is not to be limited to a special or customized meaning), and refers without limitation to portions of a membrane's material having a mechanical structure that demarcates cavities, voids, pores, or other non-solid portions.

The terms "solvent" and "solvent systems" as used herein are broad terms, and are to be given their ordinary and customary meaning to a person of ordinary skill in the art (and are not to be limited to a special or customized meaning), and refer without limitation to substances (e.g., liquids) capable of dissolving or dispersing one or more other substances. Solvents and solvent systems can include compounds and/or solutions that include components in addition to the solvent itself.

The term "spin coating" as used herein is a broad term, and is to be given its ordinary and customary meaning to a person of ordinary skill in the art (and is not to be limited to a special or customized meaning), and refers without limitation to a coating process in which a thin film is created by dropping a raw material solution onto a substrate while it is rotating.

The term "spray coating" as used herein is a broad term, and is to be given its ordinary and customary meaning to a person of ordinary skill in the art (and is not to be limited to a special or customized meaning), and refers without limitation to coating that involves spraying a liquid coating substance onto an object or material.

The terms "substantial" and "substantially" as used herein are broad terms, and are to be given their ordinary and customary meaning to a person of ordinary skill in the art (and are not to be limited to a special or customized meaning), and refer without limitation to a sufficient amount that provides a desired function. For example, the interference domain of some embodiments is configured to resist a sufficient amount of interfering species such that tracking of glucose levels can be achieved, which may include an amount greater than 50 percent, an amount greater than 60 percent, an amount greater than 70 percent, an amount greater than 80 percent, and an amount greater than 90 percent of interfering species. In one exemplary embodiment, two compounds are "substantially blended;" meaning that the two compounds are mixed together and at least more than 50% of the molecules of the two compounds are not chemically linked (e.g., cross-linked). In a more preferred exemplary embodiment, at least 70, 75, 80, 85, 90 or 90%, or more, of the blended compounds are not chemically linked. In an exemplary embodiment of a substantial blend of a silicone polymer and a hydrophilic copolymer, at least 95% or more of the silicone polymer is not chemically cross-linked with the hydrophilic copolymer.

Overview

Noise

Generally, implantable sensors measure a signal (e.g., counts) related to an analyte of interest in a host. For example, an electrochemical sensor can measure glucose, creatinine, or urea in a host, such as an animal, especially a human. Generally, the signal is converted mathematically to a numeric value indicative of analyte status, such as analyte concentration. It is not unusual for a sensor to experience a certain level of noise. "Noise," as used herein, is a broad term and is used in its ordinary sense, including, without limitation, a signal detected by the sensor that is caused by substantially non-analyte related phenomena (e.g., non-constant, of a biological nature, unrelated to analyte concentration) and can result in reduced sensor performance. Noise can be caused by a variety of factors, for example, interfering species, macro- or micro-motion, ischemia, pH changes, temperature changes, pressure, stress, or even unknown sources of mechanical, electrical and/or biochemical noise. Since noise can obscure analyte data, reduction of noise is desirable.

There are a variety of ways noise can be recognized and/or analyzed. In preferred embodiments, the sensor data stream is monitored, signal artifacts are detected and data processing can be performed based at least in part on whether or not a signal artifact has been detected, such as described in U.S. Patent Publication No. US-2005-0043598-A1.

It was observed that some inserted sensors functioned more poorly during the first few hours or days after insertion than they did later. This was exemplified by noise and/or a suppression of the signal during the first about 2-36 hours or more after insertion. These anomalies often resolved spontaneously, after which the sensors became less noisy, had improved sensitivity, and were more accurate than during the early period. Moreover, the noise predominated when hosts were sleeping or sedentary for a period of time.

FIG. 1A illustrates this phenomenon of noise associated with the above-described intermittent sedentary activity during the first few days of insertion of a small-structure sensor glucose sensor (e.g., short-term use) containing active enzyme (in a non-diabetic host). The X-axis represents time; the left Y-axis represents sensor signal in counts (e.g., signal to be converted into glucose level in mg/dL) and the right Y-axis represents noise within the sensor signal in counts (determined algorithmically according to U.S. Patent Publication No. US-2005-0043598-A1 herein incorporated by reference in its entirety). An enzymatic glucose sensor was built, including enzyme, as described in U.S. Patent Publication No. US-2005-0020187-A1. During the day, the sensor signal (upper line) varied and substantially correlated with glucose concentration. But, when the host went to sleep at about midnight, noise (lower line) began to occur. Between midnight and 6 AM, when the host was asleep, there was a lot of noise, as evidenced by the large number of high peaks in the noise plot (lower line). When the host awoke and began moving around, at about 6 AM, the noise dissipated and signal substantially represented glucose concentration again.

Figure 1B:
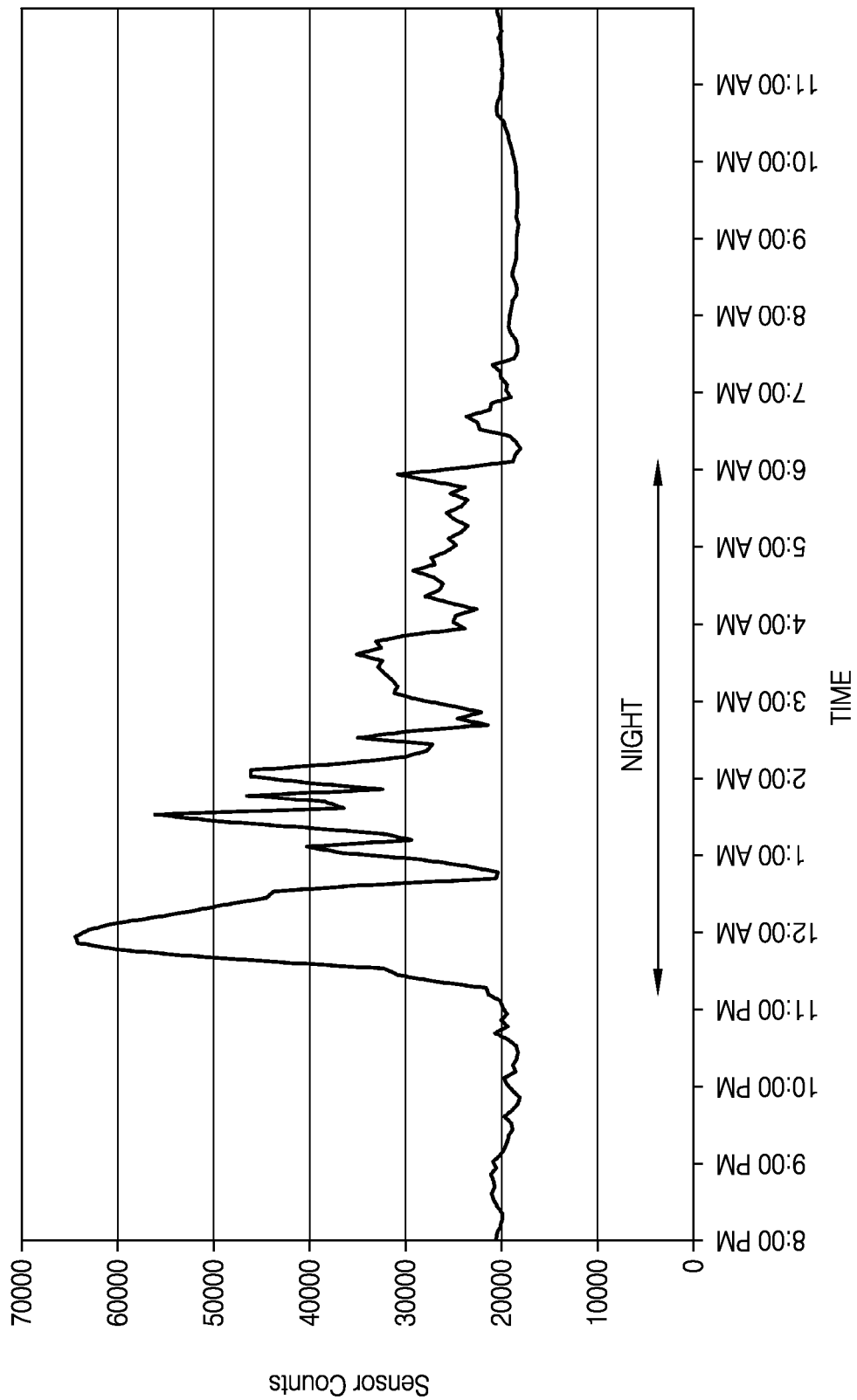
FIG. 1B is a graph illustrating non-constant noise during use of a small-structured sensor in a second human volunteer host.

Studies to observe noise were conducted in non-diabetic individuals using enzymatic-type glucose sensors built without enzyme. These sensors (without enzyme) do not react with or measure glucose and therefore provide a signal due to non-glucose effects (e.g., baseline, interferants, and noise). These studies demonstrated that the noise observed during sedentary periods was caused by something other than glucose concentration. FIG. 1B shows one example of the experimental results, in a non-diabetic host wearing a small-structured, short-term glucose sensor built without enzyme. When the host was asleep, the no-enzyme sensor showed large, sustained positive signals that resembled glucose peaks, but could not represent actual glucose concentration because the sensor lacked enzyme. In the morning, when the host awoke and moved around, the no-enzyme signal rapidly corrected, becoming measurably reduced and smoother. From these results, the inventors believe that a reactant was diffusing to the electrodes and producing the unexpected positive signal.

Additional, in vitro experiments were conducted to determine if a sensor (e.g., electrode) component might have leached into the area surrounding the sensor. These in vitro experiments provided evidence that the non-glucose signals (observed during host sedentary periods) were not produced by contaminants of the sensor itself, or products of the chemical reaction at the electrodes, because the noise and non-glucose peaks did not occur in vitro.

While not wishing to be bound by theory, it is believed that non-constant noise is caused by an interferant that is likely produced by local cellular activity (e.g., associated with wound healing) at the site of sensor insertion. The interferant is believed to have an oxidation/reduction potential that substantially overlaps with that of the analyzed species (e.g., the analyte or a product of the analyte being reacted upon by the analyte-detecting enzyme, etc.). Physiologic activity at a wound site is complex and involves the interaction of a variety of body processes. In order to fully understand the cause of intermittent, sedentary noise (as well as solutions), one must understand wound healing, fluid transport within the body (e.g., lymph transport) and tissue response to implanted materials (e.g., foreign body response). Each of these processes is discussed in greater detail below.

Foreign Body Response

Devices and probes that are inserted or implanted into subcutaneous tissue conventionally elicit a foreign body response (FBR), which includes invasion of inflammatory cells that ultimately forms a foreign body capsule (FBC), as part of the body's response to the introduction of a foreign material in a wound. Specifically, insertion or implantation of a device, for example, a glucose-sensing device, can result in an acute inflammatory reaction (e.g., a part of the wound healing process) resolving to chronic inflammation with concurrent building of fibrotic tissue (e.g., to isolate the foreign material from surrounding tissue). Eventually, over a period of two to three weeks, a mature FBC, including primarily contractile fibrous tissue, forms around the device. See Shanker and Greisler, Inflammation and Biomaterials in Greco R S, ed., "Implantation Biology: The Host Response and Biomedical Devices" pp 68-80, CRC Press (1994). The FBC surrounding conventional implanted devices has been shown to hinder or block the transport of analytes across the device-tissue interface. Thus, continuous extended life analyte transport (e.g., beyond the first few days) in vivo has been conventionally believed to be unreliable or impossible.

Figure 2A:
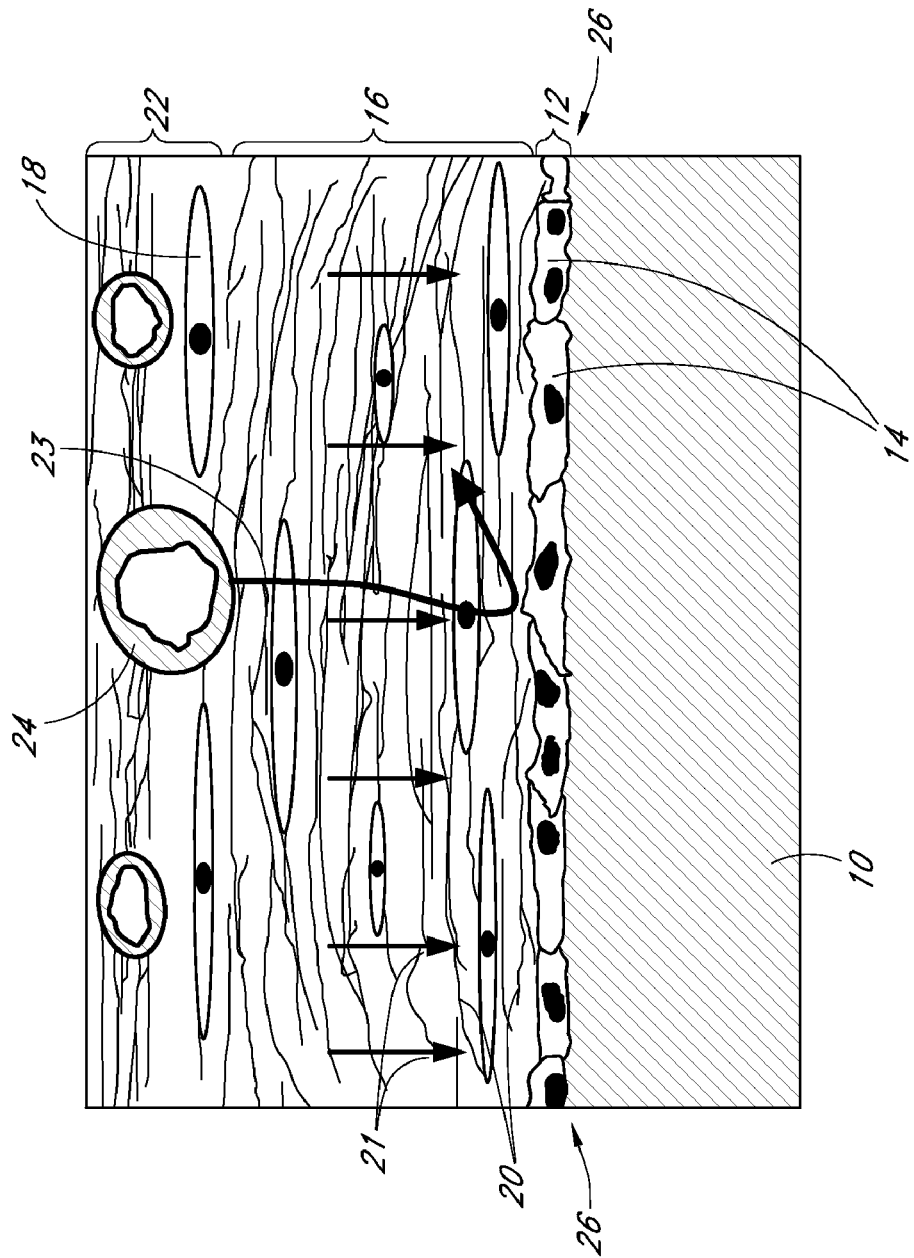
FIG. 2A is an illustration of classical three-layered foreign body response to a conventional synthetic membrane implanted under the skin.

FIG. 2A is a schematic drawing that illustrates a classical FBR to a conventional cell-impermeable synthetic membrane 10 implanted under the skin over a period of about two or more weeks. There are three main layers of a FBR. The innermost FBR layer 12, adjacent to the device, is composed generally of macrophages and foreign body giant cells 14 (herein referred to as the "barrier cell layer"). These cells form a monolayer of closely opposed cells over the entire surface of a microscopically smooth membrane, a macroscopically smooth (but microscopically rough) membrane, or a microporous (i.e., average pore size of less than about 1 μm) membrane. A membrane can be adhesive or non-adhesive to cells; however, its relatively smooth surface causes the downward tissue contracture 21 (discussed below) to translate directly to the cells at the device-tissue interface 26. The intermediate FBR layer 16 (herein referred to as the "fibrous zone"), lying distal to the first layer with respect to the device, is a wide zone (about 30 to 100 μm) composed primarily of fibroblasts 18, fibrous matrixes, and contractile fibrous tissue 20. The organization of the fibrous zone, and particularly the contractile fibrous tissue 20, contributes to the formation of the monolayer of closely opposed cells due to the contractile forces 21 around the surface of the foreign body (for example, membrane 10). The outermost FBR layer 22 is loose connective granular tissue containing new blood vessels 24 (herein referred to as the "vascular zone"). Over time, this FBR tissue becomes muscular in nature and contracts around the foreign body so that the foreign body remains tightly encapsulated. Accordingly, the downward forces 21 press against the tissue-device interface 26, and without any counteracting forces, aid in the formation of a barrier cell layer 14 that blocks and/or refracts the transport of analytes 23 (for example, glucose) across the tissue-device interface 26.

A consistent feature, of the innermost layers 12, 16, is that they are devoid of blood vessels. This has led to widely supported speculation that poor transport of molecules across the device-tissue interface 26 is due to a lack of vascularization near the interface. See Scharp et al., World J. Surg., 8:221-229 (1984); and Colton et al., J. Biomech. Eng., 113: 152-170 (1991). Previous efforts to overcome this problem have been aimed at increasing local vascularization at the device-tissue interface, but have achieved only limited success.

Although local vascularization can aid in sustenance of local tissue over time, the presence of a barrier cell layer 14 prevents the passage of molecules that cannot diffuse through the layer. For example, when applied to an implantable glucose-measuring device, it is unlikely that glucose would enter the cell via glucose transporters on one side of the cell and exit on the other side. Instead, it is likely that any glucose that enters the cell is phosphorylated and remains within the cell. The only cells known to facilitate transport of glucose from one side of the cell to another are endothelial cells. Consequently, little glucose reaches the implant's membrane through the barrier cell layer. The known art purports to increase the local vascularization in order to increase solute availability. See Brauker et al., U.S. Pat. No. 5,741,330. However, it has been observed by the inventors that once the monolayer of cells (barrier cell layer) is established adjacent to a membrane, increasing angiogenesis is not sufficient to increase transport of molecules such as glucose and oxygen across the device-tissue interface 26. In fact, the barrier cell layer blocks and/or refracts the analytes 23 from transport across the device-tissue interface 26.

Referring now to long-term function of a sensor, after a few days to two or more weeks of implantation, conventional devices typically lose their function. In some applications, cellular attack or migration of cells to the sensor can cause reduced sensitivity and/or function of the device, particularly after the first day of implantation. See also, for example, U.S. Pat. No. 5,791,344 and Gross et al. and "Performance Evaluation of the MiniMed Continuous Monitoring System During Host home Use," Diabetes Technology and Therapeutics, (2000) 2(1):49-56, which have reported a glucose oxidase-based device, approved for use in humans by the Food and Drug Administration, that functions well for several days following implantation but loses function quickly after the several days (e.g., a few days up to about 14 days).

It is believed that this lack of device function is most likely due to cells, such as polymorphonuclear cells and monocytes that migrate to the sensor site during the first few days after implantation. These cells consume local glucose and oxygen. If there is an overabundance of such cells, they can deplete glucose and/or oxygen before it is able to reach the device enzyme domain, thereby reducing the sensitivity of the device or rendering it non-functional. Further inhibition of device function can be due to inflammatory cells recruited during the wound healing process, for example, macrophages, that associate, for example, align at the interface, with the implantable device, and physically block the transport of glucose into the device, for example, by formation of a barrier cell layer. Additionally, these inflammatory cells can biodegrade many artificial biomaterials (some of which were, until recently, considered non-biodegradable). When activated by a foreign body, tissue macrophages degranulate, releasing hypochlorite (bleach) and other oxidative species. Hypochlorite and other oxidative species are known to break down a variety of polymers.

In some circumstances, for example in long-term sensors, it is believed that that foreign body response is the dominant event surrounding extended implantation of an implanted device, and can be managed or manipulated to support rather than hinder or block analyte transport. In another aspect, in order to extend the lifetime of the sensor, preferred embodiments employ materials that promote vascularized tissue ingrowth, for example within a porous biointerface membrane. For example tissue in-growth into a porous biointerface material surrounding a long-term sensor may promote sensor function over extended periods of time (e.g., weeks, months, or years). It has been observed that in-growth and formation of a tissue bed can take up to 3 weeks. Tissue ingrowth and tissue bed formation is believed to be part of the foreign body response. As will be discussed herein, the foreign body response can be manipulated by the use of porous biointerface materials that surround the sensor and promote ingrowth of tissue and microvasculature over time. Long-term use sensors, for use over a period of weeks, months or even years, have also been produced. Long-term sensors may be wholly implantable, and placed within the host's soft tissue below the skin, for example.

Accordingly, a long term sensor including a biointerface, including but not limited to, for example, porous biointerface materials including a solid portion and interconnected cavities, can be employed to improve sensor function in the long term (e.g., after tissue ingrowth).

Referring now to short-term sensors, or the short-term function of long-term sensors, it is believed that certain aspects of the FBR in the first few days (e.g., the wound healing response) may play a role in noise. As discussed above, it has been observed that some sensors function more poorly during the first few hours after insertion than they do later. This is exemplified by noise and/or a suppression of the signal during the first few hours (e.g., about 2 to about 24 hours) after insertion. These anomalies often resolve spontaneously after which the sensors become less noisy, have improved sensitivity, and are more accurate than during the early period. It has been observed that some transcutaneous sensors and wholly implantable sensors are subject to noise for a period of time after application to the host (i.e., inserted transcutaneously or wholly implanted below the skin). Noise has been observed during the few hours (e.g., about 2 to about 24 hours) after sensor insertion. After the first 24 hours, the noise often disappears, but in some hosts (approximately 20%), the noise may last for about three to four days.

When a sensor is first inserted or implanted into the subcutaneous tissue, it comes into contact with a wide variety of possible tissue conformations. Subcutaneous tissue in different hosts may be relatively fat free in cases of very athletic people, or may be mostly composed of fat in the majority of people. Fat comes in a wide array of textures from very white, puffy fat to very dense, fibrous fat. Some fat is very yellow and dense looking; some is very clear, puffy, and white looking, while in other cases it is more red or brown. The fat may be several inches thick or only 1 cm thick. It may be very vascular or relatively nonvascular. Many hosts with diabetes have some subcutaneous scar tissue due to years of insulin pump use or insulin injection. At times, during insertion, sensors may come to rest in such a scarred area. The subcutaneous tissue may even vary greatly from one location to another in the abdomen of a given host. Moreover, by chance, the sensor may come to rest near a more densely vascularized area or in a less vascularized area of a given host. While not wishing to be bound by theory, it is believed that creating a space between the sensor surface and the surrounding cells, including formation of a fluid pocket surrounding the sensor, may enhance sensor performance.

Figure 2B:
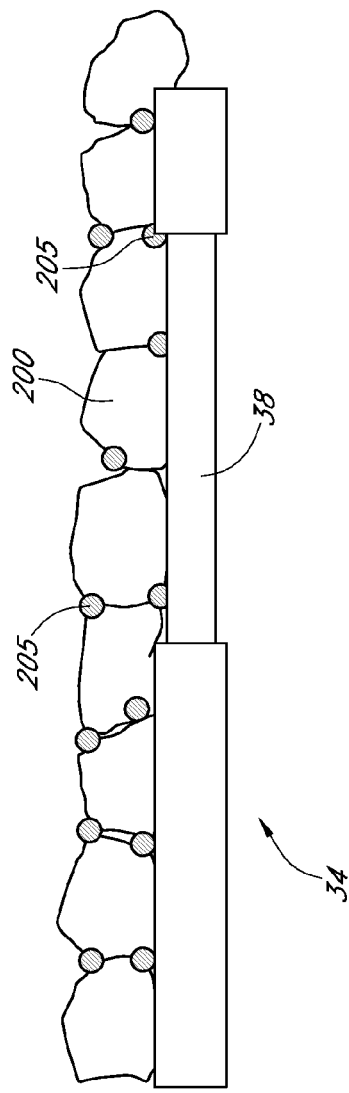
FIG. 2B is a side schematic view of adipose cell contact with an inserted transcutaneous sensor or an implanted sensor.

FIG. 2B is a side schematic view of adipose cell contact with an inserted transcutaneous sensor or an implanted sensor. In this case, the sensor is firmly inserted into a small space with adipose cells pressing up against the surface. Close association of the adipose cells with the sensor can also occur, for example wherein the surface of the sensor is hydrophobic. For example, the adipose cells 200 may physically block the surface of the sensor.

Typically adipose cells can be about 120 microns in diameter and are typically fed by tiny capillaries 205. When the sensor is pressed against the fat tissue, very few capillaries may actually come near the surface of the sensor. This may be analogous to covering the surface of the sensor with an impermeable material such as cellophane, for example. Even if there were a few small holes in the cellophane, the sensor's function would likely be compromised. Additionally, the surrounding tissue has a low metabolic rate and therefore does not require high amounts of glucose and oxygen. While not wishing to be bound by theory, it is believed that, during this early period, the sensor's signal can be noisy and the signal can be suppressed due to close association of the sensor surface with the adipose cells and decreased availability of oxygen and glucose both for physical-mechanical reasons and physiological reasons.

Analyte sensors for in vivo use over various lengths of time have been developed. For example, sensors to be used for a short period of time, such as about 1 to about 14 days, have been produced. Herein, this sensor will be referred to as a short-term sensor. A short-term sensor can be a transcutaneous device, in that a portion of the device may be inserted through the host's skin and into the underlying soft tissue while a portion of the device remains on the surface of the host's skin. In one aspect, in order to overcome the problems associated with noise or other sensor function in the short-term (e.g., short term sensors or short term function of long term sensors), some embodiments employ materials that promote formation of a fluid pocket around the sensor, for example architectures such as porous biointerface membrane or matrices that create a space between the sensor and the surrounding tissue.

In some embodiments, a short-term sensor is provided with a spacer adapted to provide a fluid pocket between the sensor and the host's tissue. It is believed that this spacer, for example a biointerface material, matrix, structure, and the like as described in more detail elsewhere herein, provides for oxygen and/or glucose transport to the sensor.

Figure 2C:
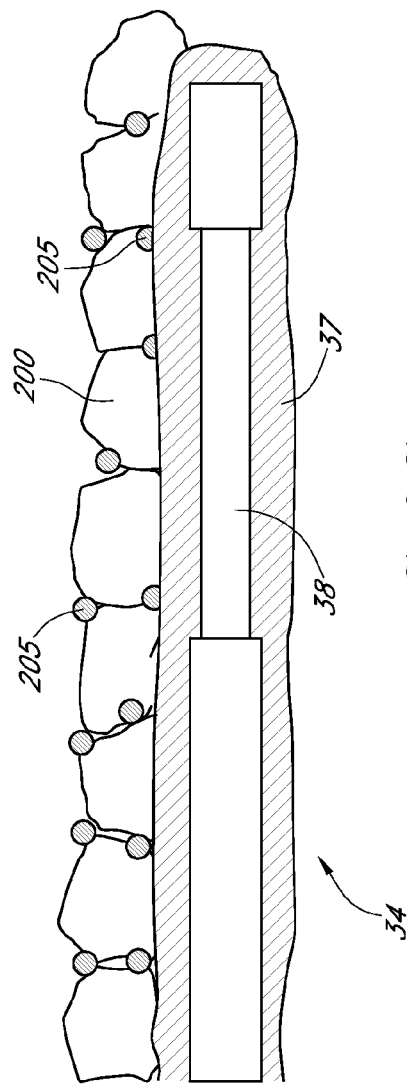
FIG. 2C is a side schematic view of a biointerface membrane preventing adipose cell contact with an inserted transcutaneous sensor or an implanted sensor.

FIG. 2C is a side schematic view of a biointerface membrane as the spacer preventing adipose cell contact with an inserted transcutaneous sensor or an implanted sensor in one exemplary embodiment. In this illustration, a porous biointerface membrane 37 surrounds the sensor 34, covering the sensing mechanism 38, thereby creating a fluid pocket surrounding the sensor. Accordingly, the adipose cells surrounding the sensor are held a distance away (such as the thickness of the porous biointerface membrane, for example) from the sensor surface. Accordingly, as the porous biointerface membrane fills with fluid (i.e., creates fluid pocket), oxygen and glucose are transported to the sensing mechanism in quantities sufficient to maintain accurate sensor function.

Accordingly, a short-term sensor (or short term function of a long term sensor) including a biointerface, including but not limited to, for example, porous biointerface materials, mesh cages, and the like, all of which are described in more detail elsewhere herein, can be employed to improve sensor function in the short term (e.g., first few hours to days). It is noted that porous biointerface membranes need not necessarily include interconnected cavities for creating a fluid pocket in the short-term.

Wound Healing

When a foreign body is inserted into a host, it creates a wound, by breaking the skin and some of the underlying tissue, thereby initiating the wound-healing cascade of events. A wound is also produced, when a sensor, such as an implantable glucose sensor, is implanted into the subcutaneous tissue. For short-term use sensors (such as but not limited to small-structured sensors), as described elsewhere herein, wounding occurs at least from the penetration of the sharp needle or device, which can be used to deliver the sensor. The wound can be relatively extensive, including bruising and/or bleeding, or it can be relatively benign, with little tissue damage and little or virtually no bleeding. Wound healing is initiated immediately upon wounding and is directed by a series of signaling cascades. Wound healing has four main phases: 1) hemostasis, 2) inflammation, 3) granulation, and 4) remodeling, which are discussed in more detail below.

The "hemostasis" phase begins during the first few seconds and minutes after wounding and entails a cascade of molecular events that lead to cessation of bleeding, and the formation of a fibrin scaffold that will be used as a support for cellular responses that follow. During hemostasis, blood platelets are activated by exposure to extravascular collagen and release soluble mediators (growth factors and cAMP) and adhesive glycoproteins that cause the platelets to aggregate and form a fibrin clot. Neutrophils and monocytes are attracted to the wound by platelet-derived growth factor (PDGR) and transforming growth factor beta (TGF-β), to clean the wound of infectious material, foreign matter and devitalized tissue.

Vascular endothelial growth factor (VEGF or VPF), transforming growth factor alpha (TGF-α) and basic fibroblast growth factor (bFGF), which are also secreted by activated platelets, activate endothelial cells that begin angiogenesis. "Angiogenesis" is a physiological process involving the growth of new blood vessels from pre-existing vessels. Platelet secreted PDGF also activates and recruits fibroblasts to produce extracellular matrix components.

The "inflammation" stage begins within the first 24 hours after injury and can last for several weeks in normal wounds and significantly longer in chronic nonhealing wounds. This occurs within several hours after implantation, and is the stage that most closely correlates with the anomalous behavior of the short-term sensor (STS). Inflammation involves the influx of polymorphonuclear cells and the formation of an edematous fluid pocket surrounding the implant. The vascular epithelium becomes highly permeable to cells and fluid so that invading cells (neutrophils, monocytes, and macrophages) can get to the wound site. Mast cells in the wound site release enzymes, histamine, and active amines can cause swelling, redness, heat, and pain depending on the severity of the wound. In most needle track wounds, the extent of the reaction is not sufficient to cause noticeable welling, redness, heat, or pain. Neutrophils, monocytes and macrophages release proinflammatory cytokines (IL-1, IL-6, IL-8 and TNF-α) and cleanse the wound by engulfing bacteria, debris and devitalized tissue. These cells are highly active phagocytic cells with high metabolic requirements, and in an early wound they are proliferating exponentially, creating a need for oxygen, glucose and other molecules. Fibroblasts and epithelial cells are recruited and activated by PDGF, TGF-β, TGF-α, insulin-like growth factor 1 (IGF-1) and FGF, in preparation for the next phase of wound healing.

The "granulation" phase occurs after several days, involving the full participation of a large number of macrophages, and the initiation of fibrosis and vascularization. During the proliferative phase of wound healing, fibroblasts proliferate and deposit granulation tissue components (various types of collagen, elastin, and proteoglycans). Angiogenesis also takes place at this time. Angiogenesis is stimulated by local low oxygen tension. Oxygen promotes angiogenesis by binding hypoxia-inducible factor (HIF) within capillary endothelial cells. When oxygen is low around capillary endothelial cells, HIF levels inside the cells increase and stimulate the production of VEGF, which stimulates angiogenesis. Low pH, high lactate levels, bFGF, and TGF-β also stimulate angiogenesis. Epithelial cells also proliferate and form a new epidermis over the wound.

The "remodeling" phase occurs after several weeks and is not relevant to sensors used for short periods of time, such as about 1 to 3 days, or up to about 7 days or more, or up to about 2 weeks. In the case of long-term wholly implantable sensors, this process is involved in remodeling tissue around the wholly implantable sensor and FBC formation.

The rate of these responses can vary dramatically in a host population, especially among diabetics, who are known to suffer from vascular and wound-healing disorders. Moreover, there is wide variability in the amount, texture, morphology, color, and vascularity of subcutaneous tissue. Therefore it is to be expected that the rate of progress of the wound-healing response, and the quality of the response can vary dramatically among hosts.

Dramatic differences in wounding and noise exist among individuals. Some people wound easily (e.g., bruise more easily or have more bleeding), while others do not. Some people exhibit more noise (e.g., are noisier) in their sensor signal than others. In one example, a glucose tracking study was performed with two non-diabetic volunteer hosts. Samples were collected from the fingertip and the lower abdomen, (e.g., where some short-term sensors are usually implanted). Concurrent blood samples were collected from both the fingertip and abdomen, using a lancet device. The collected blood samples were measured with a hand-held glucose meter.

Figure 3A:
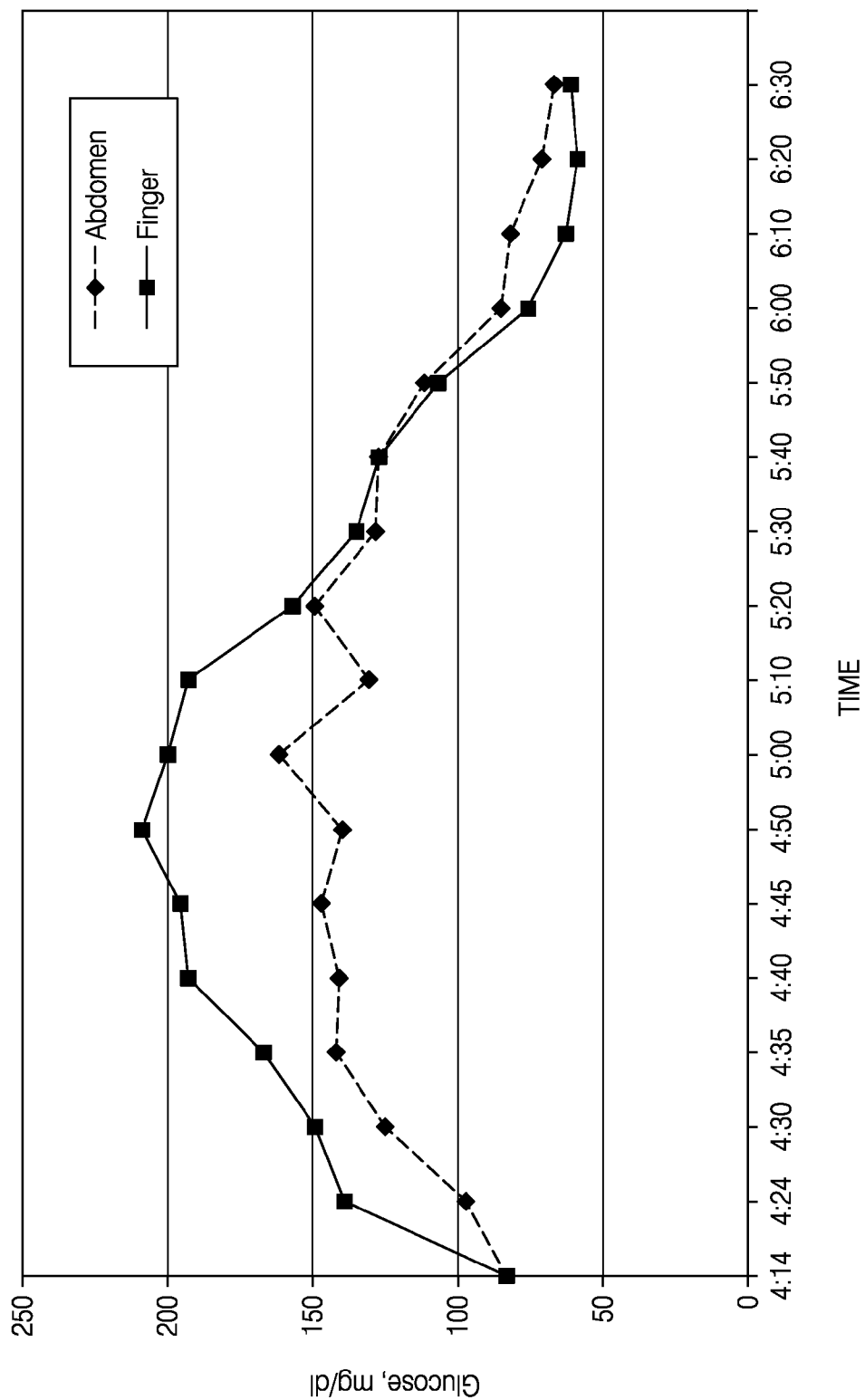
FIG. 3A is a graph illustrating glucose response in a non-diabetic volunteer (Host 1).

FIG. 3A illustrates the difference in responses of finger and abdominal tissue to oral sugar consumption, in a first non-diabetic volunteer host (Host 1). The solid line (with squares) shows glucose concentration at the fingertip. The dashed line (with diamonds) shows glucose concentration at the lower abdomen. When Host 1 ingested about 100 gm of oral sucrose, there was a dramatic and rapid increase in glucose signal from the fingertip samples. Host 1's abdominal signal exhibited a slower and reduced rise, when compared with the fingertip samples.

Figure 3B:
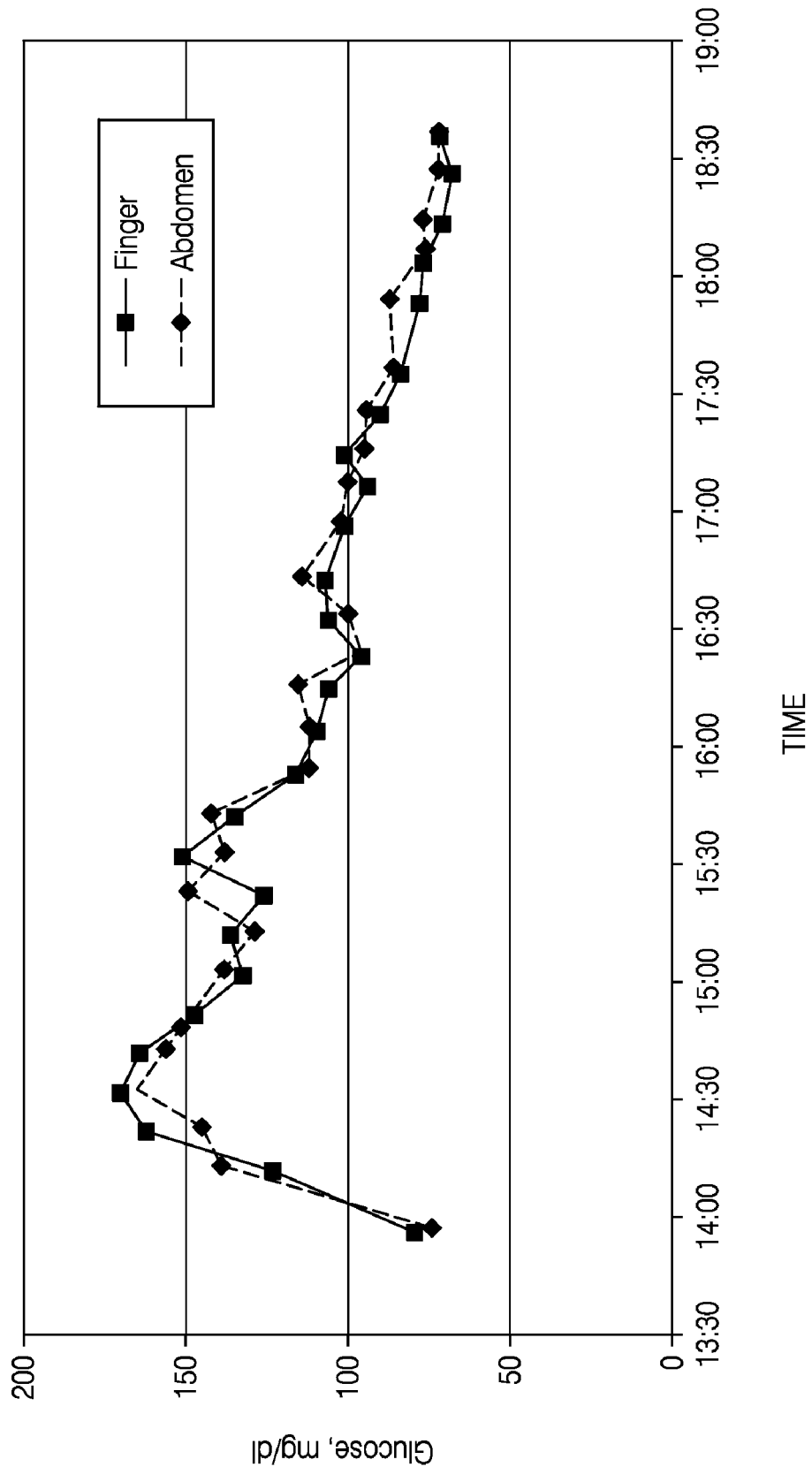
FIG. 3B is a graph illustrating glucose response in a non-diabetic volunteer (Host 2).

FIG. 3B illustrates the difference in responses of finger and abdominal tissue to oral sugar consumption, in a second volunteer non-diabetic host (Host 2). The solid line (with squares) shows glucose concentration at the fingertip. The dashed line (with diamonds) shows glucose concentration at the lower abdomen. When Host 2 was challenged with sucrose consumption, he exhibited little difference between his fingertip and abdominal samples. These data suggest that sensors implanted in different individuals can behave differently.

Different individuals experience relatively different amounts of intermittent, sedentary noise. For example, Host 1, when wearing a short-term sensor, typically was known to experience high levels of nighttime noise, whereas Host 2 experienced very little noise at any time while wearing an exemplary short-term sensor, such as but not limited to a small-structured sensor.

In addition, the amount of wounding varies between individuals as well as between body sites of a single individual. For example, the next day, Host 1's lower abdomen exhibited extensive bruising (e.g., approximately 20 hours after completing the study). However, Host 1's fingertips had very little observable wounding the next day. In contrast, Host 2 sustained little visible wounding the next day (from the lancet), at either the lower abdomen or fingertips.

Because of the host-to-host variability, the location variability (see discussion above, in relation to FIGS. 3A and 3B) in a given host, and the random possibility of hitting a favorable or unfavorable spot in a host, every time an implantable device (e.g., a sensor) is inserted into a host it has the chance of responding differently than it did in another host or at another time or place in the same host. For example, another host can insert a needle or device on day 1 and have no bleeding or bruising, but when she inserts another needle or device on day 3 she can have bleeding with an associated bruise. The wound healing response in a bloody wound will be expected to be considerably different than in a less traumatized wound. As another example, another host can have produced considerable trauma on insertion of a needle/device, without visible bleeding or bruising.

In the case of a less traumatic wound, we believe the inflammatory phase of the wound response would be delayed for some length of time. In the case of a more traumatized wound, we believe it would be accelerated. For example, a fluid pocket can take hours to form in the less traumatic wound whereas it could take much less time in the case of the more traumatic wound.

In the case of a less traumatic wound, when an implantable device, such as a glucose sensor, is initially inserted, relatively little tissue damage occurs. The device finds itself firmly inserted into a small space with adipose tissue pressing up against the surface. Because the surface of the sensor (e.g., a small-structured sensor as described herein) is mainly very hydrophobic, it can associate very closely with the adipose tissue (see FIG. 2B). Because no edema (e.g., wound fluid) is forming or is forming slowly, there will be very little fluid around the sensor for glucose transport. Accordingly, adipose cells can physically block the surface of the sensor. When the sensor is pressed against the adipose tissue, it is believed that that very few capillaries come near the surface of the sensor. Additionally, the surrounding tissue has a low metabolic rate and therefore does not require high amounts of glucose and oxygen. While not wishing to be bound by hypothesis, it is believed that during this period (prior to the formation of an edematous pocket and the influx of cells and glucose) the sensor signal can be noisy and suppressed due to close association of the sensor surface with the adipose cells and lack of availability of oxygen and glucose both for physical-mechanical reasons and physiological reasons. While not wishing to be bound by theory, it is believed that the short-term sensor measures wound fluid surrounding the sensor. Thus, if the rate of edema collection (e.g., collection of wound fluid into a fluid pocket) can be increased then early noise can be alleviated or reduced.

Lymph System and Fluid Transport

The circulatory and lymph systems are the body's means of moving fluids, cells, protein, lipids, and the like throughout the body in an organized fashion. The two systems parallel each other, throughout the body. The circulatory system is a closed system that relies on a pump (the heart) for control of bulk flow. In contrast, the lymph system is an open system with no central pump. The lymph system relies upon pressure differentials, local muscle contraction, among other things, for fluid movement. Gravity and inactivity can have dramatic effects on lymph movement throughout the body, and consequently on noise and sensor function.

Lymph forms when dissolved proteins and solutes filter out of the circulatory system into the surrounding tissues, because of local differences in luminal hydrostatic and osmotic pressure. The fluid within the extracellular spaces is called interstitial fluid. A portion of the interstitial fluid flows back into the circulatory system, while the remaining fluid is collected into the lymph capillaries through valve-like openings between the endothelial cells of the lymph capillaries.

Lymph is generally a clear and transparent semifluid medium. It is known in the art that normal cellular metabolism produces waste species that are removed from the local environment by the lymphatics. Lymph contains a "lymphatic load" of protein, water, lymphocytes, cellular components, metabolic waste and particles, and fat. The lymphatics return the lymph to the circulatory system at the thoracic duct. It is known that lymph has almost the same composition as the original interstitial fluid.

In contrast to the circulatory system, the lymph system is an open system with no central pump. Lymph capillaries take in fluid through "open junctions," until they are filled to capacity. When the pressure inside the capillary is greater than that of the surrounding interstitial tissue, the open junctions close. The lymph moves freely toward larger, downstream portions of the lymph system, where pressure is lower. As the lymph moves forward, it is picked up by "lymph collectors," which have valves that prevent fluid back-flow. Larger portions of the lymph system segmentally contract, to push the lymph forward, from one segment to the next. Breathing movements and skeletal muscle contractions also push the lymph forward. Eventually, the lymph is returned to the circulatory system via the thoracic duct.

Lymph capillaries are delicate and easily flattened. When lymph capillaries are flattened, fluid cannot enter them. Consequently, lymph flow is impeded by a local collapse of the lymph capillaries. Gravity and local pinching of lymph capillaries affect the movement of lymph. For example, it is well known in the medical community that a tourniquet placed on the upper arm can impede lymph flow out of the arm. It is also known that during sleep lymph pools on the side of the body on which a person is lying. In another example, sitting can pinch some of the lower lymphatics, causing lymph to pool in the legs over an extended period of time.

As discussed above, the inventors have found that, soon after insertion of a sensor, noise (e.g., signal not associated with glucose concentration) can occur intermittently (e.g., non-constantly) during sedentary activities, such as sleeping, watching television or reading a book. The inventors have demonstrated experimentally that early intermittent, sedentary noise is, at least in part, the result of unknown interferants that affect the sensor during periods of sustained inactivity.

While not wishing to be bound by theory, it is believed that a local build up of electroactive interferants, such as electroactive metabolites from cellular metabolism and wound healing, interfere with sensor function and cause early intermittent, sedentary noise. Local lymph pooling, when parts of the body are compressed or when the body is inactive can cause, in part, this local build up of interferants (e.g., electroactive metabolites). Interferants can include but are not limited to compounds with electroactive acidic, amine or sulfhydryl groups, urea, lactic acid, phosphates, citrates, peroxides, amino acids (e.g., L-arginine), amino acid precursors or break-down products, nitric oxide (NO), NO-donors, NO-precursors or other electroactive species or metabolites produced during cell metabolism and/or wound healing, for example.

Sensing Mechanism

Figure 4B:
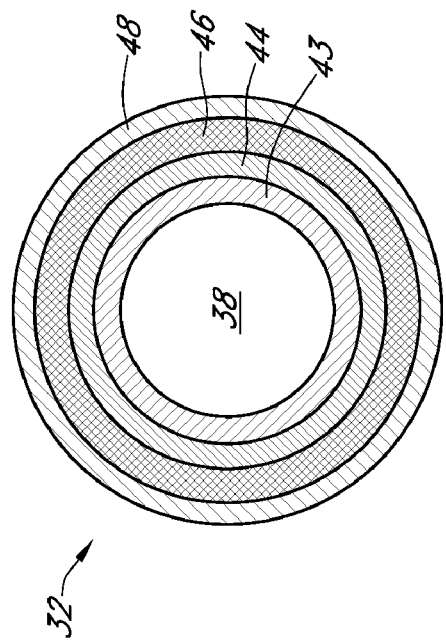
FIG. 4B is a cross-sectional view through the sensor of FIG. 4A on line 4B-4B.
Figure 4A:
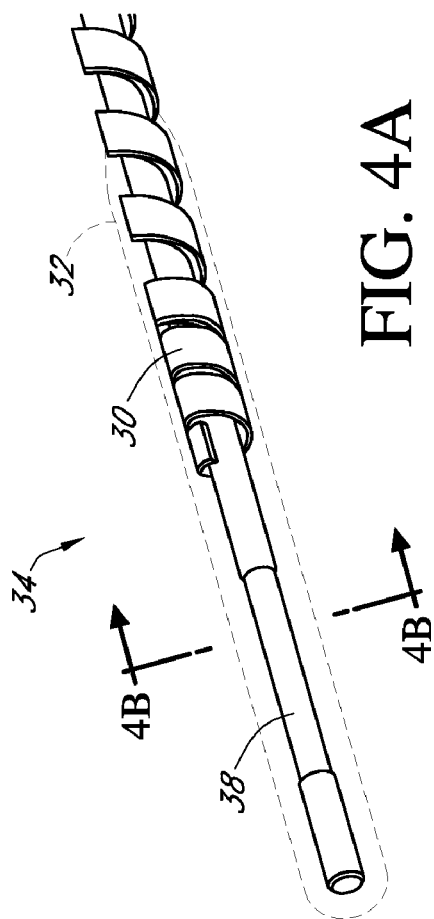
FIG. 4A is an expanded view of an exemplary embodiment of a continuous analyte sensor.

In some embodiments, an analyte sensor includes a sensing mechanism 34 with a small structure (e.g., small-structured, micro- or small diameter sensor), for example, a needle-type sensor, in at least a portion thereof (see FIG. 4A). As used herein the term "small-structured" preferably refers to an architecture with at least one dimension less than about 1 mm. The small structured sensing mechanism can be wire-based, substrate based, or any other architecture. In some alternative embodiments, the term "small-structured" can also refer to slightly larger structures, such as those having their smallest dimension being greater than about 1 mm, however, the architecture (e.g., mass or size) is designed to minimize the foreign body response due to size and/or mass. In some embodiments, a biointerface membrane (e.g., membrane system or sensing membrane) is formed onto the sensing mechanism 34 as described in more detail below.

In the illustrated embodiments, the sensor is an enzyme-based electrochemical sensor, wherein the working electrode 38 measures the hydrogen peroxide ($H_2O_2$) produced by the enzyme catalyzed reaction of glucose being detected and creates a measurable electronic current (for example, detection of glucose utilizing glucose oxidase produces hydrogen peroxide as a by-product, $H_2O_2$ reacts with the surface of the working electrode producing two protons ($2H^+$), two electrons ($2e^-$) and one molecule of oxygen ($O_2$) which produces the electronic current being detected), such as described in more detail herein and as is appreciated by one skilled in the art. Preferably, one or more potentiostat(s) is employed to monitor the electrochemical reaction at the electroactive surface of the working electrode(s). The potentiostat applies a constant potential to the working electrode and its associated reference electrode to determine the current produced at the working electrode. The current that is produced at the working electrode (and flows through the circuitry to the counter electrode) is substantially proportional to the amount of $H_2O_2$ that diffuses to the working electrode. The output signal is typically a raw data stream that is used to provide a useful value of the measured analyte concentration in a host to the host or doctor, for example. In some alternative embodiments, the sensing mechanism includes electrodes deposited on a planar substrate, wherein the thickness of the implantable portion is less than about 1 mm, see, for example U.S. Pat. No. 6,175,752 to Say et al. and U.S. Pat. No. 5,779,665 to Mastrototaro et al., both of which are incorporated herein by reference in their entirety.

Some alternative analyte sensors that can benefit from the systems and methods of some embodiments include U.S. Pat. No. 5,711,861 to Ward et al., U.S. Pat. No. 6,642,015 to Vachon et al., U.S. Pat. No. 6,654,625 to Say et al., U.S. Pat. No. 6,565,509 to Say et al., U.S. Pat. No. 6,514,718 to Heller, U.S. Pat. No. 6,465,066 to Essenpreis et al., U.S. Pat. No. 6,214,185 to Offenbacher et al., U.S. Pat. No. 5,310,469 to Cunningham et al., and U.S. Pat. No. 5,683,562 to Shaffer et al., U.S. Pat. No. 6,579,690 to Bonnecaze et al., U.S. Pat. No. 6,484,046 to Say et al., U.S. Pat. No. 6,512,939 to Colvin et al., U.S. Pat. No. 6,424,847 to Mastrototaro et al., U.S. Pat. No. 6,424,847 to Mastrototaro et al., for example. All of the above patents are incorporated in their entirety herein by reference and are not inclusive of all applicable analyte sensors; in general, it should be understood that the disclosed embodiments are applicable to a variety of analyte sensor configurations.

FIG. 4A is an expanded view of an exemplary embodiment of a continuous analyte sensor 34, also referred to as a transcutaneous analyte sensor, or needle-type sensor, particularly illustrating the sensing mechanism 36. Preferably, the sensing mechanism comprises a small structure as defined herein and is adapted for insertion under the host's skin, and the remaining body of the sensor (e.g., electronics, etc.) can reside ex vivo. In the illustrated embodiment, the analyte sensor 34 includes two electrodes, i.e., a working electrode 38 and at least one additional electrode 30, which may function as a counter and/or reference electrode, hereinafter referred to as the reference electrode 30.

In some exemplary embodiments, each electrode is formed from a fine wire with a diameter of from about 0.001 or less to about 0.010 inches or more, for example, and is formed from, e.g. a plated insulator, a plated wire, or bulk electrically conductive material. Although the illustrated electrode configuration and associated text describe one preferred method of forming a transcutaneous sensor, a variety of known transcutaneous sensor configurations can be employed with the transcutaneous analyte sensor system of some embodiments, such as are described in U.S. Pat. No. 6,695,860 to Ward et al., U.S. Pat. No. 6,565,509 to Say et al., U.S. Pat. No. 6,248,067 to Causey III et al., and U.S. Pat. No. 6,514,718 to Heller et al.

In preferred embodiments, the working electrode comprises a wire formed from a conductive material, such as platinum, platinum-iridium, palladium, graphite, gold, carbon, conductive polymer, alloys, or the like. Although the electrodes can by formed by a variety of manufacturing techniques (bulk metal processing, deposition of metal onto a substrate, or the like), it can be advantageous to form the electrodes from plated wire (e.g. platinum on steel wire) or bulk metal (e.g. platinum wire). It is believed that electrodes formed from bulk metal wire provide superior performance (e.g. in contrast to deposited electrodes), including increased stability of assay, simplified manufacturability, resistance to contamination (e.g. which can be introduced in deposition processes), and improved surface reaction (e.g. due to purity of material) without peeling or delamination.

The working electrode 38 is configured to measure the concentration of an analyte, such as but not limited to glucose, uric acid, cholesterol, lactate and the like. In an enzymatic electrochemical sensor for detecting glucose, for example, the working electrode measures the hydrogen peroxide produced by an enzyme catalyzed reaction of the analyte being detected and creates a measurable electronic current. For example, in the detection of glucose wherein glucose oxidase (GOX) produces hydrogen peroxide as a byproduct, $H_2O_2$ reacts with the surface of the working electrode producing two protons ($2H^+$), two electrons ($2e^-$) and one molecule of oxygen ($O_2$), which produces the electronic current being detected.

The working electrode 38 is covered with an insulating material, for example, a non-conductive polymer. Dip-coating, spray-coating, vapor-deposition, or other coating or deposition techniques can be used to deposit the insulating material on the working electrode. In one embodiment, the insulating material comprises parylene, which can be an advantageous polymer coating for its strength, lubricity, and electrical insulation properties. Generally, parylene is produced by vapor deposition and polymerization of para-xylylene (or its substituted derivatives). However, any suitable insulating material can be used, for example, fluorinated polymers, polyethyleneterephthalate, polyurethane, polyimide, other nonconducting polymers, or the like. Glass or ceramic materials can also be employed. Other materials suitable for use include surface energy modified coating systems such as are marketed under the trade names AMC18, AMC148, AMC141, and AMC321 by Advanced Materials Components Express of Bellafonte, Pa. In some alternative embodiments, however, the working electrode may not require a coating of insulator.

Preferably, the reference electrode 30, which may function as a reference electrode alone, or as a dual reference and counter electrode, is formed from silver, silver/silver chloride and the like. Preferably, the electrodes are juxtapositioned and/or twisted with or around each other; however other configurations are also possible. In one example, the reference electrode 30 is helically wound around the working electrode 38 as illustrated in FIG. 4A. The assembly of wires may then be optionally coated together with an insulating material, similar to that described above, in order to provide an insulating attachment (e.g., securing together of the working and reference electrodes).

As described above, conventional transcutaneous devices are believed to suffer from motion artifact associated with host movement when the host is using the device. For example, when a transcutaneous analyte sensor is inserted into the host, various movements on the sensor (for example, relative movement within and between the subcutaneous space, dermis, skin, and external portions of the sensor) create stresses on the device, which is known to produce artifacts on the sensor signal (e.g., non-constant noise). Accordingly, there are different design considerations (for example, stress considerations) on various sections of the sensor. For example, the in vivo portion of the sensor (e.g., the portion inserted through the host's skin and into the underlying tissue) can benefit in general from greater flexibility as it encounters greater mechanical stresses caused by movement of the tissue within the patient and relative movement between the in vivo and ex vivo portions of the sensor. On the other hand, the ex vivo portion of the sensor (the portion of the sensor that stays outside the body of the host) can benefit in general from a stiffer, more robust design to ensure structural integrity and/or reliable electrical connections. Additionally, in some embodiments wherein a needle is retracted over the ex vivo portion of the device, a stiffer design can minimize crimping of the sensor and/or ease in retraction of the needle from the sensor. Thus, by designing greater flexibility into the in vivo portion, the flexibility is believed to compensate for patient movement, and noise associated therewith. By designing greater stiffness into the ex vivo portion, column strength (for retraction of the needle over the sensor), electrical connections, and integrity can be enhanced. In some alternative embodiments, a stiffer distal end and/or a more flexible proximal end can be advantageous as described in U.S. Patent Publication No. US-2006-0015024-A1 and U.S. Patent Publication No. US-2006-0020187-A1, both of which are incorporated herein by reference in their entirety.

The disclosed embodiments provide an in vivo portion of the sensor that is designed to be more flexible than an ex vivo portion of the sensor. The variable stiffness of the disclosed embodiments can be provided by variable pitch of any one or more helically wound wires of the device, variable cross-section of any one or more wires of the device, and/or variable hardening and/or softening of any one or more wires of the device, such as is described in more detail with reference to U.S. Patent Publication No. US-2006-0015024-A1 and U.S. Patent Publication No. US-2006-0020187-A1, both of which are incorporated herein by reference in their entireties.

In embodiments wherein an outer insulator is disposed, a portion of the coated assembly structure can be stripped or otherwise removed, for example, by hand, excimer lasing, chemical etching, laser ablation, grit-blasting (e.g. with sodium bicarbonate or other suitable grit), or the like, to expose the electroactive surfaces. Alternatively, a portion of the electrode can be masked prior to depositing the insulator in order to maintain an exposed electroactive surface area. In one exemplary embodiment, grit blasting is implemented to expose the electroactive surfaces, preferably utilizing a grit material that is sufficiently hard to ablate the polymer material, while being sufficiently soft so as to minimize or avoid damage to the underlying metal electrode (e.g. a platinum electrode). Although a variety of "grit" materials can be used (e.g. sand, talc, walnut shell, ground plastic, sea salt, and the like), in some preferred embodiments, sodium bicarbonate is an advantageous grit-material because it is sufficiently hard to ablate, e.g. a parylene coating without damaging, e.g. an underlying platinum conductor. One additional advantage of sodium bicarbonate blasting includes its polishing action on the metal as it strips the polymer layer, thereby eliminating a cleaning step that might otherwise be necessary.

In some embodiments, a radial window is formed through the insulating material to expose a circumferential electroactive surface of the working electrode. Additionally, sections of electroactive surface of the reference electrode are exposed. For example, the sections of electroactive surface can be masked during deposition of an outer insulating layer or etched after deposition of an outer insulating layer. In some applications, cellular attack or migration of cells to the sensor can cause reduced sensitivity and/or function of the device, particularly after the first day of implantation. However, when the exposed electroactive surface is distributed circumferentially about the sensor (e.g. as in a radial window), the available surface area for reaction can be sufficiently distributed so as to minimize the effect of local cellular invasion of the sensor on the sensor signal. Alternatively, a tangential exposed electroactive window can be formed, for example, by stripping only one side of the coated assembly structure. In other alternative embodiments, the window can be provided at the tip of the coated assembly structure such that the electroactive surfaces are exposed at the tip of the sensor. Other methods and configurations for exposing electroactive surfaces can also be employed.

Preferably, the above-exemplified sensor has an overall diameter of not more than about 0.020 inches (about 0.51 mm), more preferably not more than about 0.018 inches (about 0.46 mm), and most preferably not more than about 0.016 inches (0.41 mm). In some embodiments, the working electrode has a diameter of from about 0.001 inches or less to about 0.010 inches or more, preferably from about 0.002 inches to about 0.008 inches, and more preferably from about 0.004 inches to about 0.005 inches. The length of the window can be from about 0.1 mm (about 0.004 inches) or less to about 2 mm (about 0.078 inches) or more, and preferably from about 0.5 mm (about 0.02 inches) to about 0.75 mm (0.03 inches). In such embodiments, the exposed surface area of the working electrode is preferably from about 0.000013 $in^2$ (0.0000839 $cm^2$) or less to about 0.0025 $in^2$ (0.016129 $cm^2$) or more (assuming a diameter of from about 0.001 inches to about 0.010 inches and a length of from about 0.004 inches to about 0.078 inches). The exposed surface area of the working electrode is selected to produce an analyte signal with a current in the picoAmp range, such as is described in more detail elsewhere herein. However, a current in the picoAmp range can be dependent upon a variety of factors, for example the electronic circuitry design (e.g. sample rate, current draw, A/D converter bit resolution, etc.), the membrane system (e.g. permeability of the analyte through the membrane system), and the exposed surface area of the working electrode. Accordingly, the exposed electroactive working electrode surface area can be selected to have a value greater than or less than the above-described ranges taking into consideration alterations in the membrane system and/or electronic circuitry. In preferred embodiments of a glucose sensor, it can be advantageous to minimize the surface area of the working electrode while maximizing the diffusivity of glucose in order to optimize the signal-to-noise ratio while maintaining sensor performance in both high and low glucose concentration ranges.

In some alternative embodiments, the exposed surface area of the working (and/or other) electrode can be increased by altering the cross-section of the electrode itself For example, in some embodiments the cross-section of the working electrode can be defined by a cross, star, cloverleaf, ribbed, dimpled, ridged, irregular, or other non-circular configuration; thus, for any predetermined length of electrode, a specific increased surface area can be achieved (as compared to the area achieved by a circular cross-section). Increasing the surface area of the working electrode can be advantageous in providing an increased signal responsive to the analyte concentration, which in turn can be helpful in improving the signal-to-noise ratio, for example.

In some alternative embodiments, additional electrodes can be included within the assembly, for example, a three-electrode system (working, reference, and counter electrodes) and/or an additional working electrode (e.g. an electrode which can be used to generate oxygen, which is configured as a baseline subtracting electrode, or which is configured for measuring additional analytes). U.S. Pat. No. 7,081,195, U.S. Patent Publication No. US-2005-0143635-A1, and U.S. Patent Publication No. US-2007-0027385-A1, each of which are incorporated by reference herein, describe some systems and methods for implementing and using additional working, counter, and/or reference electrodes. In one implementation wherein the sensor comprises two working electrodes, the two working electrodes are juxtapositioned (e.g. extend parallel to each other), around which the reference electrode is disposed (e.g. helically wound). In some embodiments wherein two or more working electrodes are provided, the working electrodes can be formed in a double-, triple-, quad-, etc. helix configuration along the length of the sensor (for example, surrounding a reference electrode, insulated rod, or other support structure). The resulting electrode system can be configured with an appropriate membrane system, wherein the first working electrode is configured to measure a first signal comprising glucose and baseline and the additional working electrode is configured to measure a baseline signal consisting of baseline only (e.g. configured to be substantially similar to the first working electrode without an enzyme disposed thereon). In this way, the baseline signal can be subtracted from the first signal to produce a glucose-only signal that is substantially not subject to fluctuations in the baseline and/or interfering species on the signal. Accordingly, the above-described dimensions can be altered as desired.

Co-pending U.S. patent application Ser. No. 11/543,396, filed Oct. 4, 2006, and entitled "ANALYTE SENSOR" and U.S. Patent Publication No. US-2005-0245799-A1, which are incorporated by reference herein, describe additional configurations for use in different bodily locations. In one exemplary embodiment, the sensor is configured for transcutaneous implantation in the host. In another exemplary embodiment, the sensor is configured for insertion into the circulatory system, such as a peripheral vein or artery. However, in other embodiments, the sensor is configured for insertion into the central circulatory system, such as but not limited to the vena cava. In still other embodiments, the sensor can be configured for insertion into an extracorporeal circulation system, such as but not limited to a shunt (e.g., from an artery to a vein), an extracorporeal blood chemistry analysis device, a dialysis machine or a heart-lung machine (e.g., pumps the blood during heart surgery). In still another embodiment, the sensor can be configured to be wholly implantable, as is described in U.S. Pat. No. 6,001,067, incorporated herein by reference.

Although some embodiments illustrate one electrode configuration including one bulk metal wire helically wound around another bulk metal wire, other electrode configurations are also contemplated. In an alternative embodiment, the working electrode comprises a tube with a reference electrode disposed or coiled inside, including an insulator therebetween. Alternatively, the reference electrode comprises a tube with a working electrode disposed or coiled inside, including an insulator therebetween. In another alternative embodiment, a polymer (e.g., insulating) rod is provided, wherein the electrodes are deposited (e.g., electro-plated) thereon. In yet another alternative embodiment, a metallic (e.g., steel) rod is provided, coated with an insulating material, onto which the working and reference electrodes are deposited. In yet another alternative embodiment, one or more working electrodes are helically wound around a reference electrode.

While the methods of preferred embodiments are especially well suited for use with small structured-, micro- or small diameter sensors, the methods can also be suitable for use with larger diameter sensors, e.g., sensors of 1 mm to about 2 mm or more in diameter.

FIG. 4B is a cross-sectional view through the sensor of FIG. 4A on line 4B-4B, illustrating the membrane system 32 in one embodiment. In this embodiment, the membrane system includes an electrode domain 43, an interference domain 44, and enzyme domain 46, and a diffusion resistance domain 48 wrapped around the platinum wire working electrode 38. In some embodiments, this membrane system also includes a cell impermeable domain as described elsewhere herein. In some embodiments, a unitary resistance domain and cell impermeable domain is included in the membrane system (denoted as the resistance domain 48 in this illustration). In some embodiments, the transcutaneous wire sensor is configured for short-term implantation (e.g., 1-30 days).

Figure 4C:
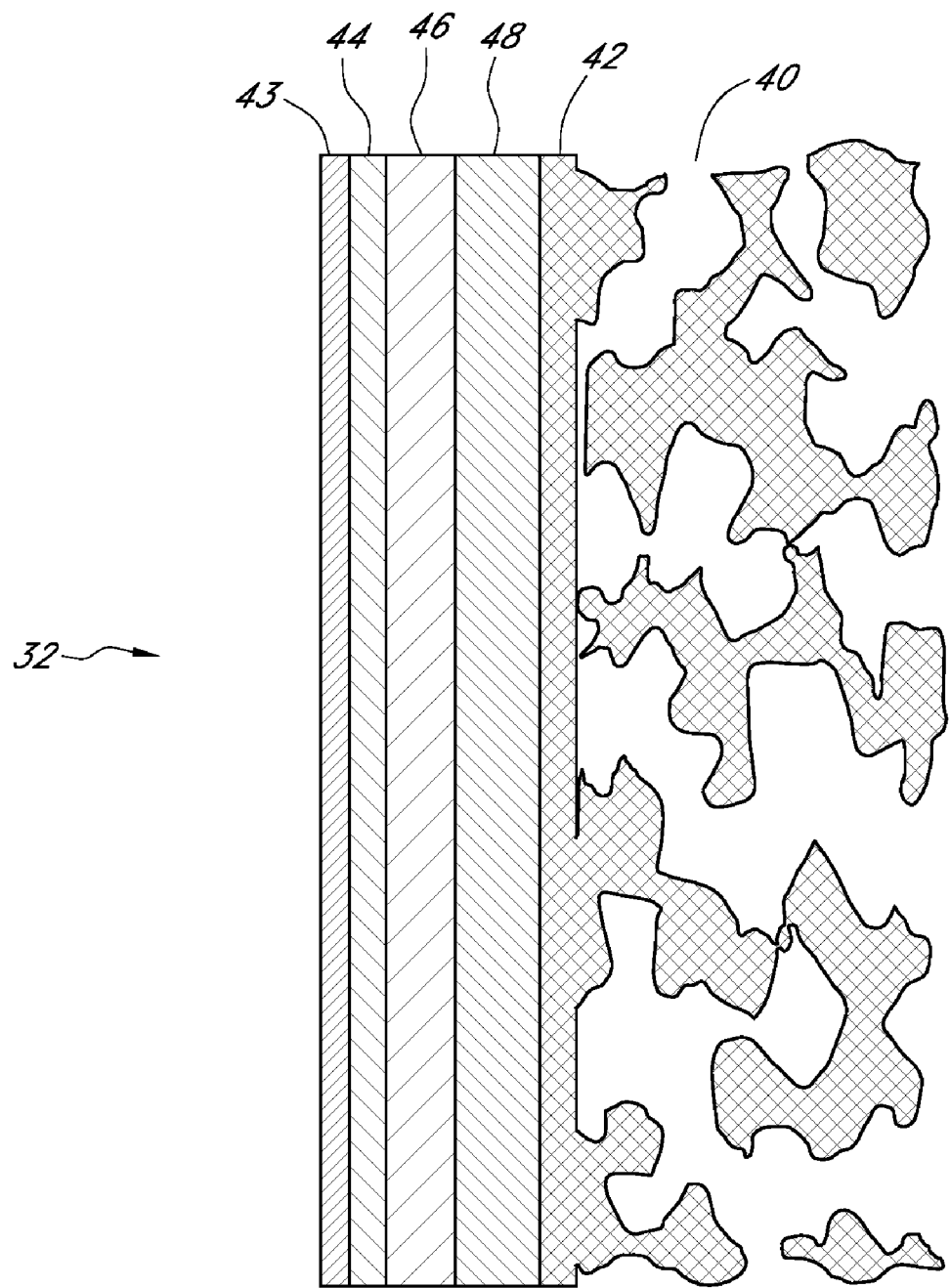
FIG. 4C is a cross-sectional view of an exemplary embodiment of the sensor membrane system, including a biointerface membrane.

FIG. 4C is an illustration of a cross-section of a membrane system 32 in an alternative embodiment. The membrane system 32 can be used with a glucose sensor such as those described herein. In this embodiment, the membrane system 32 includes an electrode domain 43 most proximal to the electrochemically reactive surfaces of the working electrode; an (optional) interference domain 44 less proximal to the electrochemically reactive surfaces of the working electrode than the electrode domain; an enzyme domain 46 less proximal to the electrochemically reactive surfaces of the working electrode than the interference domain; a diffusion resistance domain 48 less proximal to the electrochemically reactive surfaces of the working electrode than the enzyme domain; a cell impermeable domain 42 (also referred to as a bioprotective layer) less proximal to the electrochemically reactive surfaces of the working electrode than the diffusion resistance domain; and an optional cell disruptive domain 40 most distal of all domains from the electrochemically reactive surfaces of the working electrode. However, it is understood that the membrane system 32 can be modified for use in other devices, by including only two or more of the layers, or additional layers not recited above.

In general, the sensing membranes 32 of some embodiments include a plurality of domains or layers, for example, an interference domain 44, an enzyme domain 46, and a resistance domain 48, and may include additional domains, such as an electrode domain 43, a cell impermeable domain 42 (also referred to as a bioprotective layer), and/or an oxygen domain (not shown), such as described in more detail in the above-cited U.S. patent publications. However, it is understood that a sensing membrane modified for other sensors, for example, by including fewer or additional domains is within the scope of some embodiments. In some embodiments, one or more domains of the sensing membranes are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly (propylene oxide) and copolymers and blends thereof, polysulfones and block copolymers thereof including, for example, di-block, tri-block, alternating, random and graft copolymers. U.S. Patent Publication No. US-2005-024579912-A1, which is incorporated herein by reference in its entirety, describes biointerface and sensing membrane configurations and materials that may be applied to some embodiments.

The sensing membrane can be deposited on the electroactive surfaces of the electrode material using known thin or thick film techniques (for example, spraying, electro-depositing, dipping, or the like). It is noted that the sensing membrane that surrounds the working electrode does not have to be the same structure as the sensing membrane that surrounds a reference electrode, etc. For example, the enzyme domain deposited over the working electrode does not necessarily need to be deposited over the reference and/or counter electrodes.

Sensing Membrane

Preferably, a sensing membrane 32 (e.g., a membrane system) is disposed over the electroactive surfaces of the sensor 34 and includes one or more domains or layers (FIG. 4B-4C). In general, the sensing membrane 32 functions to control the flux of a biological fluid there through and/or to protect sensitive regions of the sensor from contamination by the biological fluid, for example. Some conventional electrochemical enzyme-based analyte sensors generally include a sensing membrane that controls the flux of the analyte being measured, protects the electrodes from contamination by the biological fluid, and/or provides an enzyme that catalyzes the reaction of the analyte with a co-factor, for example. See, e.g. U.S. Patent Publication No. US-2005-0245799-A1 and U.S. Patent Publication No. US-2006-0020187-A1, which are incorporated herein by reference in their entirety.

The sensing membranes 32 of some embodiments can include any membrane configuration suitable for use with any analyte sensor (such as described in more detail herein). In general, the sensing membranes of some embodiments include one or more domains, all or some of which can be adhered to or deposited on the analyte sensor as is appreciated by one skilled in the art. In one embodiment, the sensing membrane generally provides one or more of the following functions: 1) protection of the exposed electrode surface from the biological environment, 2) diffusion resistance (limitation) of the analyte, 3) a catalyst for enabling an enzymatic reaction, 4) limitation or blocking of interfering species, and 5) hydrophilicity at the electrochemically reactive surfaces of the sensor interface, such as described in the herein-referenced co-pending U.S. patent publications.

The membrane system 32 of some embodiments, which are described in more detail herein with reference to FIGS. 4B-4C, is formed at least partially from silicone materials comprising a hydrophile and configured to allow glucose/analyte transport. In some embodiments, the silicone material comprises a non-silicon-containing hydrophile. In some embodiments, the silicone material comprises a "micellar jacket" structure, which is described elsewhere herein. The membranes described herein are generally non-porous and semipermeable, and comprise a monolithic, homogenous structure that allows the passage of a substance (e.g., glucose, $H_2O_2$, acetaminophen, ascorbate, etc.) through the membrane, depending upon the selective dissolution and diffusion of the substance as a solute through a non-porous film. The term "monolithic" as used herein is a broad term, and is to be given its ordinary and customary meaning to a person of ordinary skill in the art (and is not to be limited to a special or customized meaning), and refers without limitation to being substantially non-porous and having a generally unbroken surface. The term "homogeneous" as used herein, with reference to a membrane, is a broad term, and is to be given its ordinary and customary meaning to a person of ordinary skill in the art (and is not to be limited to a special or customized meaning), and refers without limitation to having substantially uniform characteristics from one side of the membrane to the other. A membrane can have heterogeneous structural domains, for example, created by using block copolymers (e.g., polymers in which different blocks of identical monomer units alternate with each other), and still be characterized functionally as homogenous with respect to its dependence upon dissolution rather than sieving to effect separation of substances. A monolithic membrane can thus be used to selectively separate components of a solution on the basis of properties other than the size, shape and density of the diffusion substances. Monolithic, homogeneous membranes act as a barrier because of the preferential diffusion therethrough of some substances. Formation of monolithic, homogeneous membranes is discussed in U.S. Pat. No. 4,803,243 and No. 4,686,044, herein incorporated by reference.

While not being bound by any particular theory, it is believed that silicone materials provided herein enhance biostability when compared to other polymeric materials such as polyurethane. In embodiments wherein more than one silicone layer is located adjacent to another silicone layer, the use of silicone can promote bonding together of the layers. The silicone membranes of the present invention have high oxygen permeability, thus promoting oxygen transport to the enzyme domain. Finally, the membranes of the present invention promote analyte transport to the enzyme domain via dissolution and diffusion of the analyte in the micellar jacket structure of the membrane (described in detail below).

Electrode Domain

In some embodiments, the membrane system 32 comprises an optional electrode domain 43 (FIGS. 2B-2C). The electrode domain is provided to ensure that an electrochemical reaction occurs between the electroactive surfaces of the working electrode and the reference electrode, and thus the electrode domain is preferably situated more proximal to the electroactive surfaces than other membrane layers (e.g., 44, 46, 48, etc.). Preferably, the electrode domain 43 includes a semipermeable coating that maintains a layer of water at the electrochemically reactive surfaces of the sensor, for example, a humectant in a binder material can be employed as an electrode domain; this allows for the full transport of ions in the aqueous environment. The electrode domain can also assist in stabilizing the operation of the sensor by overcoming electrode start-up and drifting problems caused by inadequate electrolyte. The material that forms the electrode domain can also protect against pH-mediated damage that can result from the formation of a large pH gradient due to the electrochemical activity of the electrodes.

In one embodiment, the electrode domain 43 includes a flexible, water-swellable, hydrogel film having a "dry film" thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. "Dry film" thickness refers to the thickness of a cured film cast from a coating formulation by standard coating techniques.

In certain embodiments, the electrode domain 43 is formed of a curable mixture of a urethane polymer and a hydrophilic polymer. For example, some coatings are formed of a polyurethane polymer having carboxylate functional groups and non-ionic hydrophilic polyether segments, wherein the polyurethane polymer is crosslinked with a water-soluble carbodiimide (e.g., 1-ethyl-3-(3-dimethylaminopropyl)carbodiimide (EDC)) in the presence of polyvinylpyrrolidone and cured at a moderate temperature of about 50° C. In some alternative embodiments, the electrode domain 43 is formed from high oxygen soluble materials such as polymers formed from silicone, fluorocarbons, perfluorocarbons, or the like.

In some embodiments, the electrode domain 43 is deposited by spray or dip-coating the electroactive surfaces of the sensor. In other embodiments, the electrode domain is formed by dip-coating the electroactive surfaces in an electrode solution and curing the domain for a time from about 15 minutes to about 30 minutes at a temperature of from about 40° C. to about 55° C. (and can be accomplished under vacuum (e.g., from 20 to 30 mmHg)). In embodiments wherein dip coating is used to deposit the electrode domain, a preferred insertion rate of from about 1 inches per minute to about 3 inches per minute, with a preferred dwell time of from about 0.5 minutes to about 2 minutes, and a preferred withdrawal rate of from about 0.25 inches per minute to about 2 inches per minute provide a functional coating. However, values outside of those set forth above can be acceptable or even desirable in certain embodiments, for example, dependent upon viscosity and surface tension as is appreciated by one skilled in the art. In one embodiment, the electroactive surfaces of the electrode system are dip-coated one time (one layer) and cured at 50° C. under vacuum for 20 minutes. In alternative embodiments, the electroactive surfaces of the electrode system are dip-coated a second time (2 layers) and cured.

Although an independent electrode domain 43 is described herein, in some embodiments, sufficient hydrophilicity can be provided in the interference domain 44 (optional) and/or enzyme domain 46 so as to provide for the full transport of ions in the aqueous environment (e.g. without a distinct electrode domain).

In some embodiments, the electrode domain includes a blend of a silicone material and a hydrophilic polymer (e.g., a hydrophilic-hydrophobic polymer, such as but not limited to a PLURONIC® polymer). In a preferred embodiment, the blend is a substantial blend. In another preferred embodiment, the blend forms a micellar jacket structure. Depending upon the embodiment, the remaining membrane domains (e.g., interference domain, enzyme domain, resistance domain, or cell impermeable domain) may or may not include a silicone/hydrophilic-hydrophobic polymer blend, such as those described herein to form a micellar jacket structure. In one embodiment, the electrode domain is the only domain of the membrane system to include a silicone/hydrophilic-hydrophobic polymer blend. In other embodiments, two or more of the membrane system domains include a silicone/hydrophilic-hydrophobic polymer blend. In preferred embodiments, the silicone/hydrophilic-hydrophobic polymer blend, of which the one, two or more domains are formed, forms a micellar jacket structure.

Interference Domain

In some embodiments, an optional interference domain 44 is provided, which generally includes a polymer domain that restricts or substantially blocks the flow of one or more interferants therethrough (FIGS. 4B-4C). In some embodiments, the interference domain 44 functions as a molecular sieve that allows the passage therethrough of analytes and/or other substances that are to be measured by the electrodes, while preventing passage of other substances, including interferants such as ascorbate and urea (see U.S. Pat. No. 6,001,067 to Shults). Some known interferants for a glucose-oxidase based electrochemical sensor include acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid.

Several polymer types can be utilized as a base material for the interference domain 44 including polyurethanes, polymers having pendant ionic groups, and polymers having controlled pore size, for example. In one embodiment, the interference domain includes a thin, hydrophobic membrane that is non-swellable and restricts diffusion of higher molecular weight species. The interference domain is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of some embodiments are described in U.S. Pat. No. 7,074,307 and U.S. Pat. No. 7,081,195, U.S. Patent Publication No. US-2005-0176136-A1, and U.S. Patent Publication No. US-2005-0143635-A1, incorporated herein by reference in their entireties. In some alternative embodiments, a distinct interference domain is not included.

In some embodiments, the optional interference domain 44 comprises one or more cellulosic derivatives, such as but not limited to polymers such as cellulose acetate, cellulose acetate butyrate, 2-hydroxyethyl cellulose, cellulose acetate phthalate, cellulose acetate propionate, cellulose acetate trimellitate, and the like. In some alternative embodiments, more than one cellulosic derivative can be used to form the interference domain. In general, the formation of the interference domain on a surface (e.g., using known thin-film techniques) utilizes a solvent or solvent system in order to solvate the cellulosic derivative (or other polymer) prior to film formation thereon. In some embodiments, acetone and ethanol are used as solvents for cellulose acetate; however one skilled in the art appreciates the numerous solvents that are suitable for use with cellulosic derivatives (and other polymers). Additionally, one skilled in the art appreciates that the preferred relative amounts of solvent can be dependent upon the cellulosic derivative (or other polymer) used, its molecular weight, its method of deposition, its desired thickness, and the like. However, a percent solute of from about 1% to about 25% is preferably used to form the interference domain solution so as to yield an interference domain having the desired properties. The cellulosic derivative (or other polymer) used, its molecular weight, method of deposition, and desired thickness can be adjusted, depending upon one or more other of the parameters, and can be varied accordingly as is appreciated by one skilled in the art. A detailed description of the use of cellulosic derivatives can be found in U.S. Patent Publication No. US-2006-0229512-A1, co-pending U.S. patent application Ser. No. 11/654,140, filed on Jan. 17, 2007, and entitled "MEMBRANES FOR AN ANALYTE SENSOR", and co-pending U.S. patent application Ser. No. 11/654,327 filed on Jan. 17, 2007, and entitled "MEMBRANES FOR AN ANALYTE SENSOR", which are incorporated herein by reference.

In some alternative embodiments, the interference domain 44 comprises a high oxygen soluble polymer, such as described herein.

In some embodiments, the interference domain 44 is deposited onto the electrode domain 43 (or directly onto the electroactive surfaces when a distinct electrode domain is not included) for a domain thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. Thicker membranes can also be useful, but thinner membranes are generally preferred because they have a lower impact on the rate of diffusion of hydrogen peroxide from the enzyme membrane to the electrodes. Unfortunately, the thin thickness of the interference domains conventionally used can introduce variability in the membrane system processing. For example, if too much or too little interference domain is incorporated within a membrane system, the performance of the membrane can be adversely affected.

In some alternative embodiments, the interference domain includes a blend of a silicone material and a hydrophilic polymer (e.g., a hydrophilic-hydrophobic polymer, such as but not limited to a PLURONIC® polymer). In a preferred embodiment, the blend is a substantial blend. In another preferred embodiment, the blend forms a micellar jacket structure. Depending upon the embodiment, the remaining domains (e.g., electrode domain, enzyme domain, resistance domain or cell impermeable domain) of the membrane system may or may not include a silicone/hydrophilic-hydrophobic polymer blend, such as those described herein to form a micellar jacket structure. In one embodiment, the interference domain is the only domain of the membrane system to include a silicone/hydrophilic-hydrophobic polymer blend. In some embodiments, two or more of the membrane system domains include a silicone/hydrophilic-hydrophobic polymer blend. In preferred embodiments, the silicone/hydrophilic-hydrophobic polymer blend, of which the one, two or more domains are formed, forms a micellar jacket structure.

Enzyme Domain

Again referring to FIGS. 4B-4C, the membrane system includes an enzyme domain 46 disposed more distally from the electroactive surfaces than the interference domain (or electrode domain when a distinct interference domain is not included). In some embodiments, the enzyme domain is directly deposited onto the electroactive surfaces (when neither an electrode domain nor an interference domain is included). In some embodiments, the enzyme domain provides an enzyme to catalyze the reaction of the analyte and its co-reactant, as described in more detail herein. In some embodiments, the enzyme domain includes glucose oxidase (GOX); however other oxidases, for example, galactose oxidase or urate oxidase, can also be used.

For an enzyme-based electrochemical glucose sensor to perform well, the sensor's response is preferably limited by neither enzyme activity nor co-reactant concentration. Because enzymes, including GOX, are subject to deactivation as a function of time even in ambient conditions, this behavior is compensated for, in forming the enzyme domain. In some embodiments, the enzyme domain 46 is constructed of aqueous dispersions of colloidal polyurethane polymers including the enzyme. However, in alternative embodiments the enzyme domain is constructed from an oxygen enhancing material, for example, silicone, or fluorocarbon, in order to provide a supply of excess oxygen during transient ischemia. Preferably, the enzyme is immobilized within the domain. See U.S. Patent Publication No. US-2005-0054909-A1.

In some embodiments, the enzyme domain 46 is deposited onto the interference domain for a domain thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. However in some embodiments, the enzyme domain is deposited onto the electrode domain or directly onto the electroactive surfaces. In some embodiments, the enzyme domain is deposited by spray or dip coating. In one embodiment, the enzyme domain is formed by dip-coating the electrode domain into an enzyme domain solution and curing the domain for from about 15 minutes to about 30 minutes at a temperature of from about 40° C. to about 55° C. (and can be accomplished under vacuum (e.g. 20 to 30 mmHg)). In one exemplary embodiment wherein dip-coating is used to deposit the enzyme domain at room temperature, an insertion rate from about 1 inch per minute to about 3 inches per minute, with a dwell time of from about 0.5 minutes to about 2 minutes, and a withdrawal rate of from about 0.25 inch per minute to about 2 inches per minute provides a functional coating. However, values outside of those set forth above can be acceptable or even desirable in certain embodiments, for example, dependent upon viscosity and surface tension as is appreciated by one skilled in the art. In one embodiment, the enzyme domain is formed by dip coating two times (namely, forming two layers) in a coating solution and curing at 50° C. under vacuum for 20 minutes. However, in some other embodiments, the enzyme domain can be formed by dip-coating and/or spray-coating one or more layers at a predetermined concentration of the coating solution, insertion rate, dwell time, withdrawal rate, and/or desired thickness.

In some embodiments, the enzyme domain 46 is formed from high oxygen soluble materials such as polymers formed from silicone, fluorocarbons, perfluorocarbons, or the like. In one embodiment, the enzyme domain is formed from a silicone composition with a hydrophile such as such as polyethylene glycol, propylene glycol, pyrrolidone, esters, amides, carbonates, or polypropylene glycol covalently incorporated or grafted therein. In some embodiments, the silicone composition comprises a non-silicon-containing hydrophile.

In one preferred embodiment, high oxygen solubility within the enzyme domain 46 can be achieved by using a polymer matrix to host the enzyme within the enzyme domain, which has a high solubility of oxygen. In one exemplary embodiment of fluorocarbon-based polymers, the solubility of oxygen within a perfluorocarbon-based polymer is 50-volume %. As a reference, the solubility of oxygen in water is approximately 2-volume %.

Utilization of a high oxygen solubility material for the enzyme domain is advantageous because the oxygen dissolves more readily within the domain and thereby acts as a high oxygen soluble domain optimizing oxygen availability to oxygen-utilizing sources (for example, the enzyme and/or counter electrode). When the resistance domain 48 and enzyme domain 46 both comprise a high oxygen soluble material (e.g., a silicone polymer as discussed herein), the chemical bond between the enzyme domain 46 and resistance domain 48 can be optimized, and the manufacturing made easy.

In alternative embodiments, the enzyme domain 46 comprises a silicone composition, wherein the silicone composition surrounds the enzyme. When the resistance domain 48 and enzyme domain 46 both comprise a silicone material (whether the silicone material composition is the same or different), the chemical bond between the enzyme domain 46 and resistance domain 48 is optimal, and the manufacturing made easy. Utilization of a silicone material, such as the silicone composition of some embodiments described herein, for the enzyme domain is also advantageous because silicone acts as an oxygen antenna domain and optimizes oxygen transport through the membrane to selected locations (for example, the enzyme membrane and/or counter electrode). In one embodiment, the enzyme domain comprises a silicone material and PEG. The PEG can include from about 1 repeating unit to about 60 repeating units, more preferably from about 1, 2, 3, 4, 5, 6, 7, 8, 9, 10, 11, 12, 13, 14, or 15 repeating units to about 45, 46, 47, 48, 49, 50, 51, 52, 53, 54, 55, 56, 57, 58, or 50 repeating units, and most preferably from about 16, 17, 18, 19, 20, 21, 22, 23, 24, 25, 26, 27, 28, 29, or 30 repeating units to about 31, 32, 33, 34, 35, 36, 37, 38, 39, 40, 41, 42, 43, or 44 repeating units. Other hydrophiles that can be added to the silicone composition include but are not limited to other glycols such as propylene glycol, pyrrolidone, esters, amides, carbonates, and polypropylene glycol. In various embodiments, the PEG or other hydrophile comprises from about 0 wt. % to about 35, 40, 45, 50, 55, 60, 65, or 70 wt. % or more of the enzyme domain, more preferably from about 1, 2, or 3 wt. % to about 15, 16, 17, 18, 19, 20, 21, 22, 23, 24, 25, 26, 27, 28, 29, or 30 wt. %, and most preferably from about 4, 5, or 6 wt. % to about 7, 8, 9, 10, 11, 12, 13, or 14 wt. %. In one exemplary embodiment, the enzyme domain comprises 6 wt. % polyethylene glycol. Exemplary descriptions of the use of silicone in the enzyme domain can be found in U.S. Patent Publication No. US-2005-0090607-A1 and U.S. Patent Publication No. US-2005-0054909-A1, both of which are incorporated herein by reference.

In some embodiments, the enzyme domain comprises a blend of a silicone polymer with a hydrophilic polymer, such as but not limited to a silicone-PLURONIC® polymer blend. See Co-pending U.S. patent application Ser. No. 11/404,417, filed on Apr. 14, 2006, and entitled "SILICONE BASED MEMBRANES FOR USE IN IMPLANTABLE GLUCOSE SENSORS," which is incorporated herein in its entirety, and the description below. In some alternative embodiments, the enzyme domain includes a blend of a silicone material and a hydrophilic polymer (e.g., a hydrophilic-hydrophobic, such as but not limited to a PLURONIC® polymer). In a preferred embodiment, the blend is a substantial blend. In another preferred embodiment, the blend forms a micellar jacket structure. Depending upon the embodiment, the remaining domains (e.g., electrode domain, interference domain, resistance domain or cell impermeable domain) of the membrane system may or may not include a silicone/hydrophilic-hydrophobic polymer blend, such as those described herein to form a micellar jacket structure. In one embodiment, the enzyme domain is the only domain of the membrane system to include a silicone/hydrophilic-hydrophobic polymer blend. In some embodiments, two or more of the membrane system domains include a silicone/hydrophilic-hydrophobic polymer blend. In preferred embodiments, the silicone/hydrophilic-hydrophobic polymer blend, of which the one, two or more domains are formed, forms a micellar jacket structure.

Resistance Domain

In some embodiments, the membrane system includes a resistance domain 48 (also referred to herein as the diffusion resistance domain) disposed more distal from the electroactive surfaces than the enzyme domain 46 (FIGS. 4B-4C). Although the following description is directed to a resistance domain for a glucose sensor, the resistance domain can be modified for other analytes and co-reactants, as is appreciated by one skilled in the art.

In contrast to the about 1:1 molar ratio of oxygen to glucose in whole blood, there exists a molar excess of glucose relative to the amount of oxygen in interstitial fluid; that is, for every free oxygen molecule in extracellular fluid, there are typically more than about 100-200 glucose molecules present (see Updike et al., Diabetes Care 5:207-21(1982)). However, an immobilized enzyme-based glucose sensor employing oxygen as co-reactant is preferably supplied with oxygen in non-rate-limiting excess in order for the sensor to respond linearly to changes in glucose concentration, while not responding to changes in oxygen concentration. Specifically, when a glucose-monitoring reaction is oxygen limited, linearity is not achieved above minimal concentrations of glucose. Without a semipermeable membrane situated over the enzyme domain to control the flux of glucose and oxygen, a linear response to glucose levels can be obtained only for glucose concentrations of up to about 40 mg/dL. However, in a clinical setting, a linear response to glucose levels is desirable up to at least about 400 mg/dL.

The resistance domain 48 includes a semi-permeable membrane that controls the flux of oxygen and glucose to the underlying enzyme domain, preferably rendering oxygen in a non-rate-limiting excess. As a result, the upper limit of linearity of glucose measurement is extended to a much higher value than that which is achieved without the resistance domain. In one embodiment, the resistance domain exhibits an oxygen to glucose permeability ratio of from about 50:1 or less to about 400:1 or more, preferably about 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)).

In alternative embodiments, a lower ratio of oxygen-to-glucose can be sufficient to provide excess oxygen by using a high oxygen solubility domain (for example, a silicone or fluorocarbon-based material or domain) to enhance the supply/transport of oxygen to the enzyme domain. If more oxygen is supplied to the enzyme, then more glucose can also be supplied to the enzyme without creating an oxygen rate-limiting excess. In alternative embodiments, the resistance domain is formed from a silicone composition, such as is described in U.S. Patent Publication No. US-2005-0090607-A1.

In one exemplary embodiment, the resistance domain 48 is formed from high oxygen soluble materials such as polymers formed from silicone, fluorocarbons, perfluorocarbons, or the like. In another exemplary embodiment, the resistance domain is formed from a silicone composition with a hydrophile such as such as polyethylene glycol, propylene glycol, pyrrolidone, esters, amides, carbonates, or polypropylene glycol covalently incorporated or grafted therein. In some embodiments, the hydrophile is a non-silicon-containing hydrophile. In some alternative embodiments, the resistance domain is formed from polyurethane, for example, a polyurethane urea/polyurethane-block-polyethylene glycol blend. In still other embodiments, the diffusion resistance domain is formed from a monomer, polymer, copolymer, or blend including one or more of lactic acid, glycolic acid, anhydrides, phosphazenes, vinyl alcohol, ethylene vinyl alcohol, acetates, ε-caprolactone, β-hydroxybutyrate, γ-ethyl glutamate, DTH iminocarbonate, Bisphenol A iminocarbonate, sebacic acid, hexadecanoic acid, saccharides, chitosan, hydroxyethyl methacrylate (HEMA), ceramics, hyaluronic acid (HA), collagen, gelatin, starches, hydroxy apatite, calcium phosphates, bioglasses, amino acid sequences, proteins, glycoproteins, protein fragments, agarose, fibrin, n-butylene, isobutylene, dioxanone, nylons, vinyl chlorides, amides, ethylenes, n-butyl methacrylate (BMA), metal matrix composites (MMCs), metal oxides (e.g. aluminum), DETOSU-1,6 HD-t-CDM ortho ester, styrene, and ion implantation or plasma treated surfaces of any of the above.

In some embodiments, the resistance domain 48 can be formed as a unitary and/or homogeneous structure with the cell impermeable domain 42; that is, the inherent properties of the resistance domain 48 can provide the functionality described with reference to the cell impermeable domain 42 such that the cell impermeable domain 42 is incorporated as a part of resistance domain 48. In some embodiments, the combined resistance domain/cell impermeable domain can be bonded to or formed as a skin on the cell disruptive domain 40 during a molding process such as described herein. In another embodiment, the resistance domain 48 is formed as a distinct layer and chemically or mechanically bonded to the cell disruptive domain 40 (if applicable) or the cell impermeable domain 42 (when the resistance domain is distinct from the cell impermeable domain). In still another embodiment, the combined resistance/cell impermeable domain can be deposited (e.g., by dipping, spraying, etc.) over other membrane domains previously cast on the sensor, described in greater detail elsewhere herein.

In some embodiments, the resistance domain 48 is formed from silicone polymer/hydrophilic polymer blends such as described herein. In order to restrict the transport of an aqueous analyte such as glucose, lower concentrations of hydrophilic polymer can be employed. Accordingly, in one embodiment, the concentration of hydrophilic polymer (e.g., PLURONIC® F-127) relative to silicone polymer (e.g., MED-4840) is from about 1% to about 15% in the resistance domain 48 (e.g., from about 6% to about 10%). See co-pending U.S. patent application Ser. No. 11/404,417, filed on Apr. 14, 2006 and entitled "SILICONE BASED MEMBRANES FOR USE IN IMPLANTABLE GLUCOSE SENSORS" and incorporated herein by reference. In some embodiments, the silicone polymer/hydrophilic polymer blend includes a micellar jacket structure, such as that discussed elsewhere herein. In some embodiment, a resistance domain, which is formed of a blend of a silicone elastomer and a hydrophilic copolymer, can be deposited between a cell impermeable domain and the electroactive surface. In one exemplary embodiment, the cell impermeable domain and the resistance domain are deposited as a single domain (e.g., not separate domains or layers) that both restricts the flux of the analyte (e.g., glucose) into the membrane system and prevents cellular ingress into the membrane system. In some embodiments, the silicone material (e.g., silicone polymer/hydrophilic polymer blends, such as described with reference to the cell impermeable domain and/or the resistance domain) includes a micellar jacket (e.g., a micellar jacket structure). In some embodiments the silicone material is formed of a silicone composition and a hydrophile and at least a portion of the hydrophilic is covalently incorporated therein. Depending upon the embodiment, the remaining domains (e.g., electrode domain, interference domain, enzyme domain or cell impermeable domain) of the membrane system may or may not include a silicone/hydrophilic-hydrophobic polymer blend, such as those described herein to form a micellar jacket structure. In one embodiment, the resistance domain is the only domain of the membrane system to include a silicone/hydrophilic-hydrophobic polymer blend. In some embodiments, two or more of the membrane system domains include a silicone/hydrophilic-hydrophobic polymer blend. In preferred embodiments, the silicone/hydrophilic-hydrophobic polymer blend, of which the one, two or more domains are formed, forms a micellar jacket structure.

In some alternative embodiments, the resistance domain 48 includes a polyurethane membrane with both hydrophilic and hydrophobic regions to control the diffusion of glucose and oxygen to an analyte sensor, the membrane being easily and reproducibly fabricated from commercially available materials. A suitable hydrophobic polymer component is a polyurethane, or polyetherurethaneurea. Polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Preferred diisocyanates include but are not limited to aliphatic diisocyanates containing from about 4 to about 8 methylene units. Diisocyanates containing cycloaliphatic moieties can also be useful in the preparation of the polymer and copolymer components of the membranes of some embodiments. The material that forms the basis of the hydrophobic matrix of the resistance domain 48 can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In still other embodiments, polyethylene oxide (PEO) is the hydrophilic polymer component of the resistance domain 48. For example, one useful hydrophobic-hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

In various embodiments, the resistance domain 48 is deposited onto the enzyme domain 46 to yield a domain thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. In some embodiments, the resistance domain 48 is deposited onto the enzyme domain 46 by spray coating or dip coating. In certain embodiments, spray coating is the preferred deposition technique. The spraying process atomizes and mists the solution, and therefore most or all of the solvent is evaporated prior to the coating material settling on the underlying domain, thereby minimizing contact of the solvent with the enzyme. One additional advantage of spray-coating the resistance domain as described in some embodiments includes formation of a membrane system that substantially blocks or resists ascorbate (a known electrochemical interferant in hydrogen peroxide-measuring glucose sensors). While not wishing to be bound by theory, it is believed that during the process of depositing the resistance domain as described in some embodiments, a structural morphology is formed, which is characterized in that ascorbate does not substantially permeate there through.

In some embodiments, the resistance domain 48 is deposited on the enzyme domain 46 by spray-coating a solution of from about 1 wt. % to about 5 wt. % polymer and from about 95 wt. % to about 99 wt. % solvent. In spraying a solution of resistance domain material, including a solvent, onto the enzyme domain, it is desirable to mitigate or substantially reduce any contact with enzyme of any solvent in the spray solution that can deactivate the underlying enzyme of the enzyme domain. Tetrahydrofuran (THF) is one solvent that minimally or negligibly affects the enzyme of the enzyme domain upon spraying. Other solvents can also be suitable for use, as is appreciated by one skilled in the art.

Although a variety of spraying or deposition techniques can be used, spraying the resistance domain material and rotating the sensor at least one time by 180° can provide adequate coverage by the resistance domain. Spraying the resistance domain material and rotating the sensor at least two times by 120 degrees provides even greater coverage (one layer of 360° coverage), thereby ensuring resistivity to glucose, such as is described in more detail herein.

In some embodiments, the resistance domain 48 is spray-coated and subsequently cured for a time of from about 15 minutes to about 90 minutes at a temperature of from about 40° C. to about 60° C. (and can be accomplished under vacuum (e.g. from 20 to 30 mmHg)). A cure time of up to about 90 minutes or more can be advantageous to ensure complete drying of the resistance domain. While not wishing to be bound by theory, it is believed that complete drying of the resistance domain aids in stabilizing the sensitivity of the glucose sensor signal. It reduces drifting of the signal sensitivity over time, and complete drying is believed to stabilize performance of the glucose sensor signal in lower oxygen environments.

In one exemplary embodiment, the resistance domain 48 is formed by spray-coating at least six layers (namely, rotating the sensor seventeen times by 120° for at least six layers of 360° coverage) and curing at 50° C. under vacuum for 60 minutes. However, the resistance domain can be formed by dip-coating or spray-coating any layer or plurality of layers, depending upon the concentration of the solution, insertion rate, dwell time, withdrawal rate, and/or the desired thickness of the resulting film.

In an alternative embodiment, the surface of the cured polyurethane-based resistance domain 48 is modified by the application of a hydrophilic polymer solution including a hydrophilic polymer or a polymer containing hydrophilic moieties (e.g., PEG compounds or PLURONIC®) and a solvent (e.g., acetone), to increase sensor sensitivity. In some embodiments, the applied solution (e.g., the hydrophilic polymer solution, including but not limited to a silicone/hydrophilic polymer blend), which is applied over the at least substantially cured polyurethane-based resistance domain 48, forms the cell impermeable domain 42, as described elsewhere herein. In another embodiment, the applied material is a solution of PEG in acetone, such as but not limited to a 10%, 20%, 30%, 40% or more solution of PEG in acetone. For example, in experiments using short-term sensors dipped one time in a 30% solution of PEG in acetone, sensitivity of the treated sensors increased from about 20% to about 75% when compared with non-treated sensors. While not wishing to be bound by theory, it is believed that the surface of a polyurethane resistance domain is responsible for a substantial portion of the domain's analyte resistance capability. It is believed that during the application of the hydrophilic polymer solution, the solvent (e.g., acetone) modifies (e.g., opens up) the surface of the polyurethane resistance domain such that at least a small amount of the hydrophilic polymer can move into (e.g., blend with, become incorporated into) the domain's surface. Due to incorporation of a hydrophilic polymer into the polyurethane resistance domain surface, the surface is rendered more hydrophilic than it was prior to treatment with the hydrophilic polymer solution. The increased surface hydrophilicity (e.g., the surface of a polyurethane resistance domain) produces a corresponding increase in analyte flux into the membrane.

Advantageously, sensors with the membrane system of some embodiments, including an electrode domain 43 and/or interference domain 44, an enzyme domain 46, and a resistance domain 48, provide stable signal response to increasing glucose levels of from about 40 mg/dL to about 400 mg/dL, and sustained function (at least 90% signal strength) even at low oxygen levels (for example, at about 0.6 mg/L $O_2$). While not wishing to be bound by theory, it is believed that the resistance domain 48 provides sufficient resistivity, or the enzyme domain 46 provides sufficient enzyme, such that oxygen limitations are seen at a much lower concentration of oxygen as compared to prior art sensors.

In some embodiments, a sensor signal with a current in the picoAmp range is preferred, which is described in more detail elsewhere herein. However, the ability to produce a signal with a current in the picoAmp range can be dependent upon a combination of factors, including the electronic circuitry design (e.g. A/D converter, bit resolution, and the like), the membrane system (e.g. permeability of the analyte through the resistance domain, enzyme concentration, and/or electrolyte availability to the electrochemical reaction at the electrodes), and the exposed surface area of the working electrode. For example, the resistance domain 48 can be designed to be more or less restrictive to the analyte depending upon to the design of the electronic circuitry, membrane system, and/or exposed electroactive surface area of the working electrode.

Accordingly, in some embodiments, the membrane system is designed with a sensitivity of from about 1 pA/mg/dL to about 100 pA/mg/dL, preferably from about 5 pA/mg/dL to about 25 pA/mg/dL, and more preferably from about 4 pA/mg/dL to about 7 pA/mg/dL. While not wishing to be bound by any particular theory, it is believed that membrane systems designed with a sensitivity in the preferred ranges permit measurement of the analyte signal in low analyte and/or low oxygen situations. Namely, conventional analyte sensors have shown reduced measurement accuracy in low analyte ranges due to lower availability of the analyte to the sensor and/or have shown increased signal noise in high analyte ranges due to insufficient oxygen necessary to react with the amount of analyte being measured. While not wishing to be bound by theory, it is believed that the membrane systems of the preferred embodiments, in combination with the electronic circuitry design and exposed electrochemical reactive surface area design, support measurement of the analyte in the picoAmp range, which enables an improved level of resolution and accuracy in both low and high analyte ranges not seen in the prior art.

Although sensors of some embodiments described herein include an optional interference domain 44 in order to block or reduce one or more interferants, sensors with the membrane system of some embodiments, including an electrode domain 43, an enzyme domain 46, and a resistance domain 48, have been shown to inhibit ascorbate without an additional interference domain. Namely, the membrane system of some embodiments, including an electrode domain, an enzyme domain, and a resistance domain, has been shown to be substantially non-responsive to ascorbate in physiologically acceptable ranges. While not wishing to be bound by theory, it is believed that the process of depositing the resistance domain 48 by spray coating, as described herein, results in a structural morphology that is substantially resistant to ascorbate.

Cell Impermeable Domain

FIG. 4C illustrates the optional cell impermeable domain 42 of the membrane. The cell impermeable domain (also referred to as the bioprotective layer) is impermeable to cells or cell processes, and is composed of a biostable material. In general, the materials preferred for the cell impermeable domain prevent or hinder cell entry or contact with device elements underlying the membrane and prevent or hinder the adherence of cells, thereby further discouraging formation of a barrier cell layer, but permit or facilitate transport of the analyte of interest or a substance indicative of the concentration or presence of the analyte via differential dissolution and diffusion of the solute. Additionally, because of the resistance of the materials to barrier cell layer formation, membranes prepared therefrom are robust long-term in vivo. In one exemplary embodiment, the cell impermeable domain is comprised of a polyurethane and a hydrophilic polymer, such as is described in U.S. Pat. No. 6,862,465 to Shults et al., which is incorporated herein by reference in its entirety. Alternatively, the outermost layer of the sensing membrane 32 can function as a cell impermeable domain 42 (also referred to as the bioprotective layer) and therefore a cell impermeable domain may not be a discrete component of the membrane system 32. In some preferred embodiments, the cell impermeable domain comprises a micellar jacket structure, which is discussed in detail elsewhere herein.

In some embodiments, the cell impermeable domain 42 is positioned more distal to the electroactive surfaces than the resistance domain 48 (or enzyme domain 46, when a distinct resistance domain is not included), and can be resistant to cellular attachment, impermeable to cells, and/or is composed of a biostable material. In alternative embodiments, the resistance domain is omitted and the cell impermeable domain (a single layer) also performs the functions of the resistance domain (e.g., controlling glucose and oxygen flux there through). In some embodiments, the cell impermeable domain 42 is resistant to cellular attachment (for example, attachment by inflammatory cells, such as macrophages, which are therefore kept a sufficient distance from other domains, for example, the enzyme domain), and short-lived chemical oxidizing species, such as but not limited to hypochlorite, in vivo and biodegradation does not occur. Additionally, the materials preferred for forming the cell impermeable domain 42 (also referred to as the bioprotective layer) are resistant to the effects of these oxidative species and have thus been termed biodurable. See, for example, U.S. Pat. No. 6,702,857 and U.S. Patent Publication No. US-2005-0112169-A1, both of which are incorporated herein by reference in their entirety.

In some embodiments, the cell impermeable domain 42 is preferably formed from high oxygen soluble materials such as polymers formed from silicone, fluorocarbons, perfluorocarbons, or the like. In one embodiment, the cell impermeable domain is formed from a silicone composition with a hydrophilic polymer such as such as polyethylene glycol, propylene glycol, pyrrolidone, esters, amides, carbonates, or polypropylene glycol covalently incorporated or grafted therein. In some embodiments, the hydrophile is a non-silicon-containing hydrophile. In still other embodiments, the cell impermeable domain is formed from a monomer, polymer, copolymer, or blend including one or more of: lactic acid, glycolic acid, anhydrides, phosphazenes, vinyl alcohol, ethylene vinyl alcohol, acetates, ε-caprolactone, β-hydroxybutyrate, γ-ethyl glutamate, DTH iminocarbonate, Bisphenol A iminocarbonate, sebacic acid, hexadecanoic acid, saccharides, chitosan, hydroxyethyl methacrylate (HEMA), ceramics, hyaluronic acid (HA), collagen, gelatin, starches, hydroxy apatite, calcium phosphates, bioglasses, amino acid sequences, proteins, glycoproteins, protein fragments, agarose, fibrin, n-butylene, isobutylene, dioxanone, nylons, vinyl chlorides, amides, ethylenes, n-butyl methacrylate (BMA), metal matrix composites (MMCs), metal oxides (e.g. aluminum), DETOSU-1,6 HD-t-CDM ortho ester, styrene, and plasma treated surfaces of any of the above.

In some embodiments, the cell impermeable domain is formed from copolymers or blends of copolymers with hydrophilic polymers having hydrophobic groups, which are referred to herein as hydrophobic-hydrophilic polymers or hydrophilic-hydrophobic polymers (the terms "hydrophobic-hydrophilic polymer" and "hydrophilic-hydrophobic polymer" are used interchangeably herein). In general, the hydrophobic-hydrophilic polymer for use in the blend may be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol, and block copolymers thereof, including, for example, di-block, tri-block, alternating, random and graft copolymers (block copolymers are discussed in U.S. Pat. No. 4,803,243 and U.S. Pat. No. 4,686,044). In some instances, the hydrophobic substituents of the hydrophobic-hydrophilic polymer are its major component; in other instances, the hydrophilic substituents are the major component of the hydrophobic-hydrophilic polymer. For example, in the case of a PEO-PPO-PEO polymer in which all of the PEO and PPO substituents are of substantially equal length, the polymer can be considered to be a predominantly hydrophilic hydrophobic-hydrophilic polymer (also referred to as a hydrophilic polymer) because the PEO is hydrophilic relative to the PPO, and the PEO makes up about two-thirds of the molecule. In another example, such as a PEO-PPO-PEO polymer in which the PPO substituents is substantially longer than the PEO substituents, the polymer may actually be hydrophobic, relative to the first PEO-PPO-PEO polymer, described above.

The hydrophilic and hydrophobic substituents of a polymer can affect the polymer's behavior in certain circumstances, such as but not limited to micellar jackets, which are discussed elsewhere herein. In some embodiments, hydrophilic polymers include hydrophilic-hydrophobic polymers, such as but not limited to hydrophobic polymers comprising at least some hydrophilic groups.

In some embodiments, the cell impermeable domain (also referred to as the bioprotective layer) 42 of the membrane system is formed on a small-structured sensor (e.g., short-term sensor), from a blend of a silicone polymer precursor and a PLURONIC® (e.g., PLURONIC® F127) as described in greater detail elsewhere herein. In some embodiments, the cell impermeable domain 42 is formed directly on the small-structured sensor (e.g., including but not limited to an electrode domain, an interference domain, an enzyme domain and/or a resistance domain previously formed thereon) by dipping the sensor into a cell impermeable domain solution (e.g., a blend of a silicone precursor and a PLURONIC®) and then vulcanizing the material. In other embodiments, the cell impermeable domain 42 is formed separately from the sensor and then wrapped around the sensor. In still other embodiments, the hydrophobic-hydrophilic polymer for use in the blend can be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers. Commercially available examples of PEO and PPO copolymers include the PLURONIC® brand of polymers, which are available from BASF®, Florham Park, N.J., U.S.A. Other suitable PLURONIC® polymers include PPO-PEO-PPO tri-block copolymers (e.g., PLURONIC® products). In still another embodiment, the resistance domain and the cell impermeable domain are a single layer having the functions of both a resistance domain and a cell impermeable domain.

In still other embodiments, the cell impermeable domain 42 is formed from blends of silicone polymers and hydrophilic polymers that have hydrophobic groups (sometimes referred to as hydrophilic-hydrophobic polymers), such as described herein. It is advantageous that the cell impermeable domain 42 has both high oxygen and aqueous analyte solubility so that sufficient analyte reaches the enzyme domain. Accordingly, in one embodiment, the concentration of hydrophilic polymer (e.g., the PEO portion of the PLURONIC® F-127) relative to silicone polymer (e.g., MED-4840) is relatively high, e.g., from about 5% to about 21% PEO in the cell impermeable domain. In one embodiment, the concentration of hydrophilic-hydrophobic polymer (e.g., the PEO) is from about 10% to about 18% (e.g., about 14%). In still another embodiment, the concentration of hydrophilic-hydrophobic polymer (e.g., PEO) is from about 5.5% to about 8.5% in the cell impermeable domain.

The silicone polymer for use in the silicone/hydrophilic-hydrophobic polymer blend can be any suitable silicone polymer. In some embodiments, the silicone polymer is a liquid silicone rubber that may be vulcanized using a metal- (e.g., platinum), peroxide-, heat-, ultraviolet-, or other radiation-catalyzed process. In some embodiments, the silicone polymer is a dimethyl- and methylhydrogen-siloxane copolymer. In some embodiments, the copolymer has vinyl substituents. In some embodiments, commercially available silicone polymers may be used. For example, commercially available silicone polymer precursor compositions may be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydrogen-siloxane copolymers, amorphous silica, a platinum catalyst, a crosslinker, and an inhibitor. The two components may be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation. Silicone polymer/hydrophobic-hydrophilic polymer blends are described in more detail in U.S. patent application Ser. No. 11/404,417, entitled "SILICONE BASED MEMBRANES FOR USE IN IMPLANTABLE GLUCOSE SENSORS," filed on Apr. 14, 2006.

The thickness of the cell impermeable domain 42 is typically about 1 μm or more, preferably from about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200 μm to about 500, 600, 700, 800, 900, or 1000 μm. In preferred embodiments, the thickness of the cell impermeable domain is preferably from about 5, 10, 15 or 20 microns to about 50, 55 or 60 microns. In most preferred embodiments, the cell impermeable domain is from about 10 microns to about 30 microns thick. In still other embodiments, thicker or thinner cell impermeable domains can be desired. Alternatively, the function of the cell impermeable domain is accomplished by the implantable device, or a portion of the implantable device, which may or may not include a distinct domain or layer.

Some conventional membrane domains regulate diffusion therethrough by size exclusion (e.g., blocking diffusion of large, higher molecular weight molecules while allowing diffusion of smaller, low molecular weight molecules.) The inventors have discovered that incorporation of a silicone/hydrophilic-hydrophobic polymer blend material into the membrane system allows transport of a large molecule (e.g., glucose), as described herein, while at the same time blocking transport of a small molecule (e.g., $H_2O_2$ formed outside the membrane system, such as $H_2O_2$ released by macrophages during the wound healing process, which is representative of small molecular weight interferents, such as reactive oxygen species, peroxynitrates and the like), which is discussed elsewhere herein. As a result, the silicone/hydrophilic-hydrophobic polymer blend material both increases analyte-related signal (e.g., glucose signal) and decreases non-constant noise.

While not wishing to be bound by theory, it is believed that, that silicone/hydrophilic-hydrophobic polymer blend materials form micellar jacket structures within the membrane domain(s), which presents a pathway through a predominantly hydrophobic membrane into which water-soluble species (e.g., glucose) can dissolve, and facilitates restricted analyte transport by at least one of two mechanisms. In one mechanism, it is believed that the micellar jacket structure forms a contiguous channel of the hydrophilic substituents (e.g., the PLURONIC® polymers) through the silicone, resulting in a tortuous pathway through the material; the analyte (e.g., glucose) dissolves into the hydrophilic phase of the micellar jackets and then diffuses through the tortuous pathway to the opposite side of the silicone material. In a second mechanism, it is believed that transport of the analyte (e.g., glucose) across the silicone material is energetically driven by a thermodynamic property, such as but not limited to a concentration gradient. In this second mechanism, it is believed that the analyte is driven to "jump" from one micellar jacket to another, thereby traversing the predominantly hydrophobic membrane domain(s); the energy required for the analyte to make that "leap" can be described as a resistance (e.g., to the analyte).

In addition to promoting analyte transport, it is believed that the silicone/hydrophilic-hydrophobic polymer blend material reduces non-constant noise by blocking interfering species. For example, diffusion of small molecular weight interferents (e.g., $H_2O_2$, reactive oxygen species, peroxynitrates, and the like) into the membrane system is believed to be attenuated (e.g., slowed, by thermodynamic incompatibility with the silicone/hydrophilic-hydrophobic material) such that these reactive species self-annihilate and do not substantially reach the electroactive surface. As another example, larger interferent molecules, such as but not limited to Acetaminophen, are blocked from passage through the cell impermeable domain, likely due to steric hindrance and/or thermodynamic trapping. By "thermodynamic trapping" is meant that the molecule can enter the membrane domain, but it doesn't have the sufficient energy to jump through the membrane (e.g., via micellar jackets) or that a "leap" back out of the membrane (e.g., into the extracellular space) becomes thermodynamically preferred. Accordingly, as a result of interferent blocking by the silicone/hydrophilic-hydrophobic polymer blend membrane domain(s), non-constant noise is reduced, which in turn improves sensor accuracy.

In embodiments wherein the membrane system 32 is employed in an implantable glucose-measuring device, the cell impermeable domain 42 is permeable to oxygen and glucose or a substance indicative of the concentration of glucose. In embodiments wherein the membrane system is employed in a drug delivery device or other device for delivering a substance to the body, the cell impermeable domain is permeable to the drug or other substance dispensed from the device. In embodiments wherein the membrane system is employed for cell transplantation, the cell impermeable domain is semi-permeable, for example, impermeable to immune cells and soluble factors responsible for rejecting transplanted tissue, but permeable to the ingress of glucose and oxygen for the purpose of sustaining the transplanted tissue; additionally, the cell impermeable domain is permeable to the egress of the gene product of interest (for example, insulin).

In some embodiments of the silicone/hydrophilic-hydrophobic polymer blend membrane domain(s) (e.g., cell impermeable domain 42), bioactive agents are incorporated therein and/or thereon. In some embodiments, bioactive agents are incorporated to either enhance or ameliorate the biological response by the tissue surrounding the implanted sensor. In one exemplary embodiment, reactive oxygen/nitrogen species scavengers (such as but not limited to alpha-tocopherol, Super Oxide Dismutase (SOD) and the like) are incorporated into or on the cell impermeable domain to ameliorate the affect of $H_2O_2$ and other reactive species released by incoming macrophages. In another exemplary embodiment, corticosteroids are incorporated into or on the cell impermeable domain to diminish the immune response (e.g., to suppress $H_2O_2$ release by macrophages moving into the locality of the sensor after sensor implantation). In yet another exemplary embodiment, vascular permeability factors, such as but not limited to BPF, VEGF, Cytokines, IL-9 and IL-11, are incorporated into or on the cell impermeable domain to promote vasodilation of nearby capillaries, to promote the dilution of interfering species in the locality of the implanted sensor.

The silicone/hydrophilic-hydrophobic blend material used to form a cell impermeable domain having micellar jackets can be used to form any domain of the membrane system, including but not limited to the electrode domain, the interference domain, the enzyme domain, the resistance domain, and the like. In one embodiment, at least one of the membrane system domains is formed of a silicone/hydrophilic-hydrophobic blend that forms micellar jackets within the membrane domain. In another embodiment, at least two of the domains of the membrane system are formed of a silicone/hydrophilic-hydrophobic blend that forms micellar jackets within the membrane domain. In yet another embodiment, the membrane system is formed of a single domain/layer formed of a silicone/hydrophilic-hydrophobic blend that forms micellar jackets within the membrane domain. In a further embodiment, the single domain performs the functions of the electrode, interference, enzyme and/or resistance domains, for example, including an enzyme for detecting analyte.

Cell Disruptive Domain

In some embodiments, the membrane system 32 includes an optional cell disruptive domain 40 (FIGS. 4B-4C). The cell disruptive domain 40 and cell impermeable domain 42 (when they both exist) can be formed together as one unitary structure. Alternatively, the cell disruptive and cell impermeable domains 40, 42 of the membrane system can be formed as two separate layers that are mechanically or chemically bonded together. In one embodiment, the cell disruptive domain 40 and cell impermeable domain 42 consist of a unitary structure having graduated properties. For example, the porosity of the unitary structure may vary from high porosity at the tissue side of the layer to very low or no porosity at the sensor side. In addition, the chemical properties of such a graduated structure may also vary. For example, the concentration of the hydrophilic polymer may vary throughout the structure, increasing in concentration toward the sensor side of the layer. The lower concentration on the tissue side allows for increased structural integrity to support an open-celled structure while the higher concentration on the sensor side promotes increased transport of aqueous analytes through the polymer blend. In some embodiments, e.g., short-term sensors, no cell disruptive domain is needed, thus the cell impermeable domain is the most outer layer.

The cell disruptive domain 40 and the cell impermeable domain 42 (when they both exist) can be secured to each other by any suitable method as is known in the art. For example, the cell impermeable domain can simply be layered or cast upon the porous cell disruptive domain so as to form a mechanical attachment. Alternatively, chemical and/or mechanical attachment methods can be suitable for use. Chemical attachment methods can include adhesives, glues, lamination, and/or wherein a thermal bond is formed through the application of heat and pressure, and the like. Suitable adhesives are those capable of forming a bond between the materials that make up both the barrier cell disruptive domain and the cell impermeable domain, and include liquid and/or film applied adhesives. An appropriate material can be designed that can be used for preparing both domains such that the composite is prepared in one step, thereby forming a unitary structure. For example, when the cell disruptive domain and the cell impermeable domain comprise silicone, the materials can be designed so that they can be covalently cured to one another. However, in some embodiments wherein the cell impermeable domain comprises a part of the implantable device, it can be attached to or simply lie adjacent to the cell disruptive layer.

In some embodiments wherein an adhesive is employed to secure the two layers, the adhesive can comprise a biocompatible material. However, in some embodiments adhesives not generally considered to have a high degree of biocompatibility can also be employed. Adhesives with varying degrees of biocompatibility suitable for use include acrylates, for example, cyanoacrylates, epoxies, methacrylates, polyurethanes, and other polymers, resins, RTV silicone, and crosslinking agents as are known in the art. In some embodiments, a layer of woven or non-woven material (such as ePTFE) is cured to the cell disruptive domain after which the material is bonded to the cell impermeable domain, which allows a good adhesive interface between the cell disruptive and cell impermeable domains using a biomaterial known to respond well at the tissue-device interface, for example.

The membrane systems of preferred embodiments are constructed of one or more membrane layers. Each distinct layer can comprise the same or different materials. Furthermore, each layer can be homogenous or alternatively may comprise different domains or gradients where the composition varies.

In some embodiments, the sensor includes a porous material disposed over some portion thereof, which modifies the host's tissue response to the sensor (FIG. 4C). In some embodiments, the porous material surrounding the sensor advantageously enhances and extends sensor performance and lifetime in the short term by slowing or reducing cellular migration to the sensor and associated degradation that would otherwise be caused by cellular invasion if the sensor were directly exposed to the in vivo environment. Alternatively, the porous material can provide stabilization of the sensor via tissue ingrowth into the porous material in the long term. Suitable porous materials include silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, poly(ethylene oxide), poly(propylene oxide) and copolymers and blends thereof, polysulfones and block copolymers thereof including, for example, di-block, tri-block, alternating, random and graft copolymers, as well as metals, ceramics, cellulose, hydrogel polymers, poly (2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(1-lysine), poly (L-lactic acid), hydroxyethylmethacrylate, hydroxyapeptite, alumina, zirconia, carbon fiber, aluminum, calcium phosphate, titanium, titanium alloy, nintinol, stainless steel, and CoCr alloy, or the like, such as are described in U.S. Patent Publication No. US-2005-0031689 A1 and U.S. Patent Publication No. US-2005-0112169-A1.

In some embodiments, the porous material surrounding the sensor provides unique advantages in the short term (e.g. one to 14 days) that can be used to enhance and extend sensor performance and lifetime. However, such materials can also provide advantages in the long term too (e.g. greater than 14 days). Particularly, the in vivo portion of the sensor (the portion of the sensor that is implanted into the host's tissue) is encased (partially or fully) in a porous material. The porous material can be wrapped around the sensor (for example, by wrapping the porous material around the sensor or by inserting the sensor into a section of porous material sized to receive the sensor). Alternately, the porous material can be deposited on the sensor (for example, by electrospinning of a polymer directly thereon). In yet other alternative embodiments, the sensor is inserted into a selected section of porous biomaterial. Other methods for surrounding the in vivo portion of the sensor with a porous material can also be used as is appreciated by one skilled in the art.

The porous material surrounding the sensor advantageously slows or reduces cellular migration to the sensor and associated degradation that would otherwise be caused by cellular invasion if the sensor were directly exposed to the in vivo environment. Namely, the porous material provides a barrier that makes the migration of cells towards the sensor more tortuous and therefore slower (providing short term advantages). It is believed that this reduces or slows the sensitivity loss normally observed in a short-term sensor over time.

The cell disruptive domain 40 is preferably formed from high oxygen soluble materials such as polymers formed from silicone, fluorocarbons, perfluorocarbons, or the like. In one embodiment, the cell disruptive domain is formed from a silicone composition with a non-silicon containing hydrophile such as such as polyethylene glycol, propylene glycol, pyrrolidone, esters, amides, carbonates, or polypropylene glycol covalently incorporated or grafted therein. In some alternative embodiments, the cell disruptive domain is formed from polyethylene-co-tetrafluoroethylene, polyolefin, polyester, polycarbonate, biostable polytetrafluoroethylene, homopolymers, copolymers, terpolymers of polytetrafluoroethylene, polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones or block copolymers thereof including, for example, di-block, tri-block, alternating, random and graft copolymers.

In an embodiment wherein the porous material is a high oxygen solubility material, such as porous silicone, the high oxygen solubility porous material surrounds some of or the entire in vivo portion of the sensor. In some embodiments, a lower ratio of oxygen-to-glucose can be sufficient to provide excess oxygen by using a high oxygen soluble domain (for example, a silicone- or fluorocarbon-based material) to enhance the supply/transport of oxygen to the enzyme membrane and/or electroactive surfaces. It is believed that some signal noise normally seen by a conventional sensor can be attributed to an oxygen deficit. Silicone has high oxygen permeability, thus promoting oxygen transport to the enzyme domain. By enhancing the oxygen supply through the use of a silicone composition, for example, glucose concentration can be less of a limiting factor. In other words, if more oxygen is supplied to the enzyme and/or electroactive surfaces, then more glucose can also be supplied to the enzyme without creating an oxygen rate-limiting excess. While not being bound by any particular theory, it is believed that silicone materials provide enhanced bio-stability when compared to other polymeric materials such as polyurethane.

In certain aspects, modifying a small structured sensor with a biointerface structure, material, matrix, and/or membrane that creates a space appropriate for filling with fluid in vivo can enhance sensor performance. In some embodiments, the small structured sensor includes a porous biointerface material, which allows fluid from the surrounding tissues to form a fluid-filled pocket around at least a portion of the sensor. It is believed that the fluid-filled pocket provides a sufficient source of analyte-containing fluid for accurate sensor measurement in the short term. Additionally or alternatively, inclusion of bioactive agents can modify the host's tissue response, for example to reduce or eliminate tissue ingrowth or other cellular responses into the biointerface.

In some aspects, modifying a small structured sensor with a structure, material, and/or membrane/matrix that allows tissue ingrowth without barrier cell formation can enhance sensor performance. For example, a vascularized bed of tissue for long-term analyte sensor measurement. In some embodiments, a porous biointerface membrane, including a plurality of interconnected cavities and a solid portion, covering at least the sensing portion of a small structured sensor allows vascularized tissue ingrowth therein. Vascularized tissue ingrowth provides a sufficient source of analyte-containing tissue in the long term. Additionally or alternatively, inclusion of bioactive agents can modify the host's tissue response, for example to reduce or eliminate barrier cell layer formation within the membrane.

When used herein, the terms "membrane" and "matrix" are meant to be interchangeable. In these embodiments a cell disruptive domain 40 is provided that includes an architecture, including cavity size, configuration, and/or overall thickness, that modifies the host's tissue response, for example, by creating a fluid pocket, encouraging vascularized tissue ingrowth, disrupting downward tissue contracture, resisting fibrous tissue growth adjacent to the device, and/or discouraging barrier cell formation (FIG. 4C). The biointerface preferably covers at least the sensing mechanism of the sensor and can be of any shape or size, including uniform, asymmetrically, or axi-symmetrically covering or surrounding a sensing mechanism or sensor.

In some embodiments, the cell disruptive domain 40 of the biointerface membrane (also referred to as the cell disruptive domain) includes an architecture that supports tissue ingrowth, disrupts contractile forces typically found in a foreign body response, encourages vascularity within the membrane, and disrupts the formation of a barrier cell layer. In some alternative embodiments, the cell disruptive domain of the biointerface membrane includes an architecture that creates a fluid-filled space surrounding an implanted device, which allows the passage of the analyte, but protects sensitive portions of the device from substantial fibrous tissue ingrowth and associated forces.

In general, the cell disruptive domain 40, also referred to as the cell disruptive domain, comprises an open-celled configuration comprising interconnected cavities and solid portions. The distribution of the solid portion and cavities of the cell disruptive domain preferably includes a substantially co-continuous solid domain and includes more than one cavity in three dimensions substantially throughout the entirety of the cell disruptive layer. However, some short-term embodiments may not require co-continuity of the cavities. Generally, cells can enter into the cavities; however, they cannot travel through or wholly exist within the solid portions. The cavities permit most substances to pass through, including, for example, cells and molecules. One example of a suitable material is expanded polytetrafluoroethylene (ePTFE). U.S. Pat. No. 6,702,857 and U.S. Patent Publication No. US-2005-0112169-A1 describe membranes having a cell disruptive domain and are both incorporated herein by reference in their entirety.

The cell disruptive domain 40 can be defined using alternative methods. In an alternative preferred embodiment, fibrous non-woven or woven materials, or other such materials, such as electrospun, felted, velvet, scattered, or aggregate materials, are manufactured by forming the solid portions without particularly defining the cavities therebetween. Accordingly, in these alternative embodiments, structural elements that provide the three-dimensional conformation can include fibers, strands, globules, cones, and/or rods of amorphous or uniform geometry. These elements are hereinafter referred to as "strands." The solid portion of the cell disruptive domain can include a plurality of strands, which generally define apertures formed by a frame of the interconnected strands. The apertures of the material form a framework of interconnected cavities. Formed in this manner, the cell disruptive domain is defined by a cavity size of about 0.6 to about 1 mm in at least one dimension.

Referring to the dimensions and architecture of the cell disruptive domain 40, the porous biointerface membranes can be loosely categorized into at least two groups: those having a micro-architecture and those having a macro-architecture.

In general, the cavity size of a macro-architecture provides a configuration and overall thickness that encourages vascular tissue ingrowth and disrupts tissue contracture that is believed to cause barrier cell formation in the long term in vivo, while providing a long-term, robust structure. Referring to the macro-architecture, a substantial number of the cavities, defined using any of the methods described above, are greater than or equal to about 20 μm in one dimension. In some other embodiments, a substantial number of the cavities are greater than or equal to about 30, 40, 50, 60, 70, 80, 90, 100, 120, 180, 160, 180, 200, 280, 280, 320, 360, 400, 500, 600, 700 μm, and preferably less than about 1 mm in one dimension.

The biointerface membrane can also be formed with a micro-architecture as defined herein. Generally, at least some of the cavities of a micro-architecture have a sufficient size and structure to allow inflammatory cells to partially or completely enter into the cavities. However, in contrast to the macro-architecture, the micro-architecture does not allow extensive ingrowth of vascular and connective tissues within the cavities. Therefore, in some embodiments, the micro-architecture of preferred embodiments is defined by the actual size of the cavity, wherein the cavities are formed from a mold, for example, such as described in more detail above. However, in the context of the micro-architecture it is preferable that the majority of the mold dimensions, whether particles, beads, crystals, coral, self-assembly beads, etched or broken silicon pieces, glass frit pieces, or other mold elements that form cavities, are less than about 20 μm in at least one dimension.

In some alternative embodiments, wherein the biointerface membrane is formed from a substantially fibrous material, the micro-architecture is defined by a strand size of less than about 6 μm in all but the longest dimension, and a sufficient number of cavities are provided of a size and structure to allow inflammatory cells, for example, macrophages, to completely enter through the apertures that define the cavities, without extensive ingrowth of vascular and connective tissues.

In certain embodiments, the micro-architecture is characterized, or defined, by standard pore size tests, such as the bubble point test. The micro-architecture is selected with a nominal pore size of from about 0.6 μm to about 20 μm. In some embodiments, the nominal pore size is from about 1, 2, 3, 4, 5, 6, 7, 8, or 9 μm to about 10, 11, 12, 13, 14, 15, 16, 17, 18, or 19 μm. It has been found that a porous polymer membrane having an average nominal pore size of from about 0.6 μm to about 20 μm functions satisfactorily in creating a vascular bed within the micro-architecture at the device-tissue interface. The term "nominal pore size" in the context of the micro-architecture in certain embodiments is derived from methods of analysis common to membrane, such as the ability of the membrane to filter particles of a particular size, or the resistance of the membrane to the flow of fluids. Because of the amorphous, random, and irregular nature of most of these commercially available membranes, the "nominal pore size" designation may not actually indicate the size or shape of the apertures and cavities, which in reality have a high degree of variability. Accordingly, as used herein with reference to the micro-architecture, the term "nominal pore size" is a manufacturer's convention used to identify a particular membrane of a particular commercial source which has a certain bubble point; as used herein, the term "pore" does not describe the size of the cavities of the material in some embodiments. The bubble point measurement is described in Pharmaceutical Technology, May 1983, pp. 76 to 82.

The optimum dimensions, architecture (for example, micro-architecture or macro-architecture), and overall structural integrity of the membrane can be adjusted according to the parameters of the device that it supports. For example, if the membrane is employed with a glucose-measuring device, the mechanical requirements of the membrane can be greater for devices having greater overall weight and surface area when compared to those that are relatively smaller.

The thickness of the optional cell disruptive domain 40 is typically from about 10 μm or less to about 3000 μm or more, preferably from about 20, 30, 40, 50, 60, 70, 80, 90, or 100 μm to about 800, 900, 1000, 1100, 1200, 1300, 1400, 1500, 1600, 1700, 1800, 1900, 2000, or 2500 μm, and most preferably from about 150, 200, 250, 300, 350, or 400 μm to about 450, 500, 550, 600, 650, 700, or 750 μm. In some embodiments, the thickness of the cell disruptive domain is from about 100, 150, 200 or 250 microns to about 1000, 1100, 1200, 1300, or 1400 microns. In other embodiments, the thickness of the cell disruptive domain is from about 300, 350, 400, 450, 500, or 550 microns to about 500, 550, 600, 650, 700, 750, 800, 850, or 900 microns. However, in some alternative embodiments a thinner or thicker cell disruptive domain can be desired.

The solid portion preferably includes one or more materials such as silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, polysulfones and block copolymers thereof including, for example, di-block, tri-block, alternating, random and graft copolymers. In some embodiments, the material selected for the cell disruptive domain is an elastomeric material, for example, silicone, which is able to absorb stresses that can occur in vivo such that sheer and other environmental forces are significantly minimized at the cell disruptive domain. The solid portion can comprises a silicone composition with a hydrophile such as Polyethylene Glycol (PEG) covalently incorporated or grafted therein, such as described in U.S. Patent Publication No. US-2005-0090607-A1, which is incorporated herein by reference in its entirety.

One preferred material that can be used to form the solid portion of the biointerface matrix is a material that allows the passage of the analyte (e.g., glucose) there through. For example, the biointerface matrix may be formed from a silicone polymer/hydrophobic-hydrophilic polymer blend. In one embodiment, The hydrophobic-hydrophilic polymer for use in the blend may be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. No. 4,803,243 and U.S. Pat. No. 4,686,044, which are incorporated herein by reference). In one embodiment, the hydrophobic-hydrophilic polymer is a copolymer of poly(ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. In one embodiment, PLURONIC® F-127 is used. Other PLURONIC® polymers include PPO-PEO-PPO triblock copolymers (e.g., PLURONIC® R products). Other suitable commercial polymers include, but are not limited to, SYNPERONICS® products available from UNIQEMA®.

The cell disruptive domain 40 is preferably formed from high oxygen soluble materials such as polymers formed from silicone, fluorocarbons, perfluorocarbons, or the like. In these embodiments, transport of water-soluble agents such as an aqueous analyte occurs primarily through the pores and cavities of the layer. In some embodiments, the cell disruptive domain is formed from polyethylene-co-tetrafluoroethylene, polyolefin, polyester, polycarbonate, biostable polytetrafluoroethylene, homopolymers, copolymers, terpolymers of polytetrafluoroethylene, polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones or block copolymers thereof including, for example, di-block, tri-block, alternating, random and graft copolymers. In other embodiments, the cell disruptive domain is formed from a silicone composition with a non-silicon containing hydrophile such as such as polyethylene glycol, propylene glycol, pyrrolidone, esters, amides, or carbonates covalently incorporated or grafted therein such that water-soluble agents can also be transported through polymeric matrix of the cell disruptive domain 40. Such compositions are described for example in U.S. Patent Publication No. US-2005-0090607-A1 and U.S. Patent Publication No. US-2005-0090607-A1, which is incorporated herein by reference in its entirety. In still other embodiments, the cell disruptive domain is formed from a monomer, polymer, copolymer, or blend including one or more of: lactic acid, glycolic acid, anhydrides, phosphazenes, vinyl alcohol, ethylene vinyl alcohol, acetates, ε-caprolactone, β-hydroxybutyrate, γ-ethyl glutamate, DTH iminocarbonate, Bisphenol A iminocarbonate, sebacic acid, hexadecanoic acid, saccharides, chitosan, hydroxyethyl methacrylate (HEMA), ceramics, hyaluronic acid (HA), collagen, gelatin, starches, hydroxy apatite, calcium phosphates, bioglasses, amino acid sequences, proteins, glycoproteins, protein fragments, agarose, fibrin, n-butylene, isobutylene, dioxanone, nylons, vinyl chlorides, amides, ethylenes, n-butyl methacrylate (BMA), metal matrix composites (MMCs), metal oxides (e.g. aluminum), DETOSU-1,6 HD-t-CDM ortho ester, styrene, and plasma treated surfaces of any of the above.

In some embodiments, the cell disruptive domain 40 is formed from silicone polymer/hydrophilic polymer blends such as described above. Due to the open-cell configuration of the cell disruptive domain 40, the ratio of silicone polymer to hydrophilic polymer may be chosen to increase the structural integrity of the layer so that the open-cell configuration is maintained. Alternatively, the structural integrity of the cell disruptive domain can be increased by choosing a silicone polymer having properties suitable for increasing structural integrity (e.g., a silicone polymer having an increased durometer). In one embodiment, the concentration of hydrophilic polymer (e.g., PLURONIC® F-127) relative to silicone polymer (e.g., MED-4840) is from about 1% to about 30%, preferably from about 5% to about 20% in the cell disruptive domain 40.

Additionally, elastomeric materials with a memory of the original configuration can withstand greater stresses without affecting the configuration, and thus the function, of the device.

In some embodiments, the cell disruptive domain 40 can include a macro-architecture and a micro-architecture located within at least a portion of the macro-architecture, such as is described in co-pending U.S. Patent Publication No. US-2005-0251083-A1. For example, the macro-architecture includes a porous structure with interconnected cavities such as described with reference to the solid portion of the first domain, wherein at least some portion of the cavities of the cell disruptive domain are filled with the micro-architecture that includes a fibrous or other fine structured material that aids in preventing formation of a barrier cell layer, for example in pockets in the bottom of the cavities of the macro-architecture adjacent to the implantable device.

In certain embodiments, other non-resorbable implant materials can be used in forming the cell disruptive domain 40, including but not limited to, metals, ceramics, cellulose, hydrogel polymers, poly (2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(1-lysine), poly (L-lactic acid), hydroxyethylmethacrylate, hydroxyapeptite, alumina, zirconia, carbon fiber, aluminum, calcium phosphate (and its chemical variants), titanium, titanium alloy, nintinol, stainless steel, and CoCr alloy.

Due to the small dimension(s) of the sensor (sensing mechanism) of some embodiments, some conventional methods of porous membrane formation and/or porous membrane adhesion are inappropriate for the formation of the biointerface membrane onto the sensor as described herein. Accordingly, the following embodiments exemplify systems and methods for forming and/or adhering a biointerface membrane onto a small structured sensor as defined herein. For example, the biointerface membrane of some embodiments can be formed onto the sensor using techniques such as electrospinning, molding, weaving, direct-writing, lyophilizing, wrapping, and the like. Additional methods of forming a membrane system on a small-structured sensor can be found in U.S. Patent Publication No. US-2006-0270923-A1, which is incorporated herein by reference. In some embodiments, a cell impermeable domain 42 can additionally be formed using known thin film techniques, such as dip coating, spray coating, spin coating, tampo printing, and the like.

With regards to the devices of the preferred embodiments, the cell disruptive domain 40 is optional and can be omitted when using an implantable device that does not prefer tissue ingrowth, for example, a short-lived device (for example, less than one day to about a week or up to about one month) or one that delivers tissue response modifiers.

Oxygen Solubility

In some embodiments, the membrane systems 32 for use in implantable sensors are formed as a physically continuous membrane, namely, a monolithic membrane having substantially uniform physical structural characteristics from one side of the membrane to the other.

Some layers of the membrane systems 32 of some embodiments include materials with high oxygen solubility. In some embodiments, one or more of the above-described domains are formed from high oxygen solubility material. In some embodiments, the high oxygen soluble material includes silicones, fluorocarbons, perfluorocarbons, or the like. In one embodiment, one or more domains is/are formed from a silicone composition that allows the transport of glucose or other such water-soluble molecules (for example, drugs), such as are described in more detail with reference to U.S. Patent Publication No. US-2005-0090607-A1, the contents of which is hereby incorporated by reference in its entirety. In some embodiments, the membrane systems with high oxygen solubility simultaneously permit efficient transport of aqueous solutions of the analyte.

The phrases "high oxygen solubility" and "high oxygen soluble" as used herein are broad phrases and are used in their ordinary sense, including, without limitation, a domain or material property that includes higher oxygen solubility than aqueous media so that it concentrates oxygen from the biological fluid surrounding the membrane system. In some preferred embodiments, a high oxygen solubility polymer has at least about 2× higher oxygen solubility than aqueous media, more preferably at least about 3×, 4×, 5×, or 6× higher oxygen solubility than aqueous media, and most preferably at least about 7×, 8×, 9×, 10× or more higher oxygen solubility than aqueous media. In one embodiment, high oxygen solubility is defined as having higher oxygen solubility than at least one of a hydrocarbonaceous polymer and an oxyhydrocarbon polymer (a hydrocarbonaceous polymer is a polymeric material consisting of carbon and hydrogen atoms and an oxyhydrocarbonaceous polymer is a polymeric material consisting of carbon, hydrogen, and oxygen atoms). Oxygen solubility can be measured using any known technique, for example by removing the oxygen from the polymer (namely, solution) via at least three Freeze-Pump-Thaw cycles and then measuring the resultant oxygen (for example, using a manometer).

Oxygen permeability (Dk) is calculated as diffusion multiplied by solubility. Oxygen Permeability is conveniently reported in units of Barrers (1 Barrer=$10^{-10}$ cm$^3$ O$_2$ (STP) cm/cm$^2$ s cmHg). Insulating materials of preferred embodiments that have a high oxygen permeability typically have an oxygen permeability of from about 1 Barrer or less to about 1000 Barrers or more, preferably from about 1, 2, 3, 4, 5, 6, 7, 8, 9, 10, 15, 20, 25, 30, 35, 40, 45, 50, 55, 60, 65, 70, 75, 80, 85, 90, 95, or 100 Barrers to about 125, 150, 175, 200, 225, 250, 275, 300, 325, 350, 375, 400, 425, 450, 475, 500, 550, 600, 650, 700, 750, 800, 850, 900, or 950 Barrers. In one exemplary embodiment, the properties of silicone (and/or silicone compositions) inherently enable materials formed from silicone to act as a high oxygen solubility domain.

Silicone/Hydrophilic Polymer Blend Materials

As described elsewhere herein, one or more membrane domains and/or layer(s) can be formed from a composition that, in addition to providing high oxygen solubility, allows for the transport of the analyte (e.g., glucose or other such water-soluble molecules, such as drugs). In one embodiment, these layers comprise a blend of a silicone polymer with a hydrophilic polymer. By "hydrophilic polymer," it is meant that the polymer has an affinity for water, due to the presence of one or more hydrophilic substituents, and generally is primarily soluble in water or has a tendency to absorb water. In one example, the hydrophilic component of a hydrophilic polymer promotes the movement of water and/or compounds in the water (e.g., by diffusion or other means) through a membrane formed of the hydrophilic polymer, such as by lowering the thermodynamic barrier to movement of compounds in the water into the membrane.

In some embodiments, hydrophilic polymers include hydrophilic-hydrophobic polymers. Generally, the terms "hydrophilic-hydrophobic" and "hydrophobic-hydrophilic" are used interchangeably herein (are not meant to imply that either the hydrophilic or the hydrophobic substituents are the major component of the polymer) and refer to the property of having both hydrophilic and hydrophobic substituents and/or characteristics in a single molecule, such as, for example, a polymer.

The hydrophilic and hydrophobic substituents of a polymer can affect the polymer's behavior in certain circumstances, such as but not limited to silicone/hydrophilic-hydrophobic blend materials and micellar jackets, which are discussed elsewhere herein. Using PEO-PPO-PEO as an exemplary polymer, the polymer's major component (PEO) is hydrophilic and can provide an overall hydrophilic character to the molecule (e.g., the molecule generally behaves in a hydrophilic manner). However, the hydrophobic component (PPO) of the polymer makes it possible for the polymer to have some hydrophobic character (e.g., for portions of the molecule to behave in the manner of a hydrophobic molecule), in some situations. In some circumstances, such as formation of micellar jackets in a silicone/hydrophilic-hydrophobic blend material, the polymer self-organizes, relative to the silicone (e.g., silicone globule(s)) such that the hydrophobic PPO is adjacent to the silicone (which is hydrophobic) and the two PEO groups project away from the silicone (e.g., due to thermodynamic forces). Depending upon the circumstance (e.g., the polymer selected), variations of the micellar jacket structure described above (e.g., opposite orientations) are possible. For example, it is believed that in a mixture of PPO-PEO-PPO and silicone, the PPO groups self-orient toward the silicone and the PEO center is oriented away from the silicone.

In one embodiment, the hydrophilic polymer has a molecular weight of at least about 1000 g/mol, 5,000 g/mol, 8,000 g/mol, 10,000 g/mol, or 15,000 g/mol. In one embodiment, the hydrophilic polymer comprises both a hydrophilic domain and a partially hydrophobic domain (e.g., a copolymer, also referred to herein as a hydrophobic-hydrophilic polymer). The hydrophobic domain(s) facilitate the blending of the hydrophilic polymer with the hydrophobic silicone polymer, such as but not limited to formation of micellar jackets within and/or around the silicone. In one embodiment, the hydrophobic domain is itself a polymer (i.e., a polymeric hydrophobic domain). For example, in one embodiment, the hydrophobic domain is not a simple molecular head group but is rather polymeric. In various embodiments, the molecular weight of any covalently continuous hydrophobic domain within the hydrophilic polymer is at least about 500 g/mol, 700 g/mol, 1000 g/mol, 2000 g/mol, 5000 g/mol, or 8,000 g/mol. In various embodiments, the molecular weight of any covalently continuous hydrophilic domain within the hydrophilic polymer is at least about 500 g/mol, 700 g/mol, 1000 g/mol, 2000 g/mol, 5000 g/mol, or 8,000 g/mol.

In some embodiments, within a particular layer, the ratio of the silicone polymer to hydrophilic polymer is selected to provide an amount of oxygen and water-soluble molecule solubility such that oxygen and water-soluble molecule transport through a domain is optimized according to the desired function of that particular layer. Furthermore, in some embodiments, the ratio of silicone polymer to hydrophilic polymer, as well as the polymeric compositions, are selected such that a layer constructed from the material has interference characteristics that inhibit transport of one or more interfering species through the layer. Some known interfering species for a glucose sensor include, but are not limited to, acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid. Accordingly, in some embodiments, a silicone polymer/hydrophilic polymer layer as disclosed herein is less permeable to one or more of these interfering species than to the analyte, e.g., glucose.

In some embodiments, silicone polymer/hydrophilic polymer blends are used in multiple layers of a membrane. In some of these embodiments, the ratio of silicone polymer to hydrophilic polymer (in the layers incorporating the blends) varies according to the desired functionality of each layer. The relative amounts of silicone polymer and hydrophilic polymer described below are based on the respective amounts found in the cured polymeric blend. Upon introduction into an aqueous environment, some of the polymeric components may leach out, thereby changing the relative amounts of silicone polymer and hydrophilic polymer. For example, substantial amounts of the portions of the hydrophilic polymer that are not cross-linked may leach out, for example, depending on the hydrophilic polymer's molecular weight and how tortuous it the diffusion path out of the membrane.

In some embodiments, the silicone and hydrophilic polymers form a substantial blend. Namely, the amount of any cross-linking between the silicone polymer and the hydrophilic polymer is substantially limited. In various embodiments, at least about 75%, 85%, 95%, or 99% of the silicone polymer is not covalently linked to the hydrophilic polymer. In some embodiments, the silicone polymer and the hydrophilic polymer do not cross-link at all unless a cross-linking agent is used (e.g., such as described below). Similarly, in some embodiments, the amount of any entanglement (e.g., blending on a molecular level) between the silicone polymer and the hydrophilic polymer is substantially limited. In one embodiment, the silicone polymer and hydrophilic polymers form microdomains. For example, in one embodiment, the silicone polymer forms micellar jacket structures surrounded by a network of hydrophilic polymer.

The silicone polymer for use in the silicone/hydrophilic polymer blend may be any suitable silicone polymer. In some embodiments, the silicone polymer is a liquid silicone rubber that may be vulcanized using a metal- (e.g., platinum), peroxide-, heat-, ultraviolet-, or other radiation-catalyzed process. In some embodiments, the silicone polymer is a dimethyl- and methylhydrogen-siloxane copolymer. In some embodiments, the copolymer has vinyl substituents. In some embodiments, commercially available silicone polymers may be used. For example, commercially available silicone polymer precursor compositions may be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydrogen-siloxane copolymers, amorphous silica, a platinum catalyst, a crosslinker, and an inhibitor. The two components may be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation.

The hydrophilic polymer for use in the blend may be any suitable hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044, which are incorporated herein by reference). In one embodiment, the hydrophilic polymer is a copolymer of poly(ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. Some PLURONIC® polymers are triblock copolymers of poly(ethylene oxide)-poly(propylene oxide)-poly(ethylene oxide) having the general molecular structure:

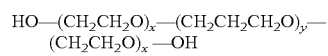

where the repeat units x and y vary between various PLURONIC® products. The poly(ethylene oxide) blocks act as a hydrophilic domain allowing the dissolution of aqueous agents in the polymer. The poly(propylene oxide) block acts as a hydrophobic domain facilitating the blending of the PLURONIC® polymer with a silicone polymer. In one embodiment, PLURONIC® F-127 is used having x of approximately 100 and y of approximately 65. The molecular weight of PLURONIC® F-127 is approximately 12,600 g/mol as reported by the manufacture. Other PLURONIC® polymers include PPO-PEO-PPO triblock copolymers (e.g., PLURONIC® R products). Other suitable commercial polymers include, but are not limited to, SYNPERONICS® products available from UNIQEMA®.

The polyether structure of PLURONIC® polymers is relatively inert. Accordingly, without being bound by any particular theory, it is believed that the PLURONIC® polymers do not substantially react with the components in MED-4840 or other silicone polymer precursors.

Those of skill in the art will appreciate that other copolymers having hydrophilic and hydrophobic domains may be used. For example, in one alternative embodiment, a triblock copolymer having the structure hydrophobic-hydrophilic-hydrophobic may be used. In another alternative embodiment, a diblock copolymer having the structure hydrophilic-hydrophobic is used. Additional devices, methods and compositions can be found in U.S. Patent Publication No. US-2006-0270923-A1, and U.S. patent application Ser. No. 11/404,417, filed on Apr. 14, 2006, and entitled "SILICONE BASED MEMBRANES FOR USE IN IMPLANTABLE GLUCOSE SENSORS," both of which are incorporated herein by reference.

Layers that include a silicone polymer-hydrophilic polymer blend can be made using any of the methods of forming polymer blends known in the art. In one embodiment, a silicone polymer precursor (e.g., MED-4840) is mixed with a solution of a hydrophilic polymer (e.g., PLURONIC® F-127 dissolved in a suitable solvent such as acetone, ethyl alcohol, or 2-butanone). The mixture may then be drawn into a film or applied in a multi-layer membrane structure using any method known in the art (e.g., spraying, painting, dip coating, vapor depositing, molding, 3-D printing, lithographic techniques (e.g., photolithograph), micro- and nano-pipetting printing techniques, etc.). The mixture may then be cured under high temperature (e.g., 50-150° C.). Other suitable curing methods include ultraviolet or gamma radiation, for example. During curing, the silicone polymer precursor will vulcanize and the solvent will evaporate. In one embodiment, after the mixture is drawn into a film, another preformed layer of the membrane system is placed on the film. Curing of the film then provides bonding between the film and the other preformed layer. In one embodiment, the preformed layer is the cell disruptive layer. In one embodiment, the cell disruptive domain comprises a preformed porous silicone membrane. In other embodiments, the cell disruptive domain is also formed from a silicone polymer/hydrophilic polymer blend. In some embodiments, multiple films are applied on top of the preformed layer. Each film may posses a finite interface with adjacent films or may together form a physically continuous structure having a gradient in chemical composition.

Some amount of cross-linking agent may also be included in the mixture to induce cross-linking between hydrophilic polymer molecules. For example, when using a PLURONIC® polymer, a cross-linking system that reacts with pendant or terminal hydroxy groups or methylene, ethylene, or propylene hydrogen atoms may be used to induce cross linking. Non-limiting examples of suitable cross-linking agents include ethylene glycol diglycidyl ether (EGDE), poly(ethylene glycol) diglycidyl ether (PEGDE), or dicumyl peroxide (DCP). While not being bound by any particular theory, at low concentrations, these cross-linking agents are believed to react primarily with the PLURONIC® polymer with some amount possibly inducing cross-linking in the silicone polymer or between the PLURONIC® polymer and the silicone polymer. In one embodiment, enough cross-linking agent is added such that the ratio of cross-linking agent molecules to hydrophilic polymer molecules added when synthesizing the blend is about 10 to about 30 (e.g., about 15 to about 20). In one embodiment, from about 0.5% to about 15% w/w of cross-linking agent is added relative to the total dry weights of cross-linking agent, silicone polymer, and hydrophilic polymer added when blending the ingredients (in one example, from about 1% to about 10%). In one embodiment, from about 5% to about 30% of the dry ingredient weight is the PLURONIC® polymer. During the curing process, substantially all of the cross-linking agent is believed to react, leaving substantially no detectable unreacted cross-linking agent in the final film.

In some embodiments, other agents may be added to the mixture to facilitate formation of the blend. For example, a small amount of butylhydroxy toluene (BHT) (e.g., about 0.01% w/w) or other suitable antioxidant may be mixed with a PLURONIC® to stabilize it.

In some alternative embodiments, precursors of both the silicone polymer and hydrophilic polymer may be mixed prior to curing such that polymerization of both the silicone polymer and the hydrophilic polymer occur during curing. In another embodiment, already polymerized silicone polymer is mixed with a hydrophilic polymer such that no significant polymerization occurs during curing.

While not wishing to be bound by theory, it is believed that a micelle-like structure, referred to herein as a micellar jacket structure, can be formed by combining certain hydrophobic polymers (e.g., silicone) with certain amphipathic polymers (e.g., hydrophilic polymers such as PLURONIC® polymers), which, when substantially blended, create a mechanism by which glucose and other analytes are transported at a limited rate. One example of a limited rate is diffusion of oxygen and glucose into the membrane at a ratio of 50:1 (50 oxygen molecules for every one glucose molecule). In a preferred embodiment, oxygen and glucose diffuse into the membrane at the limited rate of 100:1. In a more preferred embodiment, oxygen and glucose diffuse into the membrane at the limited rate of 200:1.

In a first mechanism of limited analyte transport, it is believed that the PLURONIC® hydrophilic and hydrophobic constituents can promote self-organization of the PLURONIC® molecules, in conjunction with the silicone, into micellar jackets. The micellar jackets provide a contiguous channel (e.g., a tortuous path) though the silicone, through which the analyte travels. For example, at a first side of a membrane/domain, glucose dissolves into the hydrophilic component of the micellar jackets (e.g., within the membrane/domain) and diffuses through the hydrophilic portion of adjacent micellar jackets, to reach the opposite side of the membrane/domain.

In a second mechanism of limited analyte transport, it is believed that micellar jackets can provide a hydrophilic phase within the silicone membrane/domain structure. There is an energetic barrier to diffusion of the analyte (e.g., glucose) into the silicone. However, an energetic, thermodynamic force (e.g., an analyte concentration gradient) drives the analyte to pass across/through the membrane by "jumping" from one micellar jacket to another. For example, a glucose concentration gradient can provide the energy for a glucose molecule to pass into the membrane domain or layer (e.g., the cell impermeable domain formed of a substantial blend of silicone and PLURONIC®), to the first micellar jacket, then to "jump" to the next micellar jacket, and so on, until the molecule reaches the opposite side of the membrane domain/layer.

In one exemplary embodiment, a silicone-hydrophilic polymer (e.g., wherein the hydrophilic polymer is an amphipathic polymer, such as but not limited to PLURONIC®) blend is believed to promote the macromolecular self-organization of micellar jackets that clothe colloidal silicone globules (e.g., silicone granules that form a three-dimensional contiguous macromolecular structure having silicone-to-silicone contacts between the silicone granules, coated with the hydrophilic polymer), within the membrane domain. The hydrophilic groups of the micellar jackets orient toward the silicone, with the hydrophobic portions of the polymer oriented away from the silicone core of the structure. For example, in the case of silicone globules clothed with PLURONIC® (PEO-PPO-PEO), it is believed that it is thermodynamically favorable for a PLURONIC® molecule to orient itself such that the PPO "lies against" the silicone and the PEO to bends away from the silicone, for example, in a U-like shape. Inverse micellar jackets are also possible, for example, inverted micellar jackets (e.g., with the hydrophobic PPO facing outward toward the silicone and the hydrophilic PEO facing inward) within the silicone. Additionally, the micellar jackets may not be in direct, physical contact with each other, which would provide a thermodynamic barrier to molecules entering the membrane layer and traveling through/across the layer by energetically "jumping" from one micellar jacket to the next.

A variety of polymers known in the art can be used in formation of micellar jackets, such as those already discussed herein, especially those polymers discussed elsewhere herein. For additional description of useful polymers and methods of use, see the above sections entitled "Cell Impermeable Domain," and "Cell Impermeable Domain and Noise Reduction," as well as the "Examples" section, below.

In addition to facilitating analyte passage through the membrane domain, the inventors have found that the micellar jacket structure blocks diffusion of small, reactive oxygen and nitrogen interferents (e.g., $H_2O_2$, oxygen radicals, peroxynitrates, etc.) that can cause non-constant noise. While not wishing to be bound by theory, it is believed that the micellar jacket structure sufficiently slows the diffusion of the reactive oxygen and nitrogen interferents such that these molecules self-annihilate before reaching the electroactive surface(s). In contrast, it is believed that large molecular weight interferents (e.g., acetaminophen and ascorbate) are sterically and/or thermodynamically blocked and/or trapped by the micellar jackets, and thus do not reach the electroactive surface(s). Accordingly, non-constant noise produced by both small and large molecular weight interferents is attenuated, with improved sensor function as a result.

Bioactive Agents

In some alternative embodiment, the biointerface membranes (e.g., cell impermeable domain and/or cell disruptive layer) include a bioactive agent, which is incorporated into at least one of the bioprotective or cell disruptive layers 42, 40 of the biointerface membrane, or which is incorporated into the device (e.g., sensing membrane 32) and adapted to diffuse through the bioprotective and/or cell disruptive layers, in order to modify the tissue response of the host to the membrane. The architectures of the bioprotective and cell disruptive layers have been shown to create a fluid pocket, support vascularized tissue ingrowth, to interfere with and resist barrier cell layer formation, and to facilitate the transport of analytes across the membrane. However, the bioactive agent can further enhance formation of a fluid pocket, alter or enhance vascularized tissue ingrowth, resistance to barrier cell layer formation, and thereby facilitate the passage of analytes across the device-tissue interface.

In embodiments wherein the biointerface includes a bioactive agent, the bioactive agent is incorporated into at least one of the bioprotective and/or cell disruptive layers of the biointerface membrane, or into the device (e.g., including any of the membrane layers/domains) and adapted to diffuse through the bioprotective and/or cell disruptive layers, in order to modify the tissue response of the host to the membrane. In general, the architectures of the bioprotective and cell disruptive layers support vascularized tissue growth in or around the biointerface membrane, interfere with and resist barrier cell layer formation, and/or allow the transport of analytes across the membrane. However, certain outside influences, for example, faulty surgical techniques, acute or chronic movement of the implant, or other surgery-, host-, and/or implantation site-related conditions, can create acute and/or chronic inflammation at the implant site. When this occurs, the biointerface membrane architecture alone may not be sufficient to overcome the acute and/or chronic inflammation. Alternatively, the membrane architecture can benefit from additional mechanisms that aid in reducing this acute and/or chronic inflammation that can produce a barrier cell layer and/or a fibrotic capsule surrounding the implant, resulting in compromised solute transport through the membrane.

In general, the inflammatory response to biomaterial implants can be divided into two phases. The first phase consists of mobilization of mast cells and then infiltration of predominantly polymorphonuclear (PMN) cells. This phase is termed the acute inflammatory phase. Over the course of days to weeks, chronic cell types that comprise the second phase of inflammation replace the PMNs. Macrophage and lymphocyte cells predominate during this phase. While not wishing to be bound by any particular theory, it is believed that short-term stimulation of vascularization, or short-term inhibition of scar formation or barrier cell layer formation, provides protection from scar tissue formation, thereby providing a stable platform for sustained maintenance of the altered foreign body response, for example.

Accordingly, bioactive intervention can modify the foreign body response in the early weeks of foreign body capsule formation and alter the short-term and/or long-term behavior of the foreign body response. Additionally, it is believed that in some circumstances the biointerface membranes of some embodiments can benefit from bioactive intervention to overcome sensitivity of the membrane to implant procedure, motion of the implant, or other factors, which are known to otherwise cause inflammation, scar formation, and hinder device function in vivo.

In general, bioactive agents that are believed to modify tissue response include anti-inflammatory agents, anti-infective agents, anesthetics, inflammatory agents, growth factors, angiogenic (growth) factors, adjuvants, immunosuppressive agents, antiplatelet agents, anticoagulants, ACE inhibitors, cytotoxic agents, anti-barrier cell compounds, vascularization compounds, anti-sense molecules, and the like. In some embodiments, preferred bioactive agents include S1P (Sphingosine-1-phosphate), Monobutyrin, Cyclosporin A, Anti-thrombospondin-2, Rapamycin (and its derivatives), and Dexamethasone. However, other bioactive agents, biological materials (for example, proteins), or even non-bioactive substances can be incorporated into the membranes of preferred embodiments.

Bioactive agents suitable for use in some embodiments are loosely organized into two groups: anti-barrier cell agents and vascularization agents. These designations reflect functions that are believed to provide short-term solute transport through the biointerface membrane, and additionally extend the life of a healthy vascular bed and hence solute transport through the biointerface membrane long term in vivo. However, not all bioactive agents can be clearly categorized into one or other of the above groups; rather, bioactive agents generally comprise one or more varying mechanisms for modifying tissue response and can be generally categorized into one or both of the above-cited categories.

Anti-Barrier Cell Agents

Generally, anti-barrier cell agents include compounds exhibiting affects on macrophages and foreign body giant cells (FBGCs). It is believed that anti-barrier cell agents prevent closure of the barrier to solute transport presented by macrophages and FBGCs at the device-tissue interface during FBC maturation.

Anti-barrier cell agents generally include mechanisms that inhibit foreign body giant cells and/or occlusive cell layers.

For example, Super Oxide Dismutase (SOD) Mimetic, which utilizes a manganese catalytic center within a porphyrin like molecule to mimic native SOD and effectively remove superoxide for long periods, thereby inhibiting FBGC formation at the surfaces of biomaterials in vivo, is incorporated into a biointerface membrane of one embodiment.

Anti-barrier cell agents can include anti-inflammatory and/or immunosuppressive mechanisms that affect early FBC formation. Cyclosporine, which stimulates very high levels of neovascularization around biomaterials, can be incorporated into a biointerface membrane of one embodiment (see U.S. Pat. No. 5,569,462 to Martinson et al.). Alternatively, Dexamethasone, which abates the intensity of the FBC response at the tissue-device interface, can be incorporated into a biointerface membrane of one embodiment. Alternatively, Rapamycin, which is a potent specific inhibitor of some macrophage inflammatory functions, can be incorporated into a biointerface membrane of one embodiment.

Other suitable medicaments, pharmaceutical compositions, therapeutic agents, or other desirable substances can be incorporated into the membranes of preferred embodiments, including, but not limited to, anti-inflammatory agents, anti-infective agents, necrosing agents, and anesthetics.

Generally, anti-inflammatory agents reduce acute and/or chronic inflammation adjacent to the implant, in order to decrease the formation of a FBC capsule to reduce or prevent barrier cell layer formation. Suitable anti-inflammatory agents include but are not limited to, for example, nonsteroidal anti-inflammatory drugs (NSAIDs) such as acetaminophen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (for example, L-NAME or L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

Generally, immunosuppressive and/or immunomodulatory agents interfere directly with several key mechanisms necessary for involvement of different cellular elements in the inflammatory response. Suitable immunosuppressive and/or immunomodulatory agents include anti-proliferative, cell-cycle inhibitors, (for example, paclitaxol (e.g., Sirolimus), cytochalasin D, infiximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincri sting, mitomycine, statins, C MYC antisense, sirolimus (and analogs), RestenASE, 2-chloro-deoxyadenosine, PCNA Ribozyme, batimstat, prolyl hydroxylase inhibitors, PPARγ ligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivasttin), *E. coli* heat-labile enterotoxin, and advanced coatings.

Generally, anti-infective agents are substances capable of acting against infection by inhibiting the spread of an infectious agent or by killing the infectious agent outright, which can serve to reduce immuno-response without inflammatory response at the implant site. Anti-infective agents include, but are not limited to, anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim.

Generally, a necrosing agent is any drug that causes tissue necrosis or cell death. Necrosing agents include cisplatin, BCNU, taxol or taxol derivatives, and the like.

Vascularization Agents

Generally, vascularization agents include substances with direct or indirect angiogenic properties. In some cases, vascularization agents may additionally affect formation of barrier cells in vivo. By indirect angiogenesis, it is meant that the angiogenesis can be mediated through inflammatory or immune stimulatory pathways. It is not fully known how agents that induce local vascularization indirectly inhibit barrier-cell formation; however it is believed that some barrier-cell effects can result indirectly from the effects of vascularization agents.

Vascularization agents include mechanisms that promote neovascularization around the membrane and/or minimize periods of ischemia by increasing vascularization close to the tissue-device interface. Sphingosine-1-Phosphate (S1P), which is a phospholipid possessing potent angiogenic activity, is incorporated into a biointerface membrane of one embodiment. Monobutyrin, which is a potent vasodilator and angiogenic lipid product of adipocytes, is incorporated into a biointerface membrane of one embodiment. In another embodiment, an anti-sense molecule (for example, thrombospondin-2 anti-sense), which increases vascularization, is incorporated into a biointerface membrane.

Vascularization agents can include mechanisms that promote inflammation, which is believed to cause accelerated neovascularization in vivo. In one embodiment, a xenogenic carrier, for example, bovine collagen, which by its foreign nature invokes an immune response, stimulates neovascularization, and is incorporated into a biointerface membrane of some embodiments. In another embodiment, Lipopolysaccharide, which is a potent immunostimulant, is incorporated into a biointerface membrane. In another embodiment, a protein, for example, a bone morphogenetic protein (BMP), which is known to modulate bone healing in tissue, is incorporated into a biointerface membrane of one embodiment.

Generally, angiogenic agents are substances capable of stimulating neovascularization, which can accelerate and sustain the development of a vascularized tissue bed at the tissue-device interface. Angiogenic agents include, but are not limited to, copper ions, iron ions, tridodecylmethylammonium chloride, Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Copper Sulphate, Estradiol, prostaglandins, cox inhibitors, endothelial cell binding agents (for example, decorin or vimentin), glenipin, hydrogen peroxide, nicotine, and Growth Hormone.

Generally, pro-inflammatory agents are substances capable of stimulating an immune response in host tissue, which can accelerate or sustain formation of a mature vascularized tissue bed. For example, pro-inflammatory agents are generally irritants or other substances that induce chronic inflammation and chronic granular response at the implantation-site. While not wishing to be bound by theory, it is believed that formation of high tissue granulation induces blood vessels, which supply an adequate or rich supply of analytes to the device-tissue interface. Pro-inflammatory agents include, but are not limited to, xenogenic carriers, Lipopolysaccharides, S. aureus peptidoglycan, and proteins.

Other substances that can be incorporated into membranes of preferred embodiments include various pharmacological agents, excipients, and other substances well known in the art of pharmaceutical formulations.

U.S. Patent Publication No. US-2005-0031689-A1 discloses a variety of systems and methods by which the bioactive agent can be incorporated into the biointerface membranes and/or implantable device. Although the bioactive agent is preferably incorporated into the biointerface membrane and/or implantable device, in some embodiments the bioactive agent can be administered concurrently with, prior to, or after implantation of the device systemically, for example, by oral administration, or locally, for example, by subcutaneous injection near the implantation site. A combination of bioactive agent incorporated in the biointerface membrane and bioactive agent administration locally and/or systemically can be preferred in certain embodiments.

Generally, numerous variables can affect the pharmacokinetics of bioactive agent release. The bioactive agents of some embodiments can be optimized for short- and/or long-term release. In some embodiments, the bioactive agents of some embodiments are designed to aid or overcome factors associated with short-term effects (for example, acute inflammation) of the foreign body response, which can begin as early as the time of implantation and extend up to about one month after implantation. In some embodiments, the bioactive agents of some embodiments are designed to aid or overcome factors associated with long-term effects, for example, chronic inflammation, barrier cell layer formation, or build-up of fibrotic tissue of the foreign body response, which can begin as early as about one week after implantation and extend for the life of the implant, for example, months to years. In some embodiments, the bioactive agents of some embodiments combine short- and long-term release to exploit the benefits of both. U.S. Patent Publication No. US-2005-0031689-A1 discloses a variety of systems and methods for release of the bioactive agents.

The amount of loading of the bioactive agent into the biointerface membrane can depend upon several factors. For example, the bioactive agent dosage and duration can vary with the intended use of the biointerface membrane, for example, cell transplantation, analyte measuring-device, and the like; differences among hosts in the effective dose of bioactive agent; location and methods of loading the bioactive agent; and release rates associated with bioactive agents and optionally their carrier matrix. Therefore, one skilled in the art will appreciate the variability in the levels of loading the bioactive agent, for the reasons described above. U.S. Patent Publication No. US-2005-0031689-A1, which is incorporated herein by reference in its entirety, discloses a variety of systems and methods for loading of the bioactive agents.

Exemplary Sensor Configurations

Figure 5A:
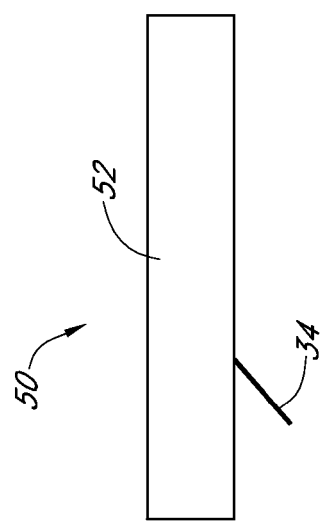
FIG. 5A is a side schematic view of a transcutaneous analyte sensor in one embodiment.

FIG. 5A is a side schematic view of a transcutaneous analyte sensor 50 in one embodiment. The sensor 50 includes a mounting unit 52 adapted for mounting on the skin of a host, a small diameter sensor 34 (as defined herein) adapted for transdermal insertion through the skin of a host, and an electrical connection configured to provide secure electrical contact between the sensor and the electronics preferably housed within the mounting unit 52. In general, the mounting unit 52 is designed to maintain the integrity of the sensor in the host so as to reduce or eliminate translation of motion between the mounting unit, the host, and/or the sensor. See U.S. Patent Publication No. US-2006-0020187-A1, which is incorporated herein by reference in its entirety. Preferably, a biointerface membrane is formed onto the sensing mechanism 34 as described in more detail below.

Figure 5B:
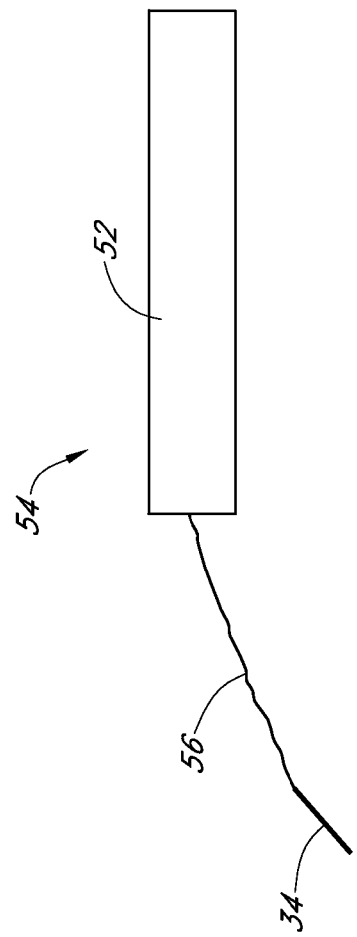
FIG. 5B is a side schematic view of a transcutaneous analyte sensor in an alternative embodiment.

FIG. 5B is a side schematic view of a transcutaneous analyte sensor 54 in an alternative embodiment. The sensor 54 includes a mounting unit 52 wherein the sensing mechanism 34 comprises a small structure as defined herein and is tethered to the mounting unit 52 via a cable 56 (alternatively, a wireless connection can be utilized). The mounting unit is adapted for mounting on the skin of a host and is operably connected via a tether, or the like, to a small structured sensor 34 adapted for transdermal insertion through the skin of a host and measurement of the analyte therein; see, for example, U.S. Pat. No. 6,558,330, which is incorporated herein by reference in its entirety. In some embodiments, a biointerface membrane is formed onto the sensing mechanism 34 as described in more detail below.

The sensor of some embodiments may be inserted into a variety of locations on the host's body, such as the abdomen, the thigh, the upper arm, and the neck or behind the ear. Although some embodiments illustrate insertion through the abdominal region, the systems and methods described herein are limited neither to the abdominal nor to the subcutaneous insertions. One skilled in the art appreciates that these systems and methods may be implemented and/or modified for other insertion sites and may be dependent upon the type, configuration, and dimensions of the analyte sensor.

In one embodiment, an analyte-sensing device adapted for transcutaneous short-term insertion into the host is provided. For example, the device includes a sensor, for measuring the analyte in the host, a porous, biocompatible matrix covering at least a portion of the sensor, and an applicator, for inserting the sensor through the host's skin. In some embodiments, the sensor has architecture with at least one dimension less than about 1 mm. Examples of such a structure are shown in FIGS. 3A and 3B, as described elsewhere herein. However, one skilled in the art will recognize that alternative configurations are possible and may be desirable, depending upon factors such as intended location of insertion, for example. The sensor is inserted through the host's skin and into the underlying tissue, such as soft tissue or fatty tissue.

After insertion, fluid moves into the spacer, e.g., a biocompatible matrix or membrane, creating a fluid-filled pocket therein. This process may occur immediately or may take place over a period of time, such as several minutes or hours post insertion. A signal from the sensor is then detected, such as by the sensor electronics unit located in the mounting unit on the surface of the host's skin. In some circumstances, a sensor may be used continuously for a short period of days, such as 1 to 14 days. After use, the sensor is simply removed from the host's skin. In preferred embodiments, the host may repeat the insertion and detection steps as many times as desired. In some implementations, the sensor may be removed after about 3 days, and then another sensor inserted, and so on. Similarly in other implementations, the sensor is removed after about 3, 5, 7, 10, 14 or more days, followed by insertion of a new sensor, and so on.

Some examples of transcutaneous analyte sensors are described in U.S. patent application Ser. No. 11/360,250, filed Feb. 22, 2006 and entitled "ANALYTE SENSOR," which is incorporated herein by reference in its entirety. In general, transcutaneous analyte sensors comprise the sensor and a mounting unit with electronics associated therewith.

Referring again to FIGS. 5A-5B, in general, the mounting unit includes a base adapted for mounting on the skin of a host, a sensor 34 adapted for transdermal insertion through the skin of a host, and one or more contacts configured to provide secure electrical contact between the sensor and the sensor electronics. The mounting unit is designed to maintain the integrity of the sensor in the host so as to reduce or eliminate translation of motion between the mounting unit, the host, and/or the sensor.

The base can be formed from a variety of hard or soft materials, and preferably comprises a low profile for minimizing protrusion of the device from the host during use. In some embodiments, the base is formed at least partially from a flexible material, which is believed to provide numerous advantages over conventional transcutaneous sensors, which, unfortunately, can suffer from motion-related artifacts associated with the host's movement when the host is using the device. For example, when a transcutaneous analyte sensor is inserted into the host, various movements of the sensor (for example, relative movement between the in vivo portion and the ex vivo portion, movement of the skin, and/or movement within the host (dermis or subcutaneous)) create stresses on the device and can produce noise in the sensor signal. It is believed that even small movements of the skin can translate to discomfort and/or motion-related artifact, which can be reduced or obviated by a flexible or articulated base. Thus, by providing flexibility and/or articulation of the device against the host's skin, better conformity of the sensor system to the regular use and movements of the host can be achieved. Flexibility or articulation is believed to increase adhesion (with the use of an adhesive pad) of the mounting unit onto the skin, thereby decreasing motion-related artifact that can otherwise translate from the host's movements and reduced sensor performance. Adhesive pads that are compatible the sensor system described herein are discussed in U.S. Patent Publication No. US-2006-0270923-A1, which is incorporated herein by reference in its entirety.

A bioactive agent is preferably applied locally at the insertion site prior to or during sensor insertion. Suitable bioactive agents include those which are known to discourage or prevent bacterial growth and infection, for example, anti-inflammatory agents, antimicrobials, antibiotics, or the like. It is believed that the diffusion or presence of a bioactive agent can aid in prevention or elimination of bacteria adjacent to the exit-site. Additionally or alternatively, the bioactive agent can be integral with or coated on the adhesive pad, or no bioactive agent at all is employed.

In some embodiments, an applicator is provided for inserting the sensor through the host's skin at the appropriate insertion angle with the aid of a needle, and for subsequent removal of the needle using a continuous push-pull action. Preferably, the applicator comprises an applicator body that guides the applicator and includes an applicator body base configured to mate with the mounting unit during insertion of the sensor into the host. The mate between the applicator body base and the mounting unit can use any known mating configuration, for example, a snap-fit, a press-fit, an interference-fit, or the like, to discourage separation during use. One or more release latches enable release of the applicator body base, for example, when the applicator body base is snap fit into the mounting unit.

The sensor electronics includes hardware, firmware, and/or software that enable measurement of levels of the analyte via the sensor. For example, the sensor electronics can comprise a potentiostat, a power source for providing power to the sensor, other components useful for signal processing, and preferably an RF module for transmitting data from the sensor electronics to a receiver. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, or a processor. Preferably, sensor electronics comprise systems and methods for processing sensor analyte data. Examples of systems and methods for processing sensor analyte data are described in more detail below and in U.S. Patent Publication No. US-2005-0027463-A1.

In this embodiment, after insertion of the sensor using the applicator, and subsequent release of the applicator from the mounting unit, the sensor electronics are configured to releasably mate with the mounting unit. In one embodiment, the electronics are configured with programming, for example initialization, calibration reset, failure testing, or the like, each time it is initially inserted into the mounting unit and/or each time it initially communicates with the sensor.

Figure 5C:
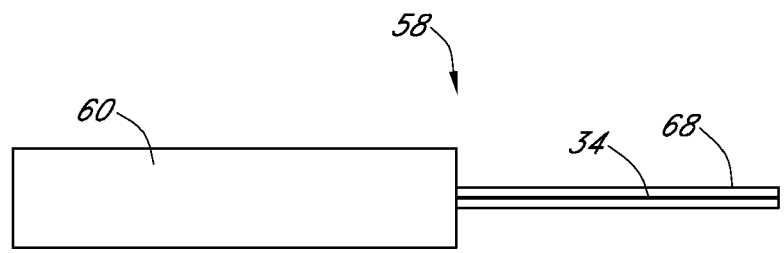
FIG. 5C is a side schematic view of a wholly implantable analyte sensor in one embodiment.

FIG. 5C is a side schematic view of a wholly implantable analyte sensor 58 in one embodiment. The sensor includes a sensor body 60 suitable for subcutaneous implantation and includes a small structured sensor 34 as defined herein. U.S. Patent Publication No. US-2004-0199059-A1 describes systems and methods suitable for the sensor body 60, and is incorporated herein by reference in its entirety. In some embodiments, a biointerface membrane 68 is formed onto the sensing mechanism 34 as described in more detail elsewhere herein. The sensor body 60 includes sensor electronics and preferably communicates with a receiver as described in more detail, above.

Figure 5D:
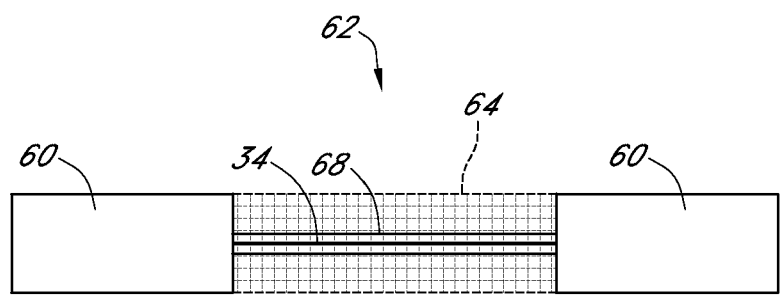
FIG. 5D is a side schematic view of a wholly implantable analyte sensor in an alternative embodiment.

FIG. 5D is a side schematic view of a wholly implantable analyte sensor 62 in an alternative embodiment. The sensor 62 includes a sensor body 60 and a small structured sensor 34 as defined herein. The sensor body 60 includes sensor electronics and preferably communicates with a receiver as described in more detail, above.

In preferred embodiments, a biointerface membrane 68 is formed onto the sensing mechanism 34 as described in more detail elsewhere herein. Preferably, a matrix or framework 64 surrounds the sensing mechanism 34 for protecting the sensor from some foreign body processes, for example, by causing tissue to compress against or around the framework 64 rather than the sensing mechanism 34.

In general, the optional protective framework 64 is formed from a two-dimensional or three-dimensional flexible, semi-rigid, or rigid matrix (e.g., mesh), and which includes spaces or pores through which the analyte can pass. In some embodiments, the framework is incorporated as a part of the biointerface membrane, however a separate framework can be provided. While not wishing to be bound by theory, it is believed that the framework 64 protects the small structured sensing mechanism from mechanical forces created in vivo.

Figure 5E:
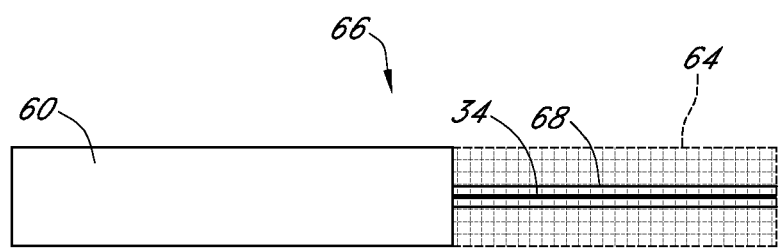
FIG. 5E is a side schematic view of a wholly implantable analyte sensor in another alternative embodiment.

FIG. 5E is a side schematic view of a wholly implantable analyte sensor 66 in another alternative embodiment. The sensor 66 includes a sensor body 60 and a small structured sensor 34, as defined herein, with a biointerface membrane 68 such as described in more detail elsewhere herein. Preferably, a framework 64 protects the sensing mechanism 34 such as described in more detail above. The sensor body 60 includes sensor electronics and preferably communicates with a receiver as described in more detail, above.

In certain embodiments, the sensing device, which is adapted to be wholly implanted into the host, such as in the soft tissue beneath the skin, is implanted subcutaneously, such as in the abdomen of the host, for example. One skilled in the art appreciates a variety of suitable implantation sites available due to the sensor's small size. In some embodiments, the sensor architecture is less than about 0.5 mm in at least one dimension, for example a wire-based sensor with a diameter of less than about 0.5 mm. In another exemplary embodiment, for example, the sensor may be 0.5 mm thick, 3 mm in length and 2 cm in width, such as possibly a narrow substrate, needle, wire, rod, sheet, or pocket. In another exemplary embodiment, a plurality of about 1 mm wide wires about 5 mm in length could be connected at their first ends, producing a forked sensor structure. In still another embodiment, a 1 mm wide sensor could be coiled, to produce a planar, spiraled sensor structure. Although a few examples are cited above, numerous other useful embodiments are contemplated by the present invention, as is appreciated by one skilled in the art.

Post implantation, a period of time is allowed for tissue ingrowth within the biointerface. The length of time required for tissue ingrowth varies from host to host, such as about a week to about 3 weeks, although other time periods are also possible. Once a mature bed of vascularized tissue has grown into the biointerface, a signal can be detected from the sensor, as described elsewhere herein and in U.S. Patent Publication No. US-2005-0245799-A1, incorporated herein in its entirety. Long-term sensors can remain implanted and produce glucose signal information from months to years, as described in the above-cited patent application.

In certain embodiments, the device is configured such that the sensing unit is separated from the electronics unit by a tether or cable, or a similar structure, similar to that illustrated in FIG. 5B. One skilled in the art will recognize that a variety of known and useful means may be used to tether the sensor to the electronics. While not wishing to be bound by theory, it is believed that the FBR to the electronics unit alone may be greater than the FBR to the sensing unit alone, due to the electronics unit's greater mass, for example. Accordingly, separation of the sensing and electronics units effectively reduces the FBR to the sensing unit and results in improved device function. As described elsewhere herein, the architecture and/or composition of the sensing unit (e.g., inclusion of a biointerface with certain bioactive agents) can be implemented to further reduce the foreign body response to the tethered sensing unit.

Figure 5F:
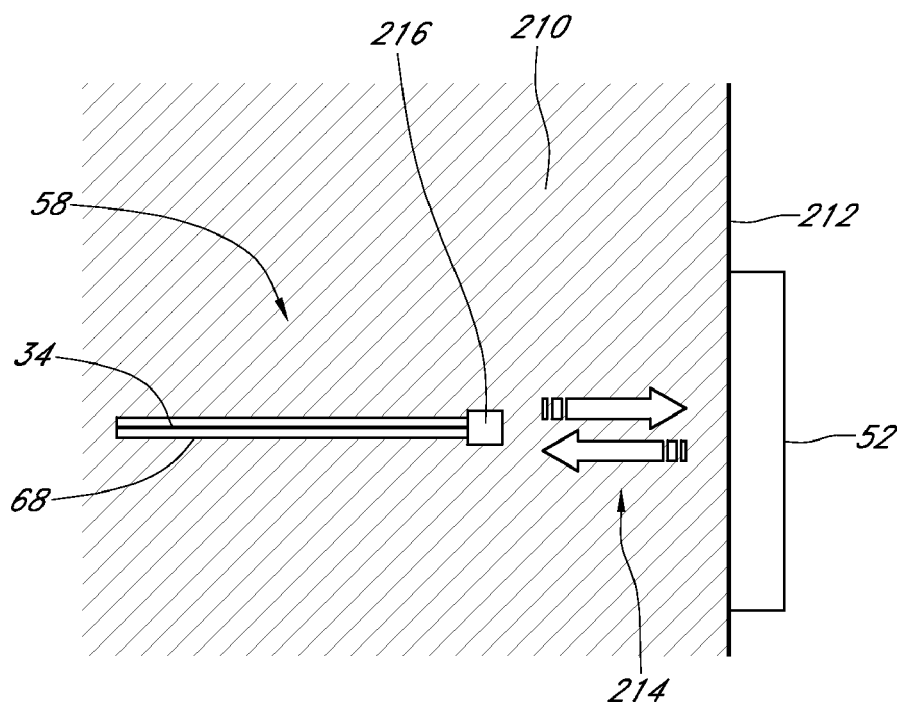
FIG. 5F is a side view of one embodiment of an implanted sensor inductively coupled to an electronics unit within a functionally useful distance on the host's skin.
Figure 5G:
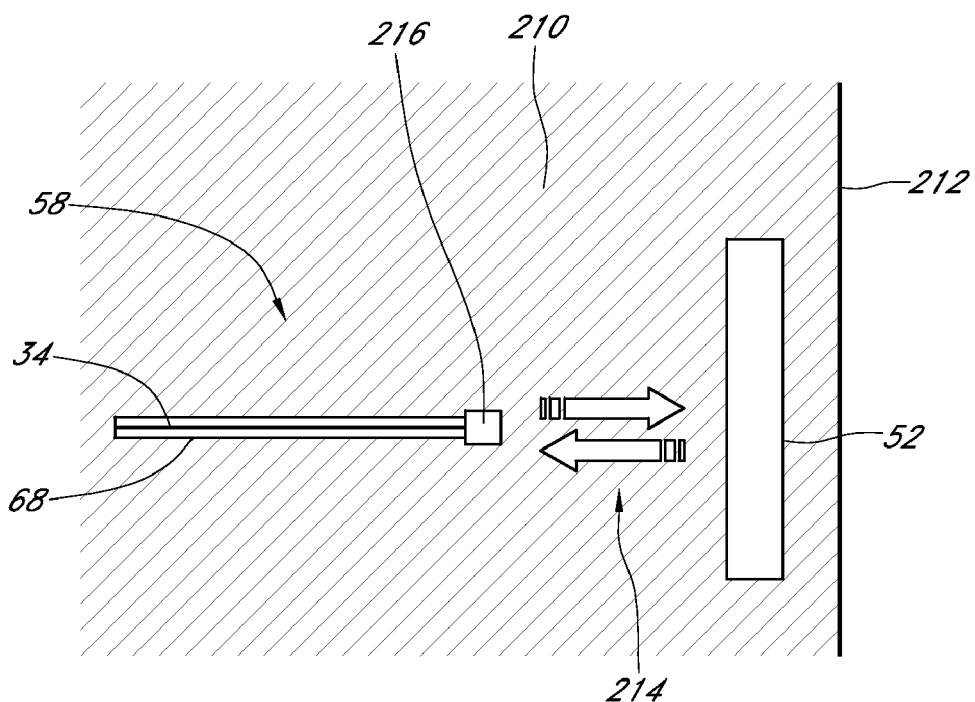
FIG. 5G is a side view of one embodiment of an implanted sensor inductively coupled to an electronics unit implanted in the host's tissue at a functionally useful distance.

In another embodiment, an analyte sensor is designed with separate electronics and sensing units, wherein the sensing unit is inductively coupled to the electronics unit. In this embodiment, the electronics unit provides power to the sensing unit and/or enables communication of data therebetween. FIGS. 5F and 5G illustrate exemplary systems that employ inductive coupling between an electronics unit 52 and a sensing unit 58.

FIG. 5F is a side view of one embodiment of an implanted sensor inductively coupled to an electronics unit within a functionally useful distance on the host's skin. FIG. 5G illustrates a sensing unit 58, including a sensing mechanism 34, biointerface 68 and small electronics chip 216 implanted below the host's skin 212, within the host's tissue 210. In this example, the majority of the electronics associated with the sensor are housed in an electronics unit 52 (also referred to as a mounting unit) located within suitably close proximity on the host's skin. The electronics unit 52 is inductively coupled to the small electronics chip 216 on the sensing unit 58 and thereby transmits power to the sensor and/or collects data, for example. The small electronics chip 216 coupled to the sensing unit 58 provides the necessary electronics to provide a bias potential to the sensor, measure the signal output, and/or other necessary requirements to allow the sensing mechanism 58 to function (e.g., chip 216 can include an ASIC (application specific integrated circuit), antenna, and other necessary components appreciated by one skilled in the art).

In yet another embodiment, the implanted sensor additionally includes a capacitor to provide necessary power for device function. A portable scanner (e.g., wand-like device) is used to collect data stored on the circuit and/or to recharge the device.

In general, inductive coupling, as described herein, enables power to be transmitted to the sensor for continuous power, recharging, and the like. Additionally, inductive coupling utilizes appropriately spaced and oriented antennas (e.g., coils) on the sensing unit and the electronics unit so as to efficiently transmit/receive power (e.g., current) and/or data communication therebetween. One or more coils in each of the sensing and electronics unit can provide the necessary power induction and/or data transmission.

In this embodiment, the sensing mechanism can be, for example, a wire-based sensor as described in more detail with reference to FIGS. 4A and 4B and as described in published U.S. Patent Publication No. US-2006-0020187-A1, or a planar substrate-based sensor such as described in U.S. Pat. No. 6,175,752 to Say et al. and U.S. Pat. No. 5,779,665 to Mastrototaro et al., each of which is incorporated herein by reference in its entirety. The biointerface 68 can be any suitable biointerface as described in more detail elsewhere herein, for example, a layer of porous biointerface membrane material, a mesh cage, and the like. In one exemplary embodiment, the biointerface 68 is a single- or multi-layer sheet (e.g., pocket) of porous membrane material, such as ePTFE, in which the sensing mechanism 34 is incorporated.

FIG. 5G is a side view of on embodiment of an implanted sensor inductively coupled to an electronics unit implanted in the host's tissue at a functionally useful distance. FIG. 5G illustrates a sensor unit 58 and an electronics unit 52 similar to that described with reference to FIG. 5F, above, however both are implanted beneath the host's skin in a suitably close proximity.

In general, it is believed that when the electronics unit 52, which carries the majority of the mass of the implantable device, is separate from the sensing unit 58, a lesser foreign body response will occur surrounding the sensing unit (e.g., as compared to a device of greater mass, for example, a device including certain electronics and/or power supply). Thus, the configuration of the sensing unit, including a biointerface, can be optimized to minimize and/or modify the host's tissue response, for example with minimal mass as described in more detail elsewhere.

In alternative embodiments, the sensor, including the membrane system and other components described herein, is configured for implantation into the vascular system, such as but not limited to insertion into a peripheral vein or artery or into a central vein or artery. In one exemplary embodiment, the sensor comprises at least one fine wire electrode (e.g., including a membrane system) connected to a fluid coupler and temporarily supported by a sheath that protects the sensor during insertion into a catheter placed in a host's peripheral vein, for example. In other embodiments, the sensor is configured for implantation into the vena cava. In still another embodiment, the sensor is configured for insertion into an extracorporeal circulatory system, such as but not limited to a dialysis machine or heart-lung machine. For example, the extracorporeal sensor can be inserted into the tubing of the extracorporeal circulatory system (e.g., via a catheter piercing and inserted into the tubing). In another example, the extracorporeal sensor can be inserted into a shunt, such as but not limited to an arterial-venous shunt, by inserting the sensor directly into the tubing of the shunt. In some embodiments, the sensor is contained in a catheter (e.g., and may or may not extend out of the catheter) or the sensor may be incorporated into the catheter. Additional embodiments are disclosed in detail in co-pending U.S. patent application Ser. No. 11/543,396, filed on Oct. 4, 2006, and entitled "ANALYTE SENSOR," which is incorporated herein by reference.

In other embodiments, the sensor, including the membrane system and other components described herein, is configured for implantation below the host's skin, such as but not limited to implantation in the subcutaneous tissue (e.g., wholly implantable). In one exemplary embodiment, the sensor comprises an electrode system that includes three electrodes (working, counter, and reference electrodes), wherein the counter electrode is provided to balance the current generated by the species being measured at the working electrode, and a membrane system as described herein. In some embodiments, the sensor is configured to be implanted in the abdomen of a host. In alternative embodiments, the sensor is configured to be implanted in the arm, leg or chest of a host, for example, in the upper arm, thigh, buttocks or any other body portion having sufficient subcutaneous tissue to contain the sensor. Additional embodiments are disclosed in detail in co-pending U.S. Patent Publication No. US-2005/0054909-A1, which is incorporated herein by reference.

In addition to the devices discussed herein, some alternative analyte sensors that can benefit from the systems and methods of some embodiments include U.S. Pat. No. 5,711,861 to Ward et al., U.S. Pat. No. 6,642,015 to Vachon et al., U.S. Pat. No. 6,654,625 to Say et al., U.S. Pat. No. 6,565,509 to Say et al., U.S. Pat. No. 6,514,718 to Heller, U.S. Pat. No. 6,465,066 to Essenpreis et al., U.S. Pat. No. 6,214,185 to Offenbacher et al., U.S. Pat. No. 5,310,469 to Cunningham et al., and U.S. Pat. No. 5,683,562 to Shaffer et al., U.S. Pat. No. 6,579,690 to Bonnecaze et al., U.S. Pat. No. 6,484,046 to Say et al., U.S. Pat. No. 6,512,939 to Colvin et al., U.S. Pat. No. 6,424,847 to Mastrototaro et al., U.S. Pat. No. 6,424,847 to Mastrototaro et al., for example. All of the above patents are incorporated in their entirety herein by reference and are not inclusive of all applicable analyte sensors; in general, it should be understood that the disclosed embodiments are applicable to a variety of analyte sensor configurations.

Sensor Electronics

The following description of electronics associated with the sensor is applicable to a variety of continuous analyte sensors, such as non-invasive, minimally invasive, and/or invasive (e.g. transcutaneous and wholly implantable) sensors. For example, the sensor electronics and data processing as well as the receiver electronics and data processing described below can be incorporated into the wholly implantable glucose sensor disclosed in co-pending U.S. Patent Publication No. US-2005-0245799-A1 and U.S. Patent Publication No. US-2006-0015020-A1.

In one embodiment, a potentiostat, which is operably connected to an electrode system (such as described above) provides a voltage to the electrodes, which biases the sensor to enable measurement of a current signal indicative of the analyte concentration in the host (also referred to as the analog portion). In some embodiments, the potentiostat includes a resistor that translates the current into voltage. In some alternative embodiments, a current to frequency converter is provided that is configured to continuously integrate the measured current, for example, using a charge counting device. An A/D converter digitizes the analog signal into a digital signal, also referred to as "counts" for processing. Accordingly, the resulting raw data stream in counts, also referred to as raw sensor data, is directly related to the current measured by the potentiostat.

A processor module includes the central control unit that controls the processing of the sensor electronics. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in U.S. Patent Publication No. US-2005-0043598-A1. The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, or the like.

In some embodiments, the processor module comprises a digital filter, for example, an IIR or FIR filter, configured to smooth the raw data stream from the A/D converter. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter as described above, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is preferred; however any acquisition time can be programmed into the processor module. A programmable acquisition time is advantageous in optimizing noise filtration, time lag, and processing/battery power.

Preferably, the processor module is configured to build the data packet for transmission to an outside source, for example, an RF transmission to a receiver as described in more detail below. Generally, the data packet comprises a plurality of bits that can include a sensor ID code, raw data, filtered data, and/or error detection or correction. The processor module can be configured to transmit any combination of raw and/or filtered data.

In some embodiments, the processor module further comprises a transmitter portion that determines the transmission interval of the sensor data to a receiver, or the like. In some embodiments, the transmitter portion, which determines the interval of transmission, is configured to be programmable. In one such embodiment, a coefficient can be chosen (e.g. a number of from about 1 to about 100, or more), wherein the coefficient is multiplied by the acquisition time (or sampling rate), such as described above, to define the transmission interval of the data packet. Thus, in some embodiments, the transmission interval is programmable from about 2 seconds to about 850 minutes, more preferably from about 30 second to about 5 minutes; however, any transmission interval can be programmable or programmed into the processor module. However, a variety of alternative systems and methods for providing a programmable transmission interval can also be employed. By providing a programmable transmission interval, data transmission can be customized to meet a variety of design criteria (e.g. reduced battery consumption, timeliness of reporting sensor values, etc.)

Conventional glucose sensors measure current in the nano-Amp range. In contrast to conventional glucose sensors, some embodiments are configured to measure the current flow in the picoAmp range, and in some embodiments, femtoAmps. Namely, for every unit (mg/dL) of glucose measured, at least one picoAmp of current is measured. Preferably, the analog portion of the A/D converter is configured to continuously measure the current flowing at the working electrode and to convert the current measurement to digital values representative of the current. In one embodiment, the current flow is measured by a charge counting device (e.g. a capacitor). Thus, a signal is provided, whereby a high sensitivity maximizes the signal received by a minimal amount of measured hydrogen peroxide (e.g. minimal glucose requirements without sacrificing accuracy even in low glucose ranges), reducing the sensitivity to oxygen limitations in vivo (e.g. in oxygen-dependent glucose sensors).

A battery is operably connected to the sensor electronics and provides the power for the sensor. In one embodiment, the battery is a lithium manganese dioxide battery; however, any appropriately sized and powered battery can be used (for example, AAA, nickel-cadmium, zinc-carbon, alkaline, lithium, nickel-metal hydride, lithium-ion, zinc-air, zinc-mercury oxide, silver-zinc, and/or hermetically-sealed). In some embodiments, the battery is rechargeable, and/or a plurality of batteries can be used to power the system. The sensor can be transcutaneously powered via an inductive coupling, for example. In some embodiments, a quartz crystal is operably connected to the processor and maintains system time for the computer system as a whole, for example for the programmable acquisition time within the processor module.

Optional temperature probe can be provided, wherein the temperature probe is located on the electronics assembly or the glucose sensor itself. The temperature probe can be used to measure ambient temperature in the vicinity of the glucose sensor. This temperature measurement can be used to add temperature compensation to the calculated glucose value.

An RF module is operably connected to the processor and transmits the sensor data from the sensor to a receiver within a wireless transmission via antenna. In some embodiments, a second quartz crystal provides the time base for the RF carrier frequency used for data transmissions from the RF transceiver. In some alternative embodiments, however, other mechanisms, such as optical, infrared radiation (IR), ultrasonic, or the like, can be used to transmit and/or receive data.

In the RF telemetry module of some embodiments, the hardware and software are designed for low power requirements to increase the longevity of the device (for example, to enable a life of from about 3 months to about 24 months, or more) with maximum RF transmittance from the in vivo environment to the ex vivo environment for wholly implantable sensors (for example, a distance o from about one meter to about ten meters or more). Preferably, a high frequency carrier signal from about 402 MHz to about 433 MHz is employed in order to maintain lower power requirements. Additionally, in wholly implantable devices, the carrier frequency is adapted for physiological attenuation levels, which is accomplished by tuning the RF module in a simulated in vivo environment to ensure RF functionality after implantation; accordingly, the glucose sensor can sustain sensor function for 3 months, 6 months, 12 months, or 24 months or more.

In some embodiments, output signal (from the sensor electronics) is sent to a receiver (e.g., a computer or other communication station). The output signal is typically a raw data stream that is used to provide a useful value of the measured analyte concentration to a patient or a doctor, for example. In some embodiments, the raw data stream can be continuously or periodically algorithmically smoothed or otherwise modified to diminish outlying points that do not accurately represent the analyte concentration, for example due to signal noise or other signal artifacts, such as described in U.S. Pat. No. 6,931,327, which is incorporated herein by reference in its entirety.

When a sensor is first implanted into host tissue, the sensor and receiver are initialized. This can be referred to as start-up mode, and involves optionally resetting the sensor data and calibrating the sensor. In selected embodiments, mating the electronics unit to the mounting unit triggers a start-up mode. In other embodiments, the start-up mode is triggered by the receiver.

Receiver

In some embodiments, the sensor electronics are wirelessly connected to a receiver via one- or two-way RF transmissions or the like. However, a wired connection is also contemplated. The receiver provides much of the processing and display of the sensor data, and can be selectively worn and/or removed at the host's convenience. Thus, the sensor system can be discreetly worn, and the receiver, which provides much of the processing and display of the sensor data, can be selectively worn and/or removed at the host's convenience. Particularly, the receiver includes programming for retrospectively and/or prospectively initiating a calibration, converting sensor data, updating the calibration, evaluating received reference and sensor data, and evaluating the calibration for the analyte sensor, such as described in more detail with reference to U.S. Patent Publication No. US-2005-0027463-A1.

EXAMPLES

Example 1

Small-Structured Sensor Construction

A short term (transcutaneous) sensor was built by providing a platinum wire, vapor-depositing the platinum with Parylene to form an insulating coating, helically winding a silver wire around the insulated platinum wire (to form a "twisted pair"), masking sections of electroactive surface of the silver wire, vapor-depositing Parylene on the twisted pair, chloridizing the silver electrode to form silver chloride reference electrode, and removing a radial window on the insulated platinum wire to expose a circumferential electroactive working electrode surface area thereon, this assembly also referred to as a "parylene-coated twisted pair assembly."

An electrode domain was formed over the parylene-coated twisted pair assembly by coating the assembly with a polyurethane-latex dispersion (Bayhydrol® 123 available from Bayer Material Sciences, Pittsburgh, Pa., USA) crosslinked with EDC in the presence of PVP; followed by curing at about 50° C. An enzyme domain was formed over the electrode domain by dip coating the assembly in an enzyme domain solution and drying in a vacuum oven for 20 minutes at 50° C. This dip coating process was repeated once more to form an enzyme domain comprised of two layers. A resistance domain was formed over the enzyme domain by subsequently spray coating the assembly with a resistance domain solution and dried in a vacuum oven for 60 minutes at 50° C. Both the electrode domain and the resistance domain were formed as described in more detail in U.S. Patent Publication No. US-2006-0020187-A1, incorporated herein by reference.

Example 2

MED-4840/PLURONIC® F-127 Cell Impermeable Domain 30 g of PLURONIC® F-127 (PF-127) was dissolved under stirring in 100 g of anhydrous acetone at 40° C. 13 g of acetone was added to 37.3 g of the PF-127 solution followed by adding 4.8 g of dicumyl peroxide (DCP). 40 g of MED-4840 was mixed in a speed mixer at a speed of 3300 rpm for 60 seconds. The MED-4840 mixture was then placed in a motorized mechanical mixer equipped with a spiral dough hook. The mixture was stirred at low speed for 30 s. The stirring speed was then increased to medium-low and the PF-127/DCP solution was added at a rate of 3.5-4.0 g every 30 seconds. After all of the PF-127/DCP solution was added, the mixture was stirred at medium speed for 3 minutes. The mixture was then placed in a Speed Mixer and mixed at 3300 rpm for 60 seconds. Additional acetone was added (repeatedly), followed by stirring, until the desired viscosity was reached.

5-10 mL of the mixture was placed in an evenly distributed line between the arms of the drawdown blade on a drawdown machine. The drawdown machine was used to create a 9-inch long and 0.0045-inch thick film at a speed of about 0.7 inches/minute. A preformed piece of porous silicone (to act as a cell disruptive layer) was placed skin side down on the drawn film and tapped lightly to promote the polymeric mixture to penetrate into the pores of the porous silicone. The film was then cured for 1.5 hours at 100° C.

Example 3

MED-4840/PLURONIC® F-127 Diffusion Resistance Domain on Implanted Sensor

Figure 6:
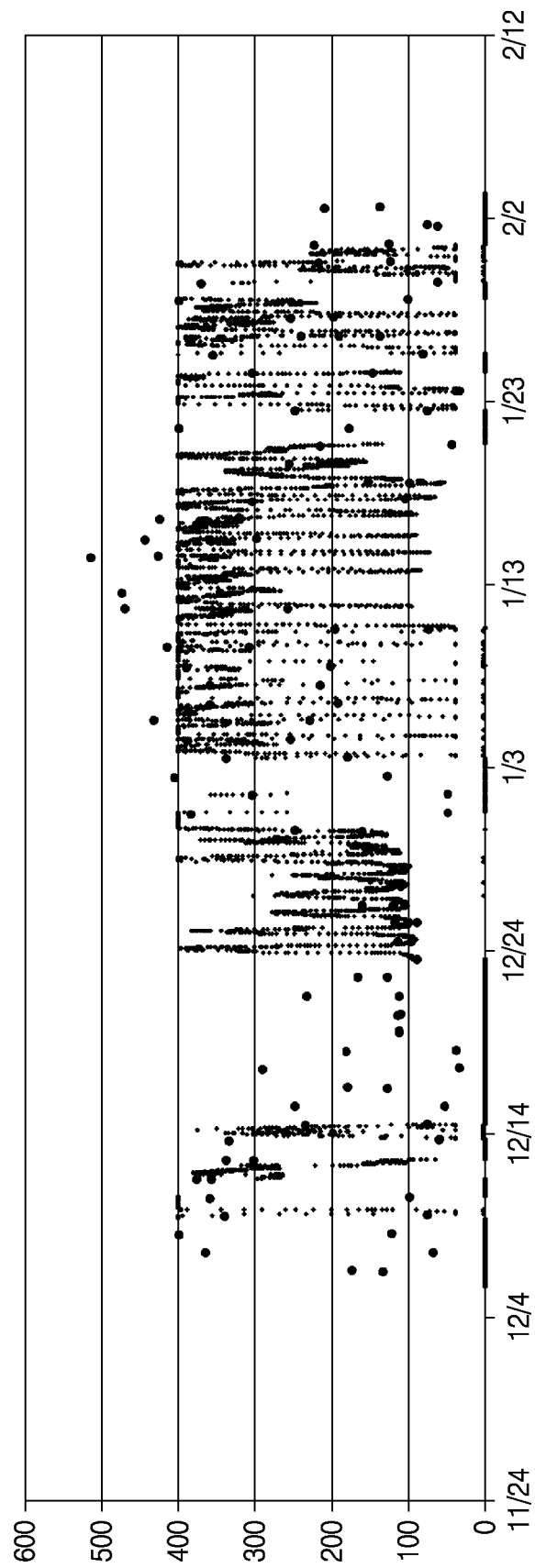
FIG. 6 is a graph depicting glucose measurements from a sensor including a silicone/hydrophilic-hydrophobic polymer blend in a diffusion resistance domain implanted in a diabetic rat model.

A MED-4840/PLURONIC® F-127 membrane was manufactured using 8.4% PLURONIC® and 1.8% of a DCP cross-linking agent. This membrane was placed over a two-layer membrane having an enzyme domain and an electrode domain. The combined membrane layers were placed on a wholly implantable glucose sensor. The sensor was sterilized and implanted into a diabetic rat model. FIG. 6 is a graph depicting the resulting glucose sensor measurements over the course of approximately two months. The small points in FIG. 4 depict glucose concentrations measured by the sensor and the large points depict glucose concentrations measured by separate blood glucose assays. The graph indicates a close correlation between the sensor glucose measurements and the blood glucose measurements.

Example 4

MED-4840/PLURONIC® F-127 Cell Impermeable Domain on Implanted Sensor

Figure 7:
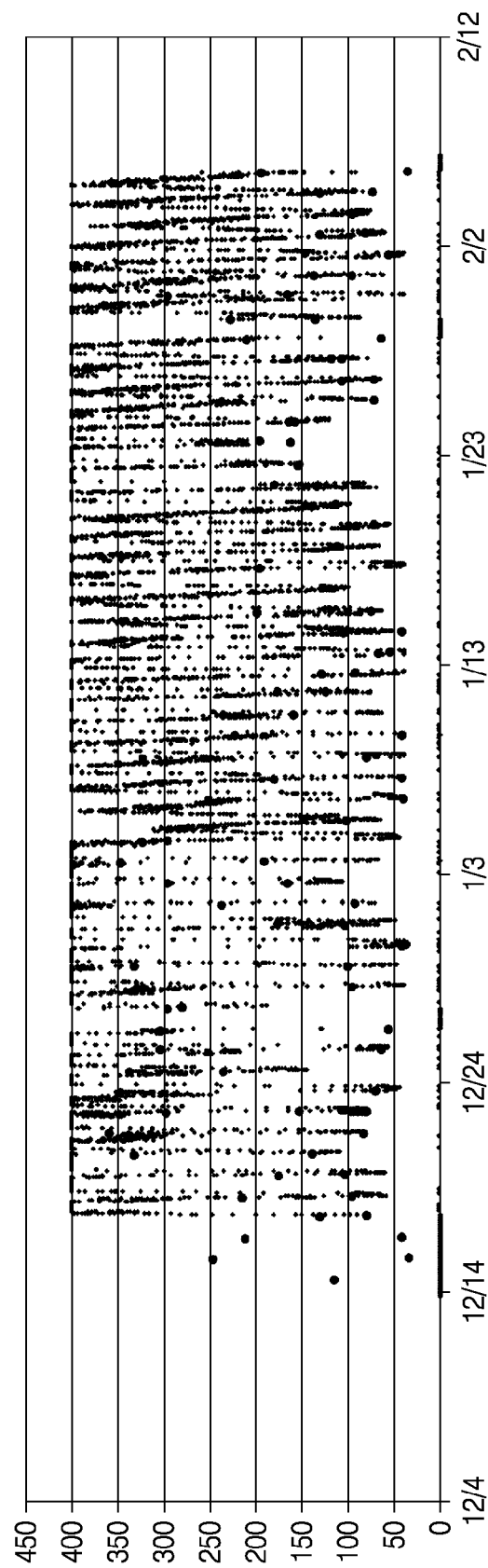
FIG. 7 is a graph depicting glucose measurements from a sensor including a silicone/hydrophilic-hydrophobic polymer blend in a bioprotective layer implanted in a diabetic rat model.

A MED-4840/PLURONIC® F-127 membrane was manufactured using 20% PLURONIC® and a 20:1 ratio of DCP cross-linking agent per PLURONIC®. Prior to curing, the material was drawn down and a cell-disruptive porous silicone membrane was placed on the uncured layer. After curing, the combined bioprotective/porous silicone membrane was placed over a four-layer membrane having a diffusion resistance domain, enzyme domain, interference layer, and electrode domain. The combined membrane layers were placed on a wholly implantable glucose sensor. The sensor was sterilized and implanted into a diabetic rat model. FIG. 5 is a graph depicting the resulting glucose sensor measurements over the course of approximately two months. The small points in FIG. 7 depict glucose concentrations measured by the sensor and the large points depict glucose concentrations measured by separate blood glucose assays. The graph indicates a close correlation between the sensor glucose measurements and the blood glucose measurements.

Example 5

Figure 8:
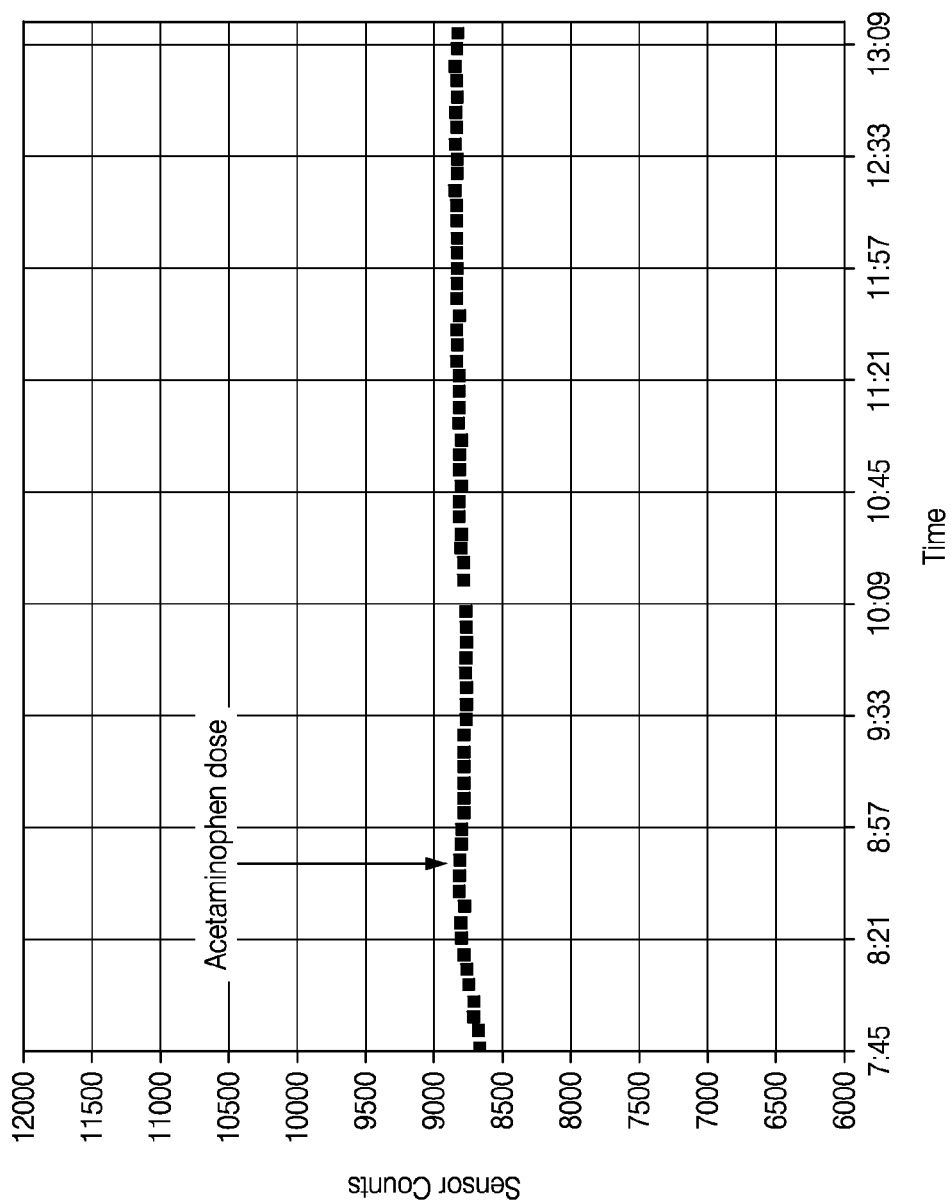
FIG. 8 is a graph depicting a sensor signal from a sensor including a silicone/hydrophilic-hydrophobic polymer blend membrane exposed to acetaminophen.

MED-4840/PLURONIC® F-127 Diffusion Resistance Domain Interference Properties A MED-4840/PLURONIC® F-127 membrane was manufactured using 8.4% PLURONIC® and 3.7% DCP. This membrane was placed over two-layer membrane having an electrode domain and an enzyme domain. The combined membrane layers were installed on a wholly implantable glucose sensor. The sensor was placed into a 2 L bath filled with PBS (saline). The continuously stirred bath was brought to 37° C. and the sensor allowed to equilibrate for a minimum of 1 hour until the sensors reached a flat line continuous baseline signal. Acetaminophen was then added to the bath to a dilution of 3.8 mg/dl. The sensor was then allowed to equilibrate over 1 hour while measurements were continuously recorded from the sensor. FIG. 8 is a graph showing the sensor signal over the course of the hour. The graph indicates that the signal changed by less than 1%. Thus, the sensor was substantially insensitive to the presence of acetaminophen, indicating that the membrane substantially reduces transport of acetaminophen therethrough.

Figure 9:
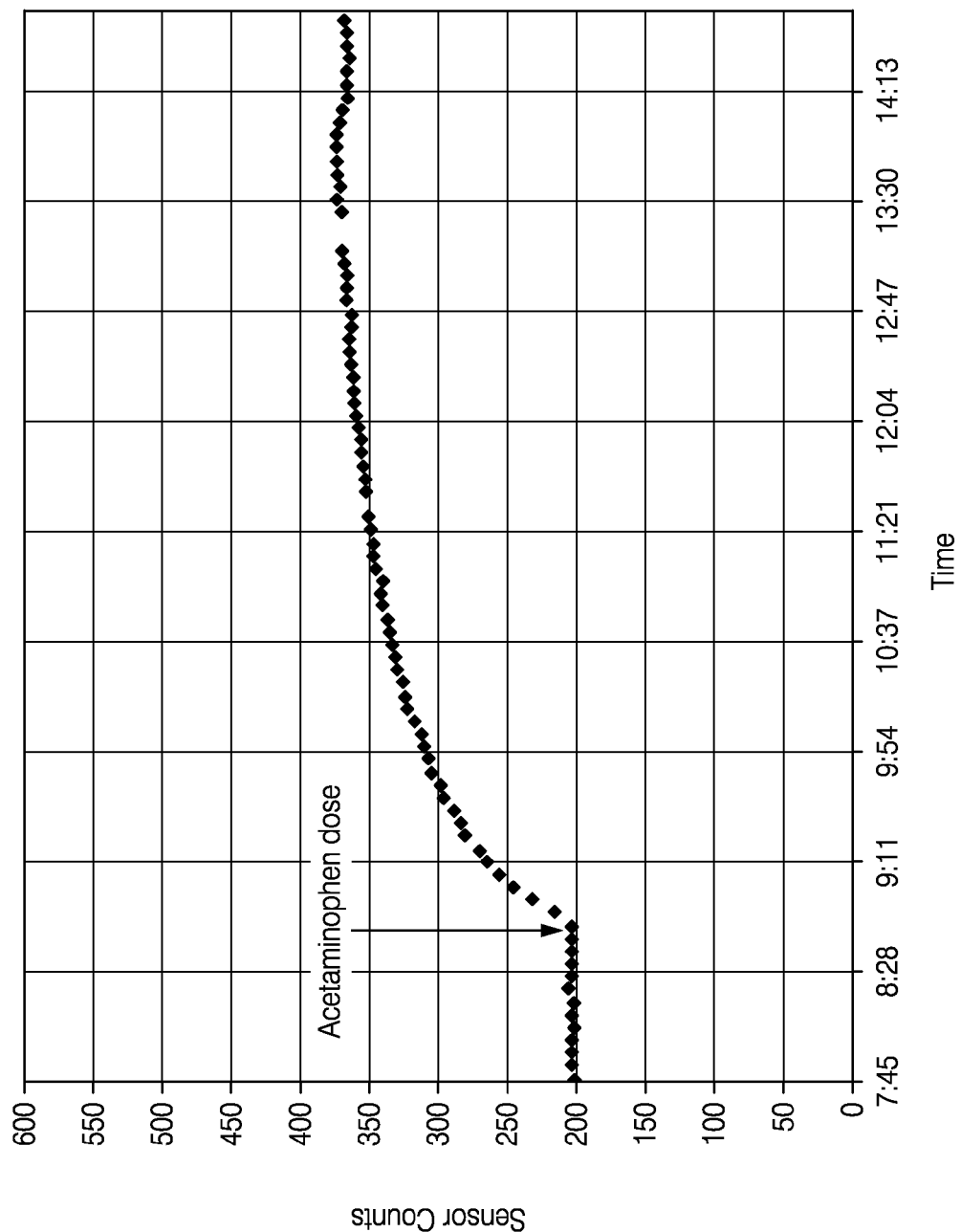
FIG. 9 is a graph depicting a sensor signal from a sensor not including a silicone/hydrophilic-hydrophobic polymer blend membrane exposed to acetaminophen.

As a comparative example, a wholly implantable glucose sensor with a membrane not including a silicone/hydrophilic-hydrophobic polymer blend was tested. The membrane in this sensor included a three-layer membrane having an electrode domain, an enzyme domain, and a polyurethane diffusion resistance domain. A porous silicone cell disruptive domain was added on top. The sensor was placed into a 2 L bath filled with PBS (saline). The continuously stirred bath was brought to 37° C. and the sensor allowed to equilibrate for a minimum of 1 hour until the sensors reached a flat line continuous baseline signal. Acetaminophen was then added to the bath to a dilution of 3.8 mg/dl. The sensor was then allowed to equilibrate over 1 hour while measurements were continuously recorded from the sensor. FIG. 9 is a graph showing the sensor signal over the course of the hour. The graph indicates that the signal changed by more than 15% after introduction of the acetaminophen. Thus, without the silicone/hydrophilic-hydrophobic polymer blend sensor was sensitive to the acetaminophen interferant.

As described herein, two or more layers of the membrane system can be disposed on a transcutaneous wire sensor. In the example of an implantable enzyme-based electrochemical glucose sensor, the membrane prevents direct contact of the biological fluid sample with the electrodes, while controlling the permeability of selected substances (for example, oxygen and glucose) present in the biological fluid through the membrane for reaction in an enzyme rich domain with subsequent electrochemical reaction of formed products at the electrodes.

The signal detected by the sensor has multiple components. These signal components include but are not limited to 1) signal related to analyte concentration (e.g., glucose), 2) baseline and 3) non-constant noise. Baseline is a substantially constant signal related to daily metabolism (e.g., substantially constant metabolism that occurs in a host over a period of time; and produces substantially constant levels of metabolic products). In contrast, non-constant noise is signal that fluctuates and is unrelated to analyte concentration or day-to-day cellular metabolism. While not wishing to be bound by theory, it is believed that non-constant noise can be caused by a variety of non-constant events and/or factors, such as but not limited to endogenous and exogenous interfering species, host wounding and wound healing and associated metabolic processes and by-products, certain disease processes, or even illness. The magnitude of each component's contribution to signal can vary over time and can be affected by a variety of factors, such as but not limited to host metabolism, exposure to non-constant interfering species, wounding, infection, and the like. It has been observed that some hosts (~20%) exhibit unusually high, sustained levels of non-constant noise, which disrupts sensor function in these hosts.

Accordingly, if a sensor is designed such that the signal contribution due to analyte (e.g., glucose) is substantially greater than the signal contribution due to baseline and/or non-constant noise, then noise will not affect the accuracy of the glucose concentration as significantly as compared to another sensor wherein a relatively lesser signal contribution due to analyte (e.g., glucose) is measured. Additionally, if a sensor is designed to reduce, attenuate, or substantially block noise-causing species, then non-constant noise will not affect the accuracy of the glucose concentration as significantly as compared to another sensor that does not attenuate, reduce, or eliminate the noise-causing species. It has been shown that the incorporation of a silicone/hydrophilic-hydrophobic polymer blended cell impermeable domain, as disclosed herein, into the membrane system both increases analyte-related signal (e.g., glucose signal) and decreases non-constant noise. In one embodiment, a silicone/hydrophilic-hydrophobic polymer blended domain is configured to substantially block the passage therethrough of at least one interferent. In preferred embodiments, a silicone/hydrophilic-hydrophobic polymer blended domain is configured to substantially block the passage therethrough of at least one non-constant noise-causing interferent, such as but not limited to acetaminophen, ascorbic acid, dopamine, ibuprofen, hydrogen peroxide (e.g., released by macrophages in the locality of the sensor) and the like.

Example 6

MED-4840/PLURONIC® F-127 Cell Impermeable Domain Formation on a Small-Structured Sensor A glucose-permeable cell impermeable domain was formed onto a small-structured sensor, as described in Example 1, using a MED-4840/PLURONIC® F-127 blend, with the following exceptions; the MED-4840/PLURONIC® F-127 blend contained 11-12% PLURONIC® F-127 and about 4% DCP. The sensor was dipped into the MED-4840/PLURONIC® F-127 blend, followed by a two-step curing process (incubating at 100° C. for 8-minutes and then at 55° C. for 2-hours).

Figure 10A:
FIG. 10A is a scanning electron micrograph showing the surface of a micellar jacket structure (e.g., a silicone-PLURONIC® polymer blend cell impermeable domain) on a small-structured glucose sensor, in one embodiment.

FIG. 10A is a scanning electron micrograph (SEM) of the surface of a small-structured sensor having a silicone/hydrophilic-hydrophobic polymer blend (e.g., silicone-PLURONIC® F-127 blend) cell impermeable domain, which illustrates a micellar jacket structure, in one embodiment. Silicone globules appear as white blobs ranging in size from about 5-10 microns to about 50 microns. The micellar jacket (see arrow) appear as darker areas between the silicone globules.

Example 7

Silicone-PLURONIC® Blend Domain Increases Analyte Sensitivity and Reduces Non-Constant Noise in Rats The effect of a Silicone/hydrophilic-hydrophobic polymer blend material (e.g., Silicone-PLURONIC® blend) cell impermeable domain on the sensor of Example 6 was tested in a non-diabetic rat model that exemplifies non-constant noise, as described elsewhere herein. For three days, each rat was implanted bilaterally with one each of a test sensor and a control sensor. The test sensors were manufactured with a Silicone-PLURONIC® blend cell impermeable domain (constructed according to Example 6). The control sensor had no Silicone-PLURONIC® blend cell impermeable domain (constructed according to Example 1). The rats were challenged with glucose infusions on Days 2 and 3. As an additional control, blood glucose levels were checked with a hand-held glucose meter (SMBG) during glucose challenge. The results from a representative rat are shown in FIGS. 10B and 10C.

FIG. 10B illustrates glucose detection by a control sensor (e.g., lacking a Silicone-PLURONIC® blend cell impermeable domain), in a non-diabetic rat. Signal (×1000) measured by the sensor is on the first Y-axis and glucose concentration (mg/dl, SMBG) is shown on the second Y-axis. Time is shown on the X-axis.

FIG. 10C illustrates glucose detection by a test sensor (e.g., having a Silicone-PLURONIC® blend cell impermeable domain), in the same rat of FIG. 10B. Signal (×1000) measured by the sensor is on the first Y-axis and glucose concentration (mg/dl, SMBG) is shown on the second Y-axis. Time is shown on the X-axis Referring now to FIG. 10B, the control sensor exhibited a substantial level of high amplitude, sporadic, non-constant noise. The rat was challenged with IV glucose at about 9:22. During the glucose challenge, the sensor exhibited a very high amplitude peak (~96,000 counts) but did not track well with the self-monitoring blood glucose meter (SMBG; e.g., hand held glucose meter) that was used as a control (not shown).

FIG. 10C illustrates the function of the test sensor (small-structured sensor having a silicone-PLURONIC® blend cell impermeable domain). The test sensor exhibited a substantially stable glucose signal, which lacked a significant non-constant noise component, for the duration of the experiment. During the glucose challenge, the test sensor signal increased to about 140,000 counts. Additionally, the test sensor tracked very closely with the SMBG (not shown) throughout the experiment.

Accordingly, it was shown that, in the case of an implantable analyte sensor, which has a cell impermeable domain including a silicone/hydrophilic-hydrophobic blend material as a component of the membrane system disposed on the electroactive surface, the cell impermeable domain both allows transport of the analyte therethrough and reduces non-constant noise.

Example 8

Silicone-PLURONIC® Blend Domain Can Function as a Resistance Domain in Rats

Figure 10D:
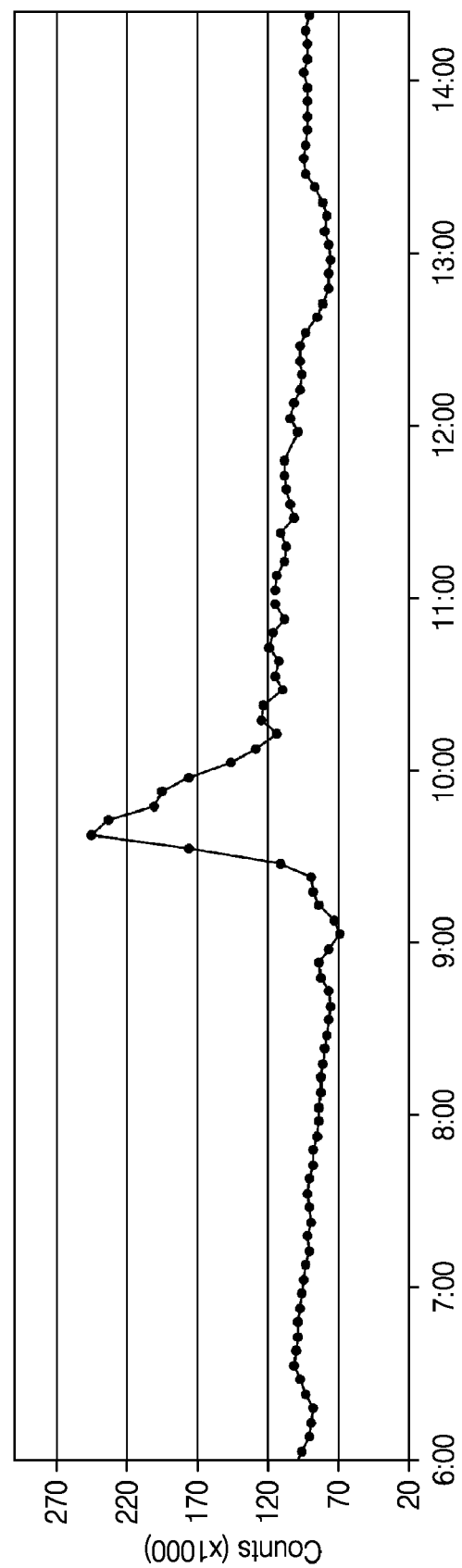
FIG. 10D is a graph showing test results from implantation of a small-structured sensor having a silicone-PLURONIC® polymer blend resistance domain, in a non-diabetic rat model.

A small-structured test sensor (e.g., short-term sensor) was built as described above, except that a single Silicone/hydrophilic-hydrophobic polymer blend material (e.g., silicone-PLURONIC® blend) domain was applied to the sensor, instead of separate resistance (e.g., polyurethane-based) and cell impermeable domains. The single Silicone/hydrophilic-hydrophobic polymer blend material domain was formed on enzyme domain, as described in Example 6, above. The test sensor and a control sensor (constructed as described above) were bilaterally implanted (transcutaneously) in a rat, as described with reference to Example 7. FIG. 10D illustrates the test results.

As shown in FIG. 10D, the sensor (without resistance domain and with cell impermeable domain) exhibited very little noise during the three days of implantation. The rat was challenged with glucose on Days 2 and 3. During glucose challenge, the sensor tracked glucose substantially similarly to SMBG.

Accordingly, it was shown that a unitary (e.g., combined) resistance/cell impermeable domain, applied to a sensor, controls the flux of the analyte through the membrane domain and attenuates and/or substantially blocks non-constant noise producing interferents, thereby improving sensor sensitivity and accuracy.

Example 9

Silicone-PLURONIC® Blend Cell Impermeable Domain Reduces Noise in Humans

Figure 11:
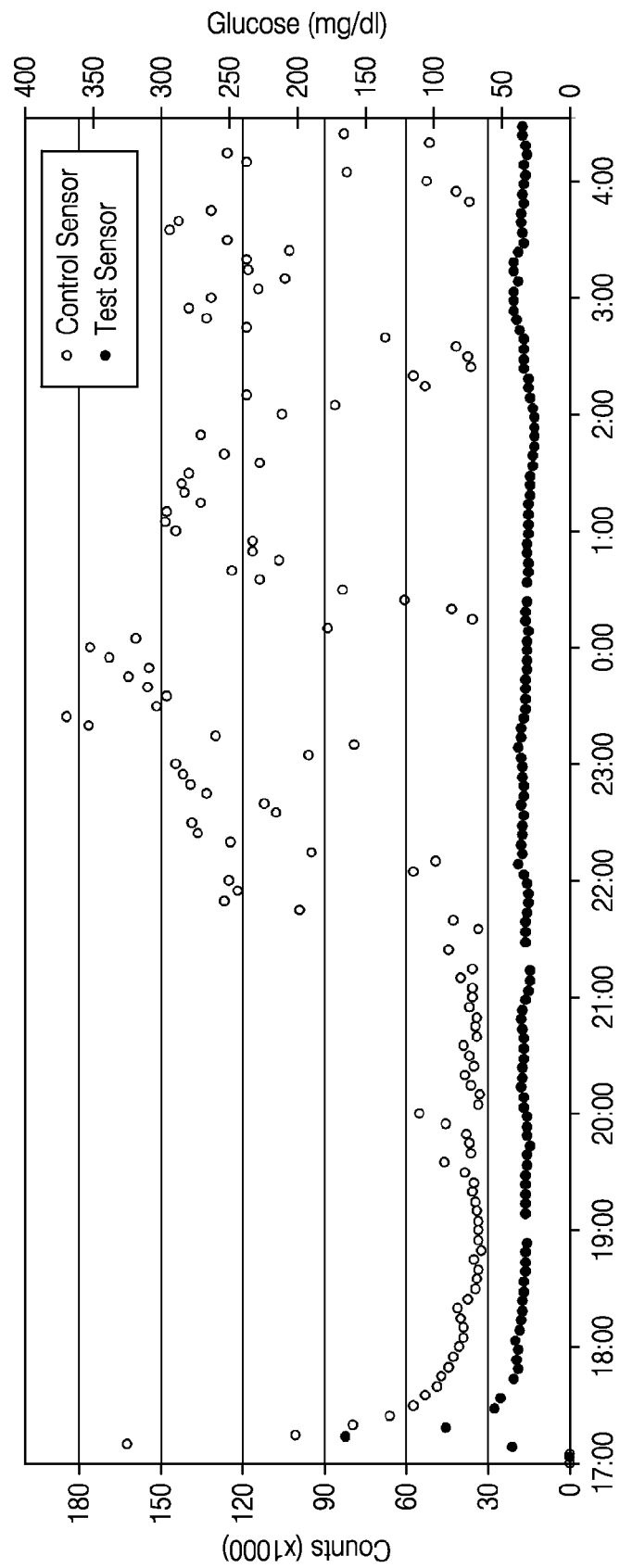
FIG. 11 is a graph showing test results during implantation of small-structured glucose sensors with (test) and without (control) a silicone-PLURONIC® polymer blend cell impermeable domain, in a non-diabetic host.

As is discussed above, about 20-30% of human hosts exhibit significant, sporadic "noisy" data when a glucose sensor has been transcutaneously implanted in their subcutaneous tissue. This type of noise is host-specific and is believed to be caused by processes that can substantially reduce sensor accuracy in this 20-30% of human hosts. The ability of a Silicone-PLURONIC® blend cell impermeable domain (e.g., on a small-structured sensor) to eliminate host-specific non-constant noise was tested in non-diabetic human volunteers known to consistently produce this type of noisy data with sensor use. Each host wore a test sensor (constructed as described in Example 6) and a control sensor (constructed as described in Example 1). An enzyme domain on both sensors contained no enzyme (e.g., no GOX), so that the sensor could measure noise (i.e., without glucose signal). Exemplary test results from one host are shown in FIG. 11, as an example. The Y-axis represents raw counts collected from the sensor. The X-axis represents time. Control sensor readings (no Silicone-PLURONIC® blend cell impermeable domain) are represented by open circles. Test sensor readings (with Silicone-PLURONIC® blend cell impermeable domain) are represented by closed circles.

As shown in FIG. 11, both the test and control sensors broke in within about 30-50 minutes. The control sensor (open circles) exhibited a baseline of about 35,000 counts. When the host became sedentary (e.g., watched a movie and then went to bed) control sensor noise levels increased substantially. The control sensor signal fluctuated from baseline levels to about 184,000 counts during an approximately 8-hour period. While not wishing to be bound by theory, it is believed that the baseline represents constant, non-analyte related noise related to substantially constant interfering species; and the fluctuating noise (during the 8-hour time period) was due to increasing and fluctuating levels of electroactive species that cause non-constant noise on the sensor, in this particular group of hosts.

The test sensor (closed circles) baseline was substantially lower, exhibiting only about 15- to 17-thousand counts. Furthermore, the test sensor showed a substantially constant signal, ranging from about 16,000-thousand counts to about 21,000-thousand counts, during the approximately 8-hour time period of sedentary activity.

It was shown that the silicone-PLURONIC® blend cell impermeable domain applied to the test sensor reduces baseline-causing signal (e.g., constant, non-analyte species) and non-constant noise-causing signal (e.g., non-constant, non-analyte species) in this particular group of hosts. Reduction of both types of noise can increase both sensor accuracy and sensitivity in this group of hosts.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

Methods and devices that are suitable for use in conjunction with aspects of the preferred embodiments are disclosed in U.S. Pat. No. 4,994,167; U.S. Pat. No. 4,757,022; U.S. Pat. No. 6,001,067; U.S. Pat. No. 6,741,877; U.S. Pat. No. 6,702,857; U.S. Pat. No. 6,558,321; U.S. Pat. No. 6,931,327; U.S. Pat. No. 6,862,465; U.S. Pat. No. 7,074,307; U.S. Pat. No. 7,081,195; U.S. Pat. No. 7,108,778; and U.S. Pat. No. 7,110,803.

Methods and devices that are suitable for use in conjunction with aspects of the preferred embodiments are disclosed in U.S. Patent Publication No. US-2005-0176136-A1; U.S. Patent Publication No. US-2005-0251083-A1; U.S. Patent Publication No. US-2005-0143635-A1; U.S. Patent Publication No. US-2005-0181012-A1; U.S. Patent Publication No. US-2005-0177036-A1; U.S. Patent Publication No. US-2005-0124873-A1; U.S. Patent Publication No. US-2005-0115832-A1; U.S. Patent Publication No. US-2005-0245799-A1; U.S. Patent Publication No. US-2005-0245795-A1; U.S. Patent Publication No. US-2005-0242479-A1; U.S. Patent Publication No. US-2005-0182451-A1; U.S. Patent Publication No. US-2005-0056552-A1; U.S. Patent Publication No. US-2005-0192557-A1; U.S. Patent Publication No. US-2005-0154271-A1; U.S. Patent Publication No. US-2004-0199059-A1; U.S. Patent Publication No. US-2005-0054909-A1; U.S. Patent Publication No. US-2005-0112169-A1; U.S. Patent Publication No. US-2005-0051427-A1; U.S. Patent Publication No. US-2003-0032874-A1; U.S. Patent Publication No. US-2005-0103625-A1; U.S. Patent Publication No. US-2005-0203360-A1; U.S. Patent Publication No. US-2005-0090607-A1; U.S. Patent Publication No. US-2005-0187720-A1; U.S. Patent Publication No. US-2005-0161346-A1; U.S. Patent Publication No. US-2006-0015020-A1; U.S. Patent Publication No. US-2005-0043598-A1; U.S. Patent Publication No. US-2003-0217966-A1; U.S. Patent Publication No. US-2005-0033132-A1; U.S. Patent Publication No. US-2005-0031689-A1; U.S. Patent Publication No. US-2004-0186362-A1; U.S. Patent Publication No. US-2005-0027463-A1; U.S. Patent Publication No. US-2005-0027181-A1; U.S. Patent Publication No. US-2005-0027180-A1; U.S. Patent Publication No. US-2006-0020187-A1; U.S. Patent Publication No. US-2006-0036142-A1; U.S. Patent Publication No. US-2006-0020192-A1; U.S. Patent Publication No. US-2006-0036143-A1; U.S. Patent Publication No. US-2006-0036140-A1; U.S. Patent Publication No. US-2006-0019327-A1; U.S. Patent Publication No. US-2006-0020186-A1; U.S. Patent Publication No. US-2006-0020189-A1; U.S. Patent Publication No. US-2006-0036139-A1; U.S. Patent Publication No. US-2006-0020191-A1; U.S. Patent Publication No. US-2006-0020188-A1; U.S. Patent Publication No. US-2006-0036141-A1; U.S. Patent Publication No. US-2006-0020190-A1; U.S. Patent Publication No. US-2006-0036145-A1; U.S. Patent Publication No. US-2006-0036144-A1; U.S. Patent Publication No. US-2006-0016700-A1; U.S. Patent Publication No. US-2006-0142651-A1; U.S. Patent Publication No. US-2006-0086624-A1; U.S. Patent Publication No. US-2006-0068208-A1; U.S. Patent Publication No. US-2006-0040402-A1; U.S. Patent Publication No. US-2006-0036142-A1; U.S. Patent Publication No. US-2006-0036141-A1; U.S. Patent Publication No. US-2006-0036143-A1; U.S. Patent Publication No. US-2006-0036140-A1; U.S. Patent Publication No. US-2006-0036139-A1; U.S. Patent Publication No. US-2006-0142651-A1; U.S. Patent Publication No. US-2006-0036145-A1; U.S. Patent Publication No. US-2006-0036144-A1; U.S. Patent Publication No. US-2006-0200022-A1; U.S. Patent Publication No. US-2006-0198864-A1; U.S. Patent Publication No. US-2006-0200019-A1; U.S. Patent Publication No. US-2006-0189856-A1; U.S. Patent Publication No. US-2006-0200020-A1; U.S. Patent Publication No. US-2006-0200970-A1; U.S. Patent Publication No. US-2006-0183984-A1; U.S. Patent Publication No. US-2006-0183985-A1; U.S. Patent Publication No. US-2006-0195029-A1; U.S. Patent Publication No. US-2006-0229512-A1; U.S. Patent Publication No. US-2006-0222566-A1; and U.S. Patent Publication No. US-2007-0016381-A1; U.S. Patent Publication No. US-2007-0027370-A1; U.S. Patent Publication No. 2007-0027385-A1; and U.S. Patent Publication No. 2007-0027384-A1.

Methods and devices that are suitable for use in conjunction with aspects of the preferred embodiments are disclosed in U.S. patent application Ser. No. 09/447,227 filed Nov. 22, 1999 and entitled "DEVICE AND METHOD FOR DETERMINING ANALYTE LEVELS"; U.S. patent application Ser. No. 11/498,410 filed Aug. 2, 2006 and entitled "SYSTEMS AND METHODS FOR REPLACING SIGNAL ARTIFACTS IN A GLUCOSE SENSOR DATA STREAM"; U.S. patent application Ser. No. 11/515,342 filed Sep. 1, 2006 and entitled "SYSTEMS AND METHODS FOR PROCESSING ANALYTE SENSOR DATA"; and U.S. patent application Ser. Nos. 11/543,683, 11/543,734, 11/543,396, 11/543,490 and 11/543,404, each of which was filed on Oct. 4, 2006, and each of which is entitled "ANALYTE SENSOR."

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification are to be understood as being modified in all instances by the term "about." Accordingly, unless indicated to the contrary, the numerical parameters set forth herein are approximations that can vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. An implantable glucose sensor, the sensor comprising:
an electroactive surface configured for insertion into a host's body; and
a membrane system comprising a cell impermeable domain disposed between the electroactive surface and the host's body when implanted, wherein the cell impermeable domain comprises a blend of a silicone polymer and a hydrophilic-hydrophobic polymer, wherein the blend is configured such that the cell impermeable domain allows transport of glucose therethrough, wherein the membrane system further comprises a diffusion resistance domain, and wherein glucose permeability of the cell impermeable domain is greater than a glucose permeability of the diffusion resistance domain.

2. The sensor of claim 1, wherein the membrane system comprises an enzyme domain positioned between the electroactive surface and the cell impermeable domain, wherein the enzyme domain comprises an enzyme.

3. The sensor of claim 1, wherein the diffusion resistance domain is positioned between the electroactive surface and the cell impermeable domain.

4. The sensor of claim 1, wherein the diffusion resistance domain comprises a silicone material configured to control flux of glucose the analyte therethrough.

5. The sensor of claim 1, wherein the hydrophilic-hydrophobic polymer comprises a hydrophilic copolymer.

6. The sensor of claim 5, wherein the hydrophilic copolymer comprises hydroxy substituents.

7. The sensor of claim 5, wherein the hydrophilic copolymer comprises a poly(ethylene oxide)-poly(propylene oxide) copolymer.

8. The sensor of claim 5, wherein the hydrophilic copolymer comprises a poly(ethylene oxide)-poly(propylene oxide)-poly(ethylene oxide) triblock polymer.

9. The sensor of claim 5, wherein at least a portion of the hydrophilic copolymer is at least partially cross-linked.

10. The sensor of claim 5, wherein from about 1% w/w to about 50% w/w of the cell impermeable domain is the hydrophilic copolymer.

11. The sensor of claim 5, wherein from about 5% w/w to about 30% w/w of the cell impermeable domain is the hydrophilic copolymer.

12. The sensor of claim 1, wherein the sensor is configured to be subcutaneously implanted.

13. The sensor of claim 1, wherein the sensor is configured to be intravascularly implanted.

14. A device configured for continuously measuring a glucose concentration in a host, the device comprising:
an electrode configured for insertion into a host's body; and
a membrane comprising a silicone material comprising a micellar jacket structure configured to attenuate or substantially block non-constant noise-producing interferents, wherein the micellar jacket structure comprises a macromolecular self-organization of silicone globules coated with a hydrophilic polymer.

15. The sensor of claim 14, wherein the silicone material comprises a blend of a silicone elastomer and a hydrophilic copolymer.

16. The sensor of claim 14, wherein the membrane comprises an enzyme domain positioned between the electroactive surface or electrode and a cell impermeable domain, wherein the enzyme domain comprises an enzyme.

17. The sensor of claim 16, wherein the enzyme domain comprises a silicone material.

18. The sensor of claim 16, wherein the enzyme domain comprises glucose oxidase.

19. The sensor of claim 14, wherein the membrane comprises a diffusion resistance domain.

20. The sensor of 19, wherein the diffusion resistance domain is positioned between the electroactive surface or electrode and a cell impermeable domain.

21. The sensor of claim 19, wherein the membrane comprises a cell impermeable membrane, and wherein the cell impermeable domain and the diffusion resistance domain comprise a unitary layer configured to control flux of glucose therethrough.

22. The sensor of claim 14, wherein the sensor is configured to be subcutaneously implanted.

23. The sensor of claim 14, wherein the sensor is configured to be intravascularly implanted.

24. The sensor of claim 14, wherein the sensor comprises an architecture with at least one dimension less than about 1 mm.

25. The sensor of claim 14, wherein the sensor comprises a bulk metal or an electrically conductive wire.

26. A continuous glucose measuring device, the device comprising:
a sensing mechanism configured for continuous measurement of a host's glucose concentration; and
a membrane system comprising a unitary biointerface layer and an enzyme layer, wherein the biointerface layer is formed on the enzyme layer, wherein the biointerface layer is configured to be impermeable to cells or cell processes and configured to control a flux of oxygen and glucose to the enzyme layer, and wherein the biointerface and the enzyme layer each comprise a blend of a silicone polymer and a hydrophilic-hydrophobic polymer configured such that the biointerface layer allows transport of glucose therethrough.

27. The sensor of claim 26, wherein the unitary biointerface layer is configured to substantially block passage therethrough of at least one non-constant noise causing interferent.

28. An electrochemical glucose sensor, the sensor comprising:
an electroactive surface configured for insertion into a host's body; and
a membrane comprising a blend of three-dimensional silicone particles and a hydrophilic-hydrophobic polymer, wherein the membrane comprises a macromolecular self-organization of the silicone particles and a hydrophilic-hydrophobic polymer which, when substantially blended, creates a mechanism configured to attenuate or substantially block non-constant noise-producing interferents.

29. The sensor of claim 28, wherein the sensor is configured to be subcutaneously implanted.

30. The sensor of claim 28, wherein the sensor is configured to be intravascularly implanted.

31. The sensor of claim 28, wherein the interferents comprise at least one substance selected from the group consisting of hydrogen peroxide, reactive oxygen species, and reactive nitrogen species.

32. The sensor of claim 28, wherein the interferents comprise at least one substance selected from the group consisting of acetaminophen, ascorbic acid, dopamine, ibuprofen, salicylic acid, tolbutamide, tetracycline, creatinine, uric acid, ephedrine, L-dopa, methyl dopa, and tolazamide.

33. The sensor of claim 28, wherein the sensor comprises an architecture with at least one dimension less than about 1 mm.

34. The sensor of claim 28, wherein the sensor comprises a bulk metal or an electrically conductive wire.

35. The sensor of claim 28, wherein the membrane comprises a diffusion resistance domain.

36. The sensor of claim 35, wherein the membrane comprises a cell impermeable domain, and wherein the cell impermeable domain and/or resistance domain exhibits an oxygen to glucose permeability ratio of at least about 200:1.

37. The sensor of claim 28, wherein the membrane comprises an enzyme domain positioned between the electroactive surface or electrode and a cell impermeable domain, wherein the enzyme domain comprises an enzyme.

38. The sensor of claim 37, wherein the enzyme domain comprises a silicone material.

39. The sensor of claim 37, wherein the enzyme domain comprises glucose oxidase.

40. The sensor of claim 35, wherein the membrane comprises a cell impermeable domain, and wherein the cell impermeable domain and/or resistance domain exhibits an oxygen to glucose permeability ratio of at least about 50:1.

41. The sensor of 35, wherein the diffusion resistance domain is positioned between the electroactive surface or electrode and a cell impermeable domain.

42. The sensor of claim 35, wherein the membrane comprises a cell impermeable membrane, and wherein the cell impermeable domain and the diffusion resistance domain comprise a unitary layer configured to control flux of glucose therethrough.

43. The sensor of claim 35, wherein the diffusion resistance domain comprises a silicone material configured to control flux of glucose therethrough.

* * * * *

UNITED STATES PATENT AND TRADEMARK OFFICE
CERTIFICATE OF CORRECTION

PATENT NO.       : 7,828,728 B2
APPLICATION NO.  : 11/675063
DATED            : November 9, 2010
INVENTOR(S)      : Boock et al.

It is certified that error appears in the above-identified patent and that said Letters Patent is hereby corrected as shown below:

| Issued Patent | | Description of Discrepancy |
|---|---|---|
| Column | Line | |
| (Item 56) Page 6 Col. 2 | 18 | Under Other Publications, change "Senso" to --Sensor--. |
| (Item 56) Page 7 Col. 1 | 9 | Under Other Publications, change "Membran," to --Membrane,--. |
| (Item 56) Page 7 Col. 1 | 31 | Under Other Publications, change "Membrance" to --Membrane--. |
| (Item 56) Page 7 Col. 1 | 55 | Under Other Publications, change "artifical" to --artificial--. |
| (Item 56) Page 7 Col. 1 | 66 | Under Other Publications, change ""xenogenic."" to --"xenogeneic."--. |
| (Item 56) Page 7 Col. 2 | 2 | Under Other Publications, change "hypoglycaemic" to --hypoglycemic--. |
| (Item 56) Page 7 Col. 2 | 68 | Under Other Publications, change "impintable," to --implantable,--. |

Signed and Sealed this
Twenty-sixth Day of April, 2011

David J. Kappos
*Director of the United States Patent and Trademark Office*

| | | |
|---|---|---|
| (Item 56)<br>Page 8<br>Col. 1 | 2 | Under Other Publications,<br>change "reliablity"<br>to --reliability--. |
| (Item 56)<br>Page 8<br>Col. 1 | 13 | Under Other Publications,<br>change "Enzymlology,"<br>to --Enzymology,--. |
| (Item 56)<br>Page 8<br>Col. 1 | 22 | Under Other Publications,<br>change "artifical" to --artificial--. |
| (Item 56)<br>Page 8<br>Col. 1 | 47 | Under Other Publications,<br>change "glocuse" to --glucose--. |
| (Item 56)<br>Page 8<br>Col. 1 | 48 | Under Other Publications,<br>change "Diabetese" to --Diabetes--. |
| (Item 56)<br>Page 8<br>Col. 1 | 61 | Under Other Publications,<br>change "Hypoglycaemia"<br>to --Hypoglycemia--. |
| (Item 56)<br>Page 8<br>Col. 2 | 8 | Under Other Publications,<br>change "Diabetese" to --Diabetes--. |
| (Item 56)<br>Page 8<br>Col. 2 | 27 | Under Other Publications,<br>change "inactiviation"<br>to --inactivation--. |
| (Item 56)<br>Page 9<br>Col. 1 | 12 | Under Other Publications,<br>change "Aniodic" to --Anodic--. |
| (Item 56)<br>Page 9<br>Col. 1 | 60 | Under Other Publications,<br>change "activitiy," to --activity,--. |
| (Item 56)<br>Page 9<br>Col. 2 | 2 | Under Other Publications,<br>change "Biosensors& Beioelectronics,"<br>to --Biosensors & Bioelectronics,--. |

CERTIFICATE OF CORRECTION (continued)
U.S. Pat. No. 7,828,728 B2

| | | |
|---|---|---|
| (Item 56) Page 9 Col. 2 | 3 | Under Other Publications, change "glocuse" to --glucose--. |
| (Item 56) Page 9 Col. 2 | 12 | Under Other Publications, change "valication" to --validation--. |
| (Item 56) Page 9 Col. 2 | 13 | Under Other Publications, change "iunsulin interaaction in tyhpe" to --insulin interaction in type--. |
| (Item 56) Page 9 Col. 2 | 26 | Under Other Publications, change "Electronanalysis" to --Electroanalysis--. |
| (Item 56) Page 9 Col. 2 | 41 | Under Other Publications, change "artifical" to --artificial--. |
| (Item 56) Page 9 Col. 2 | 50 | Under Other Publications, change "amperometeric" to --amperometric--. |
| (Item 56) Page 10 Col. 1 | 18 | Under Other Publications, change "metobolites," to --metabolites,--. |
| (Item 56) Page 10 Col. 1 | 20 | Under Other Publications, change "cholesteral and cholesteral" to --cholesterol and cholesterol--. |
| (Item 56) Page 10 Col. 1 | 22 | Under Other Publications, change "Apllied" to --Applied--. |
| (Item 56) Page 10 Col. 2 | 16 | Under Other Publications, change "Subcutaenous" to --Subcutaneous--. |
| (Item 56) Page 10 Col. 2 | 22 | Under Other Publications, change "assitance" to --assistance--. |

CERTIFICATE OF CORRECTION (continued)
U.S. Pat. No. 7,828,728 B2

| | | |
|---|---|---|
| (Item 56) Page 10 Col. 2 | 63 | Under Other Publications, change "pancrease" to --pancreas--. |
| (Item 56) Page 11 Col. 1 | 34 | Under Other Publications, change "Deabetes" to --Diabetes--. |
| (Item 56) Page 11 Col. 1 | 53 | Under Other Publications, change "Tranducers" to --Transducers--. |
| 5 | 1 | Change "biotimidase;" to --biotinidase;--. |
| 5 | 11 | Change "hemoglobin F." to --hemoglobin F,--. |
| 5 | 28 | Change "phenyloin;" to --phenytoin--. |
| 5 | 35-36 | Change "Giardia duodenalisa" to --Giardia duodenalis--. |
| 5 | 43 | Change "Trepenoma pallidium," to --Treponema pallidum,--. |
| 5 | 44 | Change "stomatis" to --stomatitis--. |
| 5 | 65 | Change "(barbituates," to --(barbiturates,--. |
| 8 | 65 | Change "Cl" to --Cl$^-$--. |
| 8 | 65 | Change "Cl"to --Cl$^-$--. |
| 30 | 42 | After "itself" insert --.--. |
| 50 | 65 | Change "hydroxyapeptite," to --hydroxyapatite,--. |
| 50 | 67 | Change "nintinol," to --nitinol,--. |

CERTIFICATE OF CORRECTION (continued)
U.S. Pat. No. 7,828,728 B2

| 54 | 64 | After "vivo" insert --,--. |
| 55 | 35 | Change "SYNPERONICS®" to --SYNTRONICS®--. |
| 56 | 51 | Change "hydroxyapeptite," to --hydroxyapatite,--. |
| 57 | 59 | Change "cm/cm² s" to -- cm/cm²s--. |
| 60 | 57 | Change "SYNPERONICS®" to --SYNTRONICS®--. |
| 65 | 36 | Change "melenamic" to --mefenamic--. |
| 65 | 41 | Change "betamethesone," to --betamethasone,--. |
| 65 | 55 | Change "infiximab)," to --infliximab),--. |
| 65 | 57 | Change "methothrexate," to --methotrexate,--. |
| 65 | 58 | Change "mitomycine," to --mitomycin,--. |
| 65 | 60 | Change "batimstat," to --batimastat,--. |
| 65 | 66 | Change "Cerivasttin)," to -- Cerivastatin),--. |
| 66 | 7 | Change "aminoclycosides" to --aminoglycosides--. |
| 67 | 18 | Change "glenipin," to --genipin,--. |
| 85 | 10 | In Claim 4, after "glucose" delete "the analyte". |
| 85 | 56 | In Claim 20, after "of" insert --claim--. |
| 87 | 5 | In Claim 41, after "of" insert --claim--. |